US012578324B2

(12) United States Patent
Dong et al.

(10) Patent No.: US 12,578,324 B2
(45) Date of Patent: Mar. 17, 2026

(54) METHODS AND COMPOSITIONS FOR IMPROVED INSECT REPELLENCY

(71) Applicant: Board of Trustees of Michigan State University, East Lansing, MI (US)

(72) Inventors: Ke Dong, Okemos, MI (US); Feng Liu, Nashville, TN (US); Qiang Wang, Zhenjiang Jiangsu (CN); Peng Xu, East Lansing, MI (US); Felipe Andreazza, Durham, NC (US); Wilson Rodrigues Valbon, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 701 days.

(21) Appl. No.: 17/351,620

(22) Filed: Jun. 18, 2021

(65) Prior Publication Data

US 2021/0392882 A1 Dec. 23, 2021

Related U.S. Application Data

(60) Provisional application No. 63/040,918, filed on Jun. 18, 2020.

(51) Int. Cl.

| | |
|---|---|
| ***G01N 33/50*** | (2006.01) |
| ***A01N 31/02*** | (2006.01) |
| ***A01N 51/00*** | (2006.01) |
| ***A01N 65/44*** | (2009.01) |
| ***C07K 14/435*** | (2006.01) |

(52) U.S. Cl.

CPC ......... *G01N 33/5041* (2013.01); *A01N 31/02* (2013.01); *A01N 51/00* (2013.01); *A01N 65/44* (2013.01); *C07K 14/43581* (2013.01); *G01N 33/5085* (2013.01); *G01N 2333/43591* (2013.01)

(58) Field of Classification Search

CPC ......... A01N 51/00; G01N 2333/43591; C07K 14/43563

USPC .................................................. 435/7.2, 348

See application file for complete search history.

(56) References Cited

PUBLICATIONS

Dickens et al. , Mini review: Mode of action of mosquito repellents, Pestic. Biochem. Physiol, (2013), http://dx.doi.org/10.1016/j.pestbp.2013.02.006. (Year: 2013).*

* cited by examiner

*Primary Examiner* — Gregory S Emch
*Assistant Examiner* — Omar Ramadan
(74) *Attorney, Agent, or Firm* — McKee, Voorhees & Sease, PLC

(57) ABSTRACT

Described herein are compositions and methods useful for isolating compositions that repel insects, including mosquitoes.

11 Claims, 27 Drawing Sheets

Specification includes a Sequence Listing.

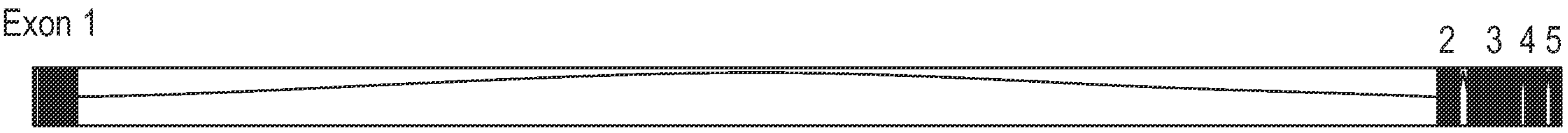

AaOr31$^{+/+}$ CCTAATTTGTTTAACCTTTCAGCTGGAACTAGCGAAATCGAATCAATTGAGCGGAACAACAAAATCGATCGATTTCTAGCGACGGCTTAT
AaOr31$^{-/-}$ CCTAATT-----------------------------------------------------------GCGGAACAACAAAATCGATCGATTT-------------CGGCTTAT

AaOr31$^{+/+}$ CTGATGTCGGCATCTGCAACGGGATCACTGTTCATCATTGCGGCACTGGCTAAAGGATGTTATAAGTTGATTTTTCAAAACATCATCGAG
AaOr31$^{-/-}$ CTGATGTCGGCATCTGCAACGGGATCACTGTTCATCATTGCGGCACTGGCTAAAGGATGTTATAAGTTGATTTTTCAAAACATCATCGAG

FIG. 3G

SEQUENCE LISTING

```
<160> NUMBER OF SEQ ID NOS: 11

<210> SEQ ID NO 1
<211> LENGTH: 381
<212> TYPE: PRT
<213> ORGANISM: Aedes aegypti

<400> SEQUENCE: 1

Met Ala Pro Thr Gln Asn Gly Arg Asp Arg Glu Lys Phe Leu Arg Val
1               5                   10                  15

Gln Leu Leu Cys Leu Ala Leu Ile Gly Ile Lys Arg His Glu Thr Val
            20                  25                  30

Ser Ser Arg Thr Ile Phe His Val Cys Phe Ile Ser Met Val Ile Met
        35                  40                  45

Asp Leu Ala Thr Ile Leu Phe Ala Leu Glu His Ala Asn Asp Ile Ala
    50                  55                  60

Leu Val Cys Asp Cys Leu Gly Pro Thr Phe Thr Ala Tyr Leu Gly Ile
65                  70                  75                  80

Val Lys Gln Tyr Cys Leu Ser Ala His Arg Val Glu Leu Trp Asn Ile
                85                  90                  95

Ile Glu Thr Leu Arg Arg Leu Lys Asp Tyr Ala Gly Ile Ser Glu Ile
            100                 105                 110

Glu Ser Ile Glu Arg Asn Asn Lys Ile Asp Arg Phe Leu Ala Thr Ala
        115                 120                 125

Tyr Leu Met Ser Ala Ser Ala Thr Gly Ser Leu Phe Ile Ile Ala Ala
    130                 135                 140

Leu Ala Lys Gly Cys Tyr Lys Leu Ile Phe Gln Asn Ile Ile Glu Trp
145                 150                 155                 160

Gly Phe Pro Leu Ser Leu Ser Phe Pro Phe Lys Thr Ser His Pro Ile
                165                 170                 175
```

-continued

Val Phe Gly Met Phe Phe Val Trp Ser Ser Ala Ala Ile Tyr Ile Val
180 185 190

Val Phe Cys Ser Val Ser Ser Asp Ala Ser Phe Gly Gly Leu Ala Ser
195 200 205

Asn Val Val Val His Phe Lys Leu Leu Gln Lys Arg Leu Gln Asp Ala
210 215 220

Thr Phe Ala Asp Asn Asp Glu Asn Leu Lys Gln Leu Ile Glu Tyr His
225 230 235 240

Ser Leu Leu Leu Asn Leu Ser Arg Lys Ile Met Ser Ser Phe Arg Val
245 250 255

Ile Ile Ile Asn Asn Leu Leu Val Ala Ser Val Leu Leu Cys Val Leu
260 265 270

Gly Phe Gln Leu Val Met Phe Leu Gly Ser Thr Leu Met Leu Ile Tyr
275 280 285

Leu Met Tyr Val Thr Ala Ile Val Ile Gln Ile Thr Phe Phe Ala Tyr
290 295 300

Tyr Gly Ser Leu Leu Leu His Glu Ser Glu Glu Val Ser Ile Ser Ile
305 310 315 320

Tyr Cys Ser Asn Trp Tyr Glu Ala Ser Pro Lys Thr Arg Arg Ile Leu
325 330 335

Leu Gln Cys Leu Met Arg Ala Gln Val Pro Val Asn Thr Lys Ala Gly
340 345 350

Phe Met Val Ala Ser Leu Pro Thr Leu Arg Ala Ile Leu Asn Ser Ala
355 360 365

Gly Ser Tyr Val Ala Leu Leu Leu Ser Phe Thr Asp Asn
370 375 380

<210> SEQ ID NO 2
<211> LENGTH: 381
<212> TYPE: PRT
<213> ORGANISM: Aedes aegypti

<400> SEQUENCE: 2

Met Ala Pro Thr Gln Asn Gly Arg Asp Arg Glu Lys Phe Leu Arg Val
1 5 10 15

Gln Leu Leu Cys Leu Ala Leu Ile Gly Ile Lys Arg His Glu Thr Val
20 25 30

Ser Ser Arg Thr Ile Phe His Val Cys Phe Ile Ser Met Val Ile Met
35 40 45

Asp Leu Ala Thr Ile Leu Phe Ala Leu Glu His Ala Asn Asp Ile Ala
50 55 60

Leu Val Cys Asp Cys Leu Gly Pro Thr Phe Thr Ala Tyr Leu Gly Ile
65 70 75 80

Val Lys Gln Tyr Cys Leu Ser Ala His Arg Val Glu Leu Trp Asn Ile
85 90 95

Ile Glu Thr Leu Arg Arg Leu Lys Asp Tyr Ala Gly Thr Ser Glu Ile
100 105 110

Glu Ser Ile Glu Arg Asn Asn Lys Ile Asp Arg Phe Leu Ala Thr Ala
115 120 125

Tyr Leu Met Ser Ala Ser Ala Thr Gly Ser Leu Phe Ile Ile Ala Ala
130 135 140

Leu Ala Lys Gly Cys Tyr Lys Leu Ile Phe Gln Asn Ile Ile Glu Trp
145 150 155 160

```
Gly Phe Pro Leu Ser Leu Ser Phe Pro Phe Lys Thr Ser His Pro Ile
                165                 170                 175

Val Phe Gly Val Phe Phe Val Trp Ser Ser Ala Ala Ile Tyr Ile Val
            180                 185                 190

Val Phe Cys Ser Val Ser Ser Asp Ala Ser Phe Gly Gly Leu Ala Ser
        195                 200                 205

Asn Val Val Val His Phe Lys Leu Leu Gln Lys Arg Leu Gln Asp Ala
    210                 215                 220

Thr Phe Ala Asp Asn Asp Glu Asn Leu Lys Gln Leu Ile Glu Tyr His
225                 230                 235                 240

Ser Leu Leu Leu Asn Leu Ser Arg Lys Ile Met Ser Ser Phe Arg Val
                245                 250                 255

Ile Ile Ile Asn Asn Leu Leu Val Ala Ser Val Leu Leu Cys Val Leu
            260                 265                 270

Gly Phe Gln Leu Val Met Phe Leu Gly Ser Thr Leu Met Leu Ile Tyr
        275                 280                 285

Leu Met Tyr Val Thr Ala Ile Val Ile Gln Ile Thr Phe Phe Ala Tyr
    290                 295                 300

Tyr Gly Ser Leu Leu Ser His Glu Ser Glu Glu Val Ser Ser Ser Ile
305                 310                 315                 320

Tyr Cys Ser Asn Trp Tyr Glu Ala Ser Pro Lys Thr Arg Arg Ile Leu
                325                 330                 335

Leu Gln Cys Leu Met Arg Ala Gln Val Pro Val Asn Thr Lys Ala Gly
            340                 345                 350

Phe Met Val Ala Ser Leu Pro Thr Leu Arg Ala Ile Leu Asn Ser Ala
        355                 360                 365

Gly Ser Tyr Val Ala Leu Leu Leu Ser Phe Thr Asp Asn
    370                 375                 380
```

<210> SEQ ID NO 3
<211> LENGTH: 395
<212> TYPE: PRT
<213> ORGANISM: Anopheles gambiae

<400> SEQUENCE: 3

```
Met Leu Arg Leu Ser Pro Glu Asp Pro Lys Ala Val Met Pro Phe Ala
1               5                   10                  15

Lys Arg Leu Leu Arg Leu Ser Gly Phe Arg Gln Glu Thr Glu Gln Leu
            20                  25                  30

Glu Lys Gln Ile Phe Phe Asn Leu Phe Val Tyr Val Ala Ala Leu Leu
        35                  40                  45

Ile Pro Lys Val Cys Ser Pro Tyr Pro Asp Ser Glu Ala Ile Ile Arg
    50                  55                  60

Gly Leu Ser Glu Leu Ile Phe Phe Thr Asn Val Tyr Val Gly Tyr Tyr
65                  70                  75                  80

Cys Phe Val Val Gln His Arg His Tyr Arg Asp Leu Leu Asp Glu Ile
                85                  90                  95

Gln Ser Phe Val Asn Val Val Tyr Pro Thr Ser Gln Gln Pro Glu Ser
            100                 105                 110

Pro Ser Glu Arg Thr Leu Ile Lys Leu Asn Val Lys Ile Asn Lys Ile
        115                 120                 125

Ser Val Leu Tyr Cys Trp Tyr Leu Ala Ala Ala Gly Leu Ile Tyr Trp
    130                 135                 140
```

```
Ser Thr Pro Cys Leu Met Thr Tyr His Ser Val Leu Lys Ala Lys Ala
145                 150                 155                 160

Glu Tyr Gly Pro Asn His Pro Ile Arg Phe Tyr Pro Asn Leu Glu Gly
                165                 170                 175

Ser Phe Tyr Gly Leu Asp Asn Arg Thr Ser Val Tyr Gly Tyr Ala Ala
            180                 185                 190

Phe Ser Ile Val Ala Leu Leu Val Phe Ala Phe Ala Ser Tyr Asn Asn
        195                 200                 205

Ala Thr Lys Leu Leu Thr Ile Leu Ser Thr Ile Lys Tyr Cys Ser Thr
    210                 215                 220

Leu Leu Gln Leu Val Gly Val Glu Val Asp Asn Leu Asn His Thr Ser
225                 230                 235                 240

Ser Glu Ala Ile Gly Arg Glu Leu Lys Lys Val Ile Gln Leu His Gln
                245                 250                 255

Leu Ala Leu Arg Cys Val Ala Leu Leu Asn Gln Thr Leu Ser Phe Val
            260                 265                 270

Met Ala Leu Gln Leu Ala Leu Cys Ile Leu Thr Trp Cys Phe Thr Leu
        275                 280                 285

Leu Tyr Ile Leu Ile Val Gly Phe Asn Ala Ile Ala Thr Asn Gly Leu
    290                 295                 300

Leu Ile Met Ile Asn Met Thr Leu Glu Met Phe Gly Tyr Cys Phe Phe
305                 310                 315                 320

Cys Thr Glu Leu Asp Thr Thr Gly Lys Ile Val Ser Arg Gln Met Tyr
                325                 330                 335

Glu Phe Arg Trp Glu Gln His Arg Pro Thr Val Gln Lys Met Val Ala
            340                 345                 350

Met Ile Ile Ala Arg Ser Gln Thr Pro Leu Gln Ile Thr Ala Cys Gly
        355                 360                 365

Phe Ile Pro Ile Asn Leu Glu Leu Phe Thr Lys Val Val Lys His Ser
    370                 375                 380

Tyr Thr Val Leu Ala Val Leu Lys Asp Leu Ile
385                 390                 395


<210> SEQ ID NO 4
<211> LENGTH: 372
<212> TYPE: PRT
<213> ORGANISM: Anopheles gambiae

<400> SEQUENCE: 4

Met Leu Ala Ala Glu Thr Val Asp Phe Phe Arg Val Gln Ser Ile Cys
1               5                   10                  15

Leu Arg Ala Ile Gly Ile Ala Arg Thr Asp Ser Phe Arg Gly Arg Val
            20                  25                  30

Leu Phe Ala Val Ser Phe Phe Thr Val Leu Val Met Met Leu Gly Thr
        35                  40                  45

Val Met Phe Ala Phe Lys His Ile Asp Gln Ile Met Leu Leu Cys Asp
    50                  55                  60

Cys Leu Gly Pro Thr Phe Thr Ala Tyr Leu Gly Leu Val Arg Gln Tyr
65                  70                  75                  80

Asn Leu Leu Leu His Arg Ser Glu Leu Trp Ser Ile Val Asp Glu Phe
                85                  90                  95

Ala Ala Leu Lys His Ser Leu Gln Ser Ser Glu Ile Arg Ile Val Gln
            100                 105                 110
```

Lys Tyr Asn Arg Ile Asp Arg Phe Leu Ala Trp Ala Tyr Leu Ile Thr
        115                 120                 125

Ala Met Ser Thr Gly Val Leu Phe Val Gly Val Ala Leu Val Leu Val
    130                 135                 140

Phe Leu Ser Glu Lys Ser Asp Trp Lys Leu Pro Leu Leu Met Asp Phe
145                 150                 155                 160

Pro Phe Asp Val Lys His Pro Val Thr Phe Thr Ile Phe Phe Val Trp
                165                 170                 175

Cys Ser Val Ala Ile Phe Trp Val Val Leu Asp Cys Val Ala Cys Asp
            180                 185                 190

Ser Thr Phe Gly Thr Phe Ser Ser Cys Leu Val Ala His Phe Val Ile
        195                 200                 205

Ile Gln Glu Arg Phe Glu Gly Leu Arg Phe Asp Asp Gly Asn Arg Glu
    210                 215                 220

Leu Lys Lys Leu Ile Glu His His Lys Tyr Ile Leu Arg Ile Ser Asp
225                 230                 235                 240

Arg Val Ile Asn Ala Tyr Lys Asn Val Ile Leu Asn Gln Leu Leu Ile
                245                 250                 255

Ser Ser Val Leu Leu Cys Met Leu Gly Phe Gln Leu Val Ile Ser Val
            260                 265                 270

Gly Thr Asn Ile Met Val Val Tyr Val Ala Tyr Gly Met Ala Ile Thr
        275                 280                 285

Ile Gln Val Thr Tyr Tyr Cys Tyr Tyr Gly Ser Gln Leu Tyr Tyr Glu
    290                 295                 300

Ser Thr Gln Val His Asp Ala Val Phe Lys Ser Lys Trp Tyr Asp Ala
305                 310                 315                 320

Ser Val Ala Thr Gln Lys Met Leu Ile Asn Cys Met Met Arg Ala Lys
                325                 330                 335

Lys Pro Val Asn Ala Lys Ser Gly Phe Thr Gln Ala Ser Leu Pro Thr
            340                 345                 350

Leu Asn Ala Ile Leu Asn Ser Ala Gly Ser Tyr Val Ala Leu Leu Met
        355                 360                 365

Ser Leu Met Glu
    370

<210> SEQ ID NO 5
<211> LENGTH: 376
<212> TYPE: PRT
<213> ORGANISM: Anopheles gambiae

<400> SEQUENCE: 5

Met Lys Leu Leu Glu Leu Asp Asn Pro Arg Glu Ala Ile Ala Ile Gly
1               5                   10                  15

Cys Arg Leu Leu Lys Leu Phe Gly Leu Gly Arg Asp Glu Arg Phe Lys
            20                  25                  30

Leu Val Tyr Trp Leu Gln Cys Val Ala Tyr Leu Ala Phe Ser Ile Val
        35                  40                  45

Pro Arg Leu Leu Val Glu Ile Glu Asp Met Val Ala Leu Met Arg Leu
    50                  55                  60

Ile Ala Glu Leu Val Phe Val Val Tyr Leu Cys Leu Gln Ile Met Ala
65                  70                  75                  80

Leu Tyr Cys Arg Arg Arg Gln Leu Tyr Arg Leu Val Asp Met Leu Gln
                85                  90                  95

```
Gln Cys Ile Asp Ile Pro Tyr Ser Glu Gln Ile Glu Ser Phe Leu Ile
            100                 105                 110

Arg Ser Asn Val Lys Ile Asn Gln Ser Ser Ala Ala Tyr Ala Arg Phe
        115                 120                 125

Phe Met Cys Val Tyr Val Leu Tyr Cys Thr Met Ser Pro Leu Ala Ser
    130                 135                 140

Gly Phe Val Tyr Ile Arg Asn Gln Arg Asn Ala Thr Gly Val Gln Glu
145                 150                 155                 160

Asp Leu Tyr Asp Leu Asp Ile Arg Tyr Asn Pro Leu His Tyr Ser Ile
                165                 170                 175

Tyr Ala Gly Leu Ile Phe Val Leu Ser Ala Ile Ser Ser Leu Ser Leu
            180                 185                 190

Cys Thr Lys Asp Val Ile Asp Ile Ala Ala Ile Lys Thr Val Thr Leu
        195                 200                 205

Val Phe Gly Ile Val Thr Met Gln Ile Arg Asp Leu His Glu Gln Ile
    210                 215                 220

Thr Gln Glu Arg Leu Asn Arg Val Ile Lys Ser His Ser Asn Ala Leu
225                 230                 235                 240

Ser Cys Ala Thr Gln Leu Glu Gln Ala Leu Asn Leu Ser Val Leu Phe
                245                 250                 255

Gln Phe Ala Ser Cys Ser Ala Ile Trp Cys Leu Met Leu Phe Tyr Ile
            260                 265                 270

Leu Leu Met Gly Leu Asp Ser Arg Val Leu Ser Val Val Leu Leu Leu
        275                 280                 285

Val Ile Val Ser Ile Glu Thr Tyr Ala Tyr Cys Met Leu Gly Ser Gln
    290                 295                 300

Leu Thr Thr Gln Gly Glu Asp Leu Leu Met Ala Leu Gln Gln Leu Ser
305                 310                 315                 320

Trp Tyr Asp Gln Pro Val Pro Ile Gln Arg Gln Ile Leu Leu Met Ile
                325                 330                 335

Arg Arg Ser Gln Thr Pro Leu Ile Leu Arg Ala Gly Lys Leu Phe Ser
            340                 345                 350

Ala Asn Val Val Gln Phe Gly Asp Ile Val Gln Lys Ser Tyr Ser Phe
        355                 360                 365

Phe Leu Val Leu Lys Asn Val Phe
    370                 375
```

<210> SEQ ID NO 6
<211> LENGTH: 411
<212> TYPE: PRT
<213> ORGANISM: Anopheles gambiae

<400> SEQUENCE: 6

```
Met Thr Val Val His Arg Ile Val Ser Phe Gly Tyr Asn Leu Leu Gln
1               5                   10                  15

Arg His Phe Asn Val Gly His Pro Thr Glu Gln Phe Phe Leu Leu Arg
            20                  25                  30

Cys Leu Asp Val Val Ser Pro Ala Met Leu Leu Gln Arg Pro Arg Ser
        35                  40                  45

Asn Leu Glu Val Ala Leu Lys Thr Leu Cys Leu Ser Val Met Val Ala
    50                  55                  60

His Thr Ile Ala Leu Ala Tyr Asp Phe Ser Gln Gln Met Asp Val Arg
65                  70                  75                  80
```

```
Leu Ala Leu Asp Met Leu Cys Met Leu Ser Leu Phe Val Ser Ile Ile
                85                  90                  95

Leu Arg Ser Thr Cys Met Arg Gln Tyr Leu Ser His Ile Asp Ala Leu
            100                 105                 110

Asp Arg Leu Glu Arg Arg Pro Thr Phe Arg Val Gly Thr Pro Tyr Ala
        115                 120                 125

Asp Glu Ser Arg Arg Asn Val Ala Leu Gln Asn Ser Arg Tyr Leu Gly
    130                 135                 140

Val Ala Leu Val Met His Ser Leu Thr Val Thr Met Tyr Val Ile Gln
145                 150                 155                 160

Asn Met Val Arg Glu Asn Ser Phe Val Lys Ile Ile Thr Ser Phe Pro
                165                 170                 175

Ile Asp Leu Ser Glu Arg Ala Pro Val Leu Glu Arg Val Ala Asp Leu
            180                 185                 190

Cys Tyr Ser Leu Val Gly Tyr Val Trp Gly Trp Tyr His Gly Ala Thr
        195                 200                 205

Gln Leu Thr Ile Ile Val Leu Leu Arg Tyr Ala Ile Thr Glu Phe Arg
    210                 215                 220

Val Phe Leu His Ser Leu Asp Ser Leu Asp Asp Gln Leu Arg Gln Arg
225                 230                 235                 240

Arg Glu Gln Ala Gln Gly Ala Pro Asp Glu Glu Arg Ile Leu Arg Glu
                245                 250                 255

Leu Leu Tyr Glu His Ala Arg His His Ser Gln Leu Ile Val Val Val
            260                 265                 270

Thr His Leu Arg Thr Leu Leu Arg Asn Tyr Ser Leu Val His Phe Phe
        275                 280                 285

Phe Tyr Met Ile Ile Val Ala Thr Phe Met Thr Arg Val Leu Ile Ile
    290                 295                 300

Pro Gly Arg Ser Ser Phe Gly Leu Ala Ile Pro Leu Leu Thr Thr Thr
305                 310                 315                 320

Ile Tyr Phe Phe Glu Thr Phe Gly Met Cys Met Leu Val Glu Met Leu
                325                 330                 335

Val Gln Leu Asn Arg Lys Val Ser Thr Ser Leu Tyr Gly Phe Ser Trp
            340                 345                 350

Pro Gln Tyr Leu Arg Tyr Gly Arg Thr Ile Lys Arg Pro Met Met Leu
        355                 360                 365

Met Ile Met Gln Ala Asn Met Thr Lys Asp Phe Ser Ala Gly Gly Leu
    370                 375                 380

Thr Thr Val Ser Ala Glu Leu Phe Ala Lys Thr Cys Arg Met Ile Tyr
385                 390                 395                 400

Thr Met Met Met Phe Met Ala Asn Met Ala Thr
                405                 410
```

<210> SEQ ID NO 7
<211> LENGTH: 1212
<212> TYPE: DNA
<213> ORGANISM: Aedes aegypti

<400> SEQUENCE: 7

```
gtagagttag gccaatattt ccgacagcga gcgccgccaa gtcaccaaag acgaaacgaa     60

tggcgcccac ccaaaatggg agggaccggg aaaagtttct ccgggtgcag cttttgtgtc    120

ttgccctgat tggaataaag cgtcacgaaa ctgtgtcaag ccggacgatt ttccatgtct    180

gctttatctc gatggtgatc atggatttgg cgacgattct ttttgccctg gagcatgcca    240
```

acgacattgc cctcgtgtgt gactgcttgg gacccacgtt taccgcctat ctgggcatcg 300
tcaagcagta ctgtctcagt gcccatcggg tggaactgtg gaacattatc gaaacgctga 360
gacgcctcaa ggattatgct ggaattagcg aaatcgaatc aattgagcgg aacaacaaaa 420
tcgatcgatt tctggcgacg gcttatctga tgtcggcatc tgcaacggga tcactgttca 480
tcattgcggc actggctaaa ggatgttata agttgatttt tcaaaacatc atcgagtggg 540
gatttccgct ttcgttgagc tttccattca aaacgagtca tccgattgtg ttcggcatgt 600
ttttcgtctg gtccagtgcc gccatctata tagttgtatt ttgctctgta tccagtgatg 660
ccagcttcgg tggattggcc tccaatgtag ttgtccattt caaattgctc cagaaacgtt 720
tgcaggatgc cacattcgct gacaatgacg aaaatttaaa acaactcatt gaataccact 780
cgctgttgct taatttgtcg cgcaaaatta tgtcatcatt tcgtgttatt atcatcaata 840
atttattggt agcttcggta ttattatgcg ttctgggatt tcaactggtg atgtttctgg 900
gttctacact gatgctaatt tatctcatgt acgtgacggc tatcgtgatt cagatcacat 960
tttttgcata ttatggatcg cttttattgc atgagagtga agaagtcagc atttcgatct 1020
actgtagtaa ttggtacgaa gcatcaccta aaaccagacg catattgctc caatgcttga 1080
tgcgggctca agttccggta aacaccaaag caggattcat ggtagcttcc ttaccaacgt 1140
tgagagccat tcttaattca gctggctcgt acgttgcttt gcttttatca ttcactgata 1200
attaatatcc tg 1212

<210> SEQ ID NO 8
<211> LENGTH: 22
<212> TYPE: DNA
<213> ORGANISM: Artificial Sequence
<220> FEATURE:
<223> OTHER INFORMATION: A synthetic sequence

<400> SEQUENCE: 8
attggcatgc gctactttta tt 22

<210> SEQ ID NO 9
<211> LENGTH: 22
<212> TYPE: DNA
<213> ORGANISM: Artificial Sequence
<220> FEATURE:
<223> OTHER INFORMATION: A synthetic sequence

<400> SEQUENCE: 9
ataacatcct ttagccagtg cc 22

<210> SEQ ID NO 10
<211> LENGTH: 180
<212> TYPE: DNA
<213> ORGANISM: Aedes aegypti

<400> SEQUENCE: 10
cctaatttgt ttaacctttc agctggaact agcgaaatcg aatcaattga gcggaacaac 60
aaaatcgatc gatttctagc gacggcttat ctgatgtcgg catctgcaac gggatcactg 120
ttcatcattg cggcactggc taaaggatgt tataagttga tttttcaaaa catcatcgag 180

<210> SEQ ID NO 11
<211> LENGTH: 130
<212> TYPE: DNA
<213> ORGANISM: Artificial Sequence
<220> FEATURE:

-continued

```
<223> OTHER INFORMATION: A synthetic sequence

<400> SEQUENCE: 11

cctaattgcg gaacaacaaa atcgatcgat ttcggcttat ctgatgtcgg catctgcaac     60

gggatcactg ttcatcattg cggcactggc taaaggatgt tataagttga tttttcaaaa    120

catcatcgag                                                           130
```

METHODS AND COMPOSITIONS FOR IMPROVED INSECT REPELLENCY

RELATED APPLICATIONS

This application claims benefit of priority to the filing date of U.S. Provisional Application Ser. No. 63/040,918, filed Jun. 18, 2020, the contents of which are specifically incorporated herein by reference in their entirety.

GOVERNMENT FUNDING

This invention was made with government support under GM115475 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "2150746.txt" created on Jun. 17, 2021 and having a size of 24,576 bytes. The contents of the text file are incorporated by reference herein in their entirety.

BACKGROUND OF THE INVENTION

Mosquito-transmitted human diseases, such as malaria and Dengue, represent significant burdens to global human health. One of the most effective measures to reduce disease transmission involves the use of insect repellents to prevent human contact with mosquitoes.

SUMMARY

Described herein are methods for isolating compositions useful for repelling insects such as mosquitoes, ticks, or a combination thereof. The methods described herein are also useful for identifying compositions for repelling mutant and resistant insect strains as well as wild type insect strains.

For example, the methods can include: (a) contacting at least one test compound with an insect sensilla that expresses an odorant receptor 31 (Or31), an odorant receptor 53 (Or53), odorant receptor 20 (Or20), or an odorant receptor 76 (Or76) gene product; and (b) recording firing frequencies of the sensilla to thereby identify at least one test insect repellent compound. Test insect repellent compounds of interest increase the firing frequency of the insect sensilla.

In some cases the methods can include: (a) contacting a chimera ab3 sensilla that expresses a mosquito odorant receptor in an empty neuron *Drosophila melanogaster* antenna with at least one test compound; and (b) recording firing frequencies of the chimera ab3 sensilla to thereby identify at least one test insect repellent compound. The empty neuron *Drosophila melanogaster* can, for example, have a deleted endogenous odorant receptor 22a (Or22a) gene so that the Or22a odorant receptor is not expressed in the A neurons of the chimera ab3 sensilla and instead the mosquito odorant receptor is expressed in the A neurons of the chimera ab3 sensilla.

In some cases, the mosquito odorant receptors that can be used in the methods include one or more wild type or mutant odorant receptor 31. For example, the mosquito odorant receptor can be *Aedes aegypti* odorant receptor 31 (Or31), a wild type or mutant *Anopheles gambiae* odorant receptor 20 (Or20), a wild type or mutant *Anopheles gambiae* odorant receptor 31 (Or31), a wild type or mutant *Anopheles gambiae* odorant receptor 53 (Or53), a wild type or mutant *Anopheles gambiae* odorant receptor 76 (Or76), or a combination thereof.

In some cases, the method can further include applying the test insect repellent compound to a test window of a hand-in-cage apparatus and scoring the number of insects that land on the test window compared to the number of insects that land on a control window of a hand-in-cage apparatus. The insects can be wild type insects, mutant insects, or insects resistant to currently available insect repellents. The control window can, for example, be a negative control window that has no test compound and no insect repellent compounds thereon. In some cases, the control window can be a positive control window that has at least one insect repellent compounds thereon.

Compositions isolated by such methods are also described herein. For example, the composition can include at least one test insect repellent compound that exhibits increased firing frequency of an insect sensilla that expresses an odorant receptor 31 (Or31), an odorant receptor 53 (Or53), odorant receptor 20 (Or20), or an odorant receptor 76 (Or76) gene product. In some cases the odorant receptor is expressed in a chimera ab3 sensilla of an empty neuron *Drosophila melanogaster* antenna and the firing frequencies of the chimera ab3 sensilla are recorded to thereby identify the at least one test insect repellent compound. The test insect repellent compound included in the compositions can increase the firing frequency of a wild type or mutant insect sensillas odorant receptors The compositions and methods can in some cases include one or more activators of odorant receptors and one or more activator of voltage-gated sodium channels. Examples of activators of odorant receptors include farnesene, (±)-lavandulol, (−)-borneol, (−)-α-thujone, norcamphor, camphor, eucalyptol, (+)-fenchone, prenol, indole, guaiacol, 1-octen-3-ol, isoamyl acetate, geranyl acetate, (±)-citronellal, isoamyl alcohol, toluene, sulcatone, citral, bioallethrin, or a combination thereof. Examples of activators of voltage-gated sodium channels include one or more pyrethrins.

Also described herein are methods for repelling insects that involve distributing or applying the compositions described herein to an area or entity (e.g., an animal or human) in need thereof.

DESCRIPTION OF THE FIGURES

FIG. 1A shows an image and a schematic diagram of the setup for the hand-in-cage repellency assay similar to that described by Boyle et al. (bioRxiv, 060178 (2016)). FIG. 1B graphically illustrates dose-dependent pyrethrum repellency in ROCK (wild-type) mosquitoes (n=7 cages for control; n=9 cages for $10^{-3}$ (v/v); n=8 cages for $10^{-2}$ (v/v) when evaluating 3 batches of ROCK (wild-type) mosquitoes; t=2.68, df=14 for control vs. pyrethrum at $10^{-3}$ and t=9.58, df=13 for control vs. pyrethrum at $10^{-2}$). FIG. 1C graphically illustrates repellency of pyrethrum ($10^{-2}$ v/v) against Orlando (wild-type) or orco$^{-/-}$ mutant mosquitoes (n=6 cages for each of the controls; n=8 cages for pyrethrum at the $10^{-2}$ dilution in Orlando, n=7 cages for pyrethrum at $10^{-2}$ in orco$^{-/-}$, data are from 3 batches of mosquitoes; t=11.74, df=12 for control vs. pyrethrum at $10^{-2}$ in Orlando, U=3 for control vs. pyrethrum at $10^{-2}$ in orco$^{-/-}$, and t=6.53, df=13 for Orlando vs. orco$^{-/-}$ at $10^{-2}$ of pyrethrum. Data are plotted as mean±s.e.m and dots denote the value of each repeat. Two-tailed unpaired student's t-test or two-tailed Mann-Whitney Rank Sum test was used to compare each of two sets of data. Exact P-value are indicated for each comparison in the figure. The control for each mosquito line represents the baseline activity in the absence of a test compound. FIG. 1D graphically illustrates pyrethrum repellency against *An. gambiae* Kisumu mosquitoes, where n=2 cages at the $10^{-3}$ dilution (v/v); and n=4 cages at the $10^{-2}$ dilution (v/v) from one batch of mosquitoes. Data in FIG. 1D are plotted as mean±s.e.m. and dots denote the value of each repeat.

FIG. 2A is a schematic diagram illustrating methods for obtaining single sensillum recordings (SSR) from *Ae. aegypti* mosquito antennae. FIG. 2O graphically illustrates odorant responses to different compounds by AgOr31 (n=3 sensilla) when expressed in *Drosophila* ab3A empty neurons. Data are plotted as mean±s.e.m.

FIG. 3A-3G illustrate AaOr31-mediated (E)-β-farnesene (EBF)/pyrethrum repellency in *Ae. aegypti*. FIG. 3A shows representative single sensillum recording traces from sbt-1 sensilla in response to (E)-β-farnesene (EBF, representative response from n=10 sensilla for ROCK and n=7 sensilla for AaOr31$^{-/-}$), (±)-citronellal (representative response from n=10 sensilla for ROCK and n=8 sensilla for AaOr31$^{-/-}$), geranyl acetate (representative response from n=10 sensilla for ROCK and from n=8 sensilla for AaOr31$^{-/-}$) and pyrethrum (representative response from n=10 sensilla for ROCK and n=8 sensilla for AaOr31$^{-/-}$) at $10^{-2}$ dilution. FIG. 3B graphically illustrates repellency in AaOr31$^{-/-}$ compared with that of ROCK (wild-type) mosquitoes to (E)-β-farnesene (t=3.38, df=11, n=6 cages for the AaOr31$^{-/-}$ and n=7 cages for the ROCK from 3 batches of mosquitoes), (±)-citronellal (t=2.26, df 16, n=9 cages for AaOr31$^{-/-}$ and 9 cages for ROCK from 4 batches of mosquitoes), geranyl acetate (U=8, n=8 cages for ROCK, n=9 cages for AaOr31−/− from 4 batches of mosquitoes) and pyrethrum (U=1, n=6 cages for AaOr31−/−, n=8 cages for ROCK from 3 batches of mosquitoes) at $10^{-2}$ dilution. Data are plotted as mean±s.e.m. and dots denote the value of each repeat. Two-tailed unpaired student's t-test or two-tailed Mann-Whitney Rank Sum test was used to compare each of two sets 5 of data. Exact P-value are indicated for each comparison in the figure. FIG. 3C graphically illustrates olfactory responses to pyrethrum by AgOrs expressed in the *Drosophila* empty neuron (ab3A) model. The responses of ab3A neurons expressing each of 50 AgOrs to pyrethrum are shown. Four AgOrs (AgOr31, AgOr20, AgOr53 and AgOr76) were activated significantly (Δ spikes/s>20) by pyrethrum at the $10^{-2}$ dilution as shown in the inset (n=3 for AgOr20; n=6 for AgOr53 and AgOr76; n=8 for AgOr31). FIG. 3D shows sequence comparison (amino acid sequence identity) of odorant receptors from various mosquito species where the Or31 orthologs are found in *Aedes, Culex* and *Anopheles* mosquito species. As illustrated, the Or31 orthologs from these sequences have at least 40% amino acid sequence identity. FIG. 3E illustrates (E)-β-farnesene activation of *Drosophila* ab3A empty neurons expressing AgOr31 (from n=5 sensilla). FIG. 3F graphically illustrates activation of *Drosophila* ab3A empty neurons expressing AgOr31 by each one of the indicated compounds, including six insecticidal esters, ethyl palmitate, and ethyl linoleate (n=5 sensilla). FIG. 3G shows an alignment of exon 2 (gray shade) and upstream intron sequences of AaOr31 between ROCK (wild-type, top; SEQ ID NO:10) and mutant AaOr31$^{-/-}$ (bottom, SEQ ID NO:11) strains. Sequences underlined were used in designing two single guide RNAs for CRISPR-Cas9. Two deletions in exon 2 of AaOr31$^{-/-}$ are indicated and shown as dashed lines.

FIG. 4A shows a diagram of a ROCK mosquito sensillum and representative single ROCK mosquito sensillum recording traces of sst-1 sensilla responding to pyrethrin I (P-I) (from n=8 sensilla) and pyrethrin II (P-II) (from n=6 sensilla) at the $10^{-1}$ dilution. FIG. 4B graphically illustrates repellency elicited by pyrethrin I (P-I) and pyrethrin II (P-II) at $10^{-3}$ dilution in Orlando (wild-type) and orco$^{-/-}$ mosquitoes (n=9 cages for Orlando control from 2 batches of mosquitoes; n=10 cages for orco−/− control from 2 batches of mosquitoes, P-I: U=31, n=11 cages for Orlando; and n=12 cages for orco−/− from 3 batches of mosquitoes, P-II: U=15; n=14 cages for Orlando; and n=15 cages for orco−/− from 4 batches of mosquitoes). As illustrated, the wild type Orlando mosquitoes exhibited greater repellency than the orco$^{-/-}$ mutant mosquitoes. Orco is an obligate olfactory co-receptor that forms a complex with all ligand-selective odorant receptors and is required for efficient trafficking to olfactory sensory neuron dendrites. FIG. 4C graphically illustrates reduced pyrethrum repellency in pyrethrum/pyrethroid resistant KDR:ROCK mosquitoes compared to the pyrethrum repellency observed in ROCK (wild-type) mosquitoes (n=10 cages for control ROCK and n=9 cages for control KDR:ROCK from 2 batches of mosquitoes; at the $10^{-3}$ dilution: t=2.96, df=28, n=15 cages for ROCK and n=15 cages for KDR:ROCK from 4 batches of mosquitoes; at the $10^{-2}$ dilution: t=6.56, df=31, n=17 cages for ROCK and n=16 cages for KDR:ROCK from 4 batches of mosquitoes). FIG. 4D graphically illustrates the effect of (E)-β-farnesene (4 ppm) upon P-I (1000 ppm), P-II (1000 ppm), and (−)-borneol (100 ppm) repellency in ROCK and/or AaOr31$^{-/-}$ mosquitoes (n=10 cages for each of the controls from 2 batches of mosquitoes; ROCK: U=6, n=8 cages for P-I+EBF and n=12 cages for P-I alone from 3 batches of mosquitoes; t=3.82, df=16, n=10 cages for P-II alone and n=8 cages for P-II+EBF from 3 batches of mosquitoes; and t=0.49, df=21, n=13 cages for (−)-borneol alone and n=10 cages for (−)-borneol+EBF from 3 batches of mosquitoes; and $AaOr31^{-/-}$: t=0.11, df=14, n=8 cages for P-II alone and n=8 for P-II+EBF from 2 batches of mosquitoes). FIG. 4E graphically illustrates the effects of (E)-β-farnesene (EBF; 10 ppm) on repellency by P-I (1 ppm and 10 ppm) in ROCK (n=10 cages for control; P-I at the $10^{-6}$ dilution: t=7.34, df=18, n=10 for P-I alone and n=10 for P-I+EBF from 2 batches of mosquitoes; P-I at 1 ppm: t=3.32, df=18, n=10 cages for P-I alone and n=10 cages for P-I+EBF from 2 batches of mosquitoes). EBF alone at 4 ppm and 10 ppm did not elicit repellency in ROCK or $AaOr31^{-/-}$ mosquitoes (FIG. 4H). Data are plotted as mean±s.e.m. and dots denote the value of each repeat. Two-tailed unpaired student's t-test or two-tailed Mann-Whitney Rank Sum test was used to compare each of two sets of data. Exact P-value are indicated for each comparison in the figure. The control for each mosquito line represents the baseline activity in the absence of a test compound. FIG. 4F-4G illustrate the effects of kdr mutations on the sensitivity of mosquito sodium channels and pyrethrum repellency. FIG. 4F shows that two kdr mutations, S989P and V1016G, in the mosquito sodium channel (AaNav1-1) conferred AaNav1-1 channel resistance to pyrethrum. t=9.8, df=8, n=5 for ROCK AaNav1-1 and n=5 for KDR:ROCK AaNav1-1. AaNav1-1 wild type and the mutant channel carrying the double mutations were expressed in *Xenopus* oocytes and channel sensitivity to pyrethrum was examined using the two-electrode voltage clamp technique (Du et al. Proc. Natl. Acad. Sci. USA 110: 11785-11790 (2013)). The effect of pyrethrum was measured 10 minutes after its application. Pyrethrum-induced tail currents were recorded during a 100-pulse train of 5 milliseconds step depolarizations from −120 to −10 mV with 5 milliseconds inter-pulse intervals (Du et al. (2013)). The percentage of pyrethrum-modified channels was calculated using the following equation: $M=[I_{tail}/(E_h-E_{Na})]/[I_{Na}/(E_t-E_{Na})]\times100$; where $I_{tail}$ is the maximal tail current amplitude, $E_h$ is the potential to which the membrane is repolarized, $E_{Na}$ is the reversal potential for sodium currents determined from the current-voltage curve, $I_{Na}$ is the amplitude of the peak current during depolarization before pyrethrum exposure, and $E_t$ is the potential of the step depolarization. FIG. 4G graphically illustrates reduced pyrethrin repellency in pyrethrum/pyrethroid resistant KDR:ROCK mosquitoes compared to that in ROCK (wild type) mosquitoes. P-I: t=3.78, df=23, n=12 cages for ROCK and n=13 cages for KDR:ROCK from 3 batches of mosquitoes; P-II: t=3.97, df=11, n=10 cages for and n=3 cages for KDR:ROCK from 2 batches of mosquitoes. Data are plotted as mean±s.e.m. and dots denote the value of each repeat. Two-tailed unpaired student's t-test was used to compare each of two sets of data. Exact P-value are indicated for each comparison in the figure. FIG. 4H-4J illustrate repellency by (E)-β-farnesene (EBF) and (−)-borneol. FIG. 4H graphically illustrates that (E)-β-farnesene (EBF) elicited no repellency at 1000 ppm or lower concentrations. ROCK: n=8 cages for 4 ppm, n=10 cages for 10 ppm, n=3 cages for 1000 ppm, from 2 batches of mosquitoes; $AaOR31^{-/-}$: n=10 cages for 4 ppm from 2 batches of mosquitoes. FIG. 4I graphically illustrates repellency by (−)-borneol (at the $10^{-2}$ dilution) is Orco-mediated. t=6.64, df=9, 5 n=6 cages for Orlando and n=5 cages for orco−/− from 3 batches of mosquitoes. FIG. 4J shows that there is no effect of (−)-borneol on sodium channel gating. Sodium current recording traces were obtained from AaNav1-1 channels expressed in *Xenopus* oocytes in response to 20 ms step-depolarization before and after exposed (−)-borneol (from n=5 oocytes from two separated batches). (−)-Borneol had no effects on peak current and channel gating. Data are plotted as mean±s.e.m. and dots denote the value of each 10 repeat. Two-tailed unpaired student's t-test was used to compare the two sets of data. The exact P-value is indicated in the figure.

DETAILED DESCRIPTION

Described herein are methods for isolating new insect repellents. Also described herein are compositions and methods for repelling insects, including mosquitoes and ticks. The compositions and methods involve use of one or more activators of sst and/or sbt olfactory receptor neurons, one or more activators of voltage-gated sodium channels, or a combination thereof.

As shown herein, some components of pyrethrum exert insect repellency through a multi-target mechanism.

Insect olfactory receptors are mainly expressed in olfactory receptor neurons (ORNs) in the insect's antenna. Three major morphologically distinct types of antennal trichodae sensilla are recognized in *Ae. aegypti* antennae: short sharp-tipped (sst), long sharp-tipped (lst), and short blunt-tipped (sbt). Each *Ae. aegypti* sensillum houses two neurons. The neuron that generates larger spikes (i.e., action potentials) is called the A neuron and the neuron that produces smaller spikes is called the B neuron.

As described herein three responsive sst-type sensilla (sst-1, sst-2, and sst-3) and six three responsive sbt-type sensilla (sbt-1, sbt-2, sbt-3, sbt-4, sbt-5 and sbt-6) can be activated by various compounds and compositions described herein. Various compounds can be isolated and/or identified by evaluating whether those compounds activate specific olfactory receptor neurons in adult antennae and elicit odorant receptor (Or)-mediated repellency in insects such as mosquitoes (*Aedes aegypti*).

Methods of Isolating Compounds that can Repel Insects

Figure 3A:
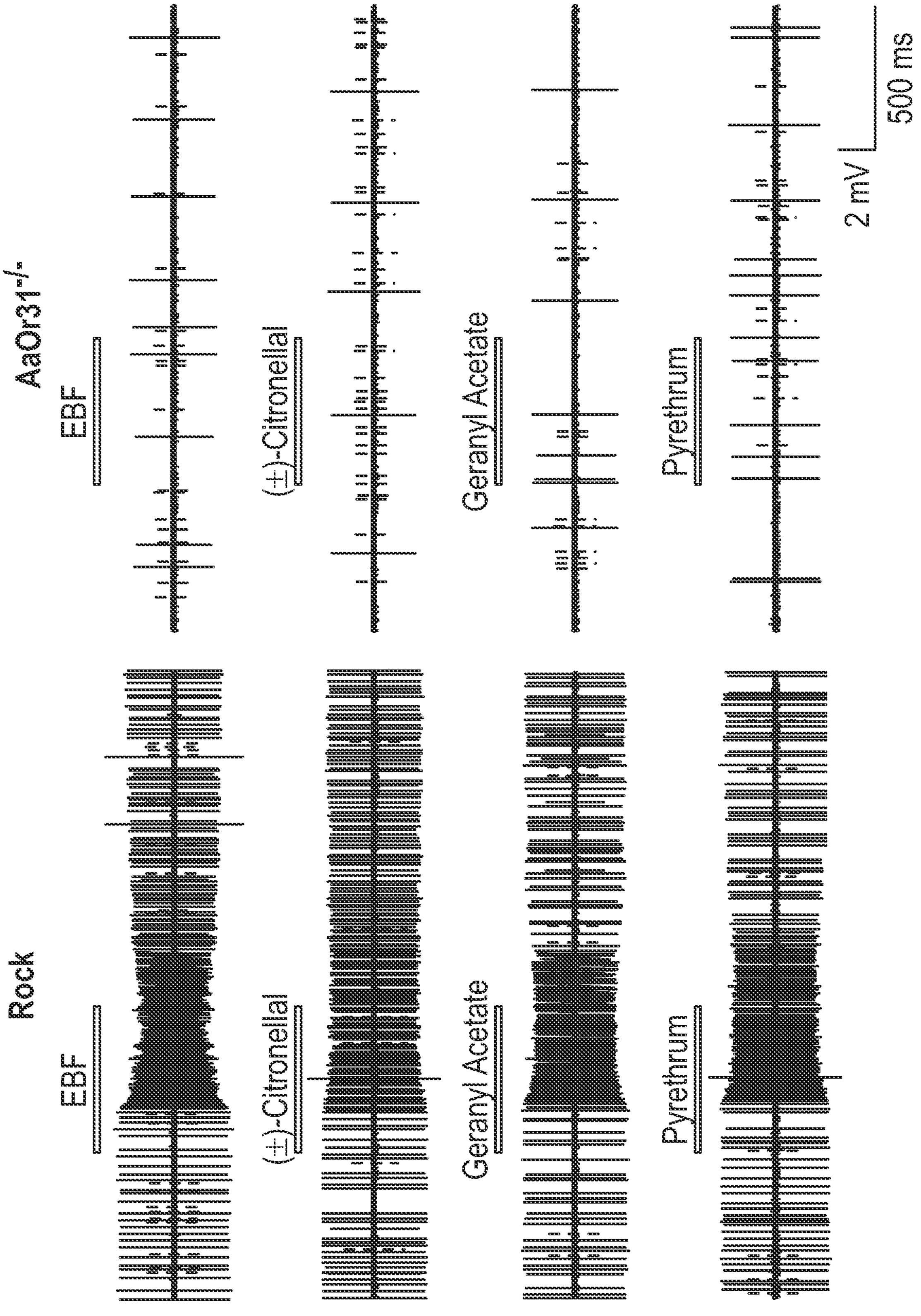

As described herein, specific odorant receptors from mosquitoes are activated when the mosquitoes are repelled by pyrethrums. Methods are described herein for isolating new types of insect repellents that involve testing whether an odorant receptor is activated. For example, as illustrated herein, odorant receptors Or20, Or31, Or53, and Or76 from Ae. *aegypti* is activated by pyrethrum (FIG. 3C).

The inventors have identified the odorant receptor, Or31 as a mediator of repellency (see Examples). Or31 is conserved in all major human disease-transmitting mosquito species including *Anopheles gambiae*, a primary vector of human malaria; *Aedes aegypti*, the primary mosquito vector of dengue, yellow fever, Zika and chikungunya; *Culex quinquefasciatus*, a primary vector of West Nile virus; *Aedes albopictus*, another major vector of dengue and West Nile virus, and other *Anopheles* species. The inventors believe that Or31 is the first cross-species mosquito odorant receptor that has been identified for mediating repellency in mosquitoes. The Example illustrates that Or31 can be used as a target for isolating a new generation of durable and wide-spectrum insect repellent.

The *Drosophila* empty neuron system can be used and coupled with single sensillum recording (SSR). Alternatively, the *Xenopus* oocyte expression system coupled with two-electrode voltage clamp can be used. Such methods can be used to screen chemical libraries for compounds that can activate Or31.

Briefly, in this empty neuron system, the endogenous Or gene Or22a is deleted and replaced with another insect (e.g. mosquito) Or31, so that a heterologous Or31 gene is expressed in the A neurons of ab3 sensilla.

Single sensillum recording (SSR) of the chimera ab3 sensilla that is expressing the mosquito Or31 in *D. melanogaster* antennae can be used to examine the activity of the ab3 sensilla. If a compound activates Or31, an increase in firing frequency of ab3 sensilla is detected in response to the compound.

For expression of Or31 in *Xenopus* oocytes, in vitro synthesized cRNA of Or31 will be injected into oocytes. Activation of Or31 by a given compound can be detected using two electrode voltage clamp technique.

Both assays are robust and established to work by the inventors. Over 100 compounds can be screened daily using either method.

An example of an odorant receptor that can be used to isolate new insect repellent compounds is the odorant receptor 31 (Or31) from *Aedes aegypti*, the yellow fever mosquito. The following sequence is an example of such an *Aedes aegypti* Or31 (NCBI accession no. NP_001345089 XP_001663400), provided herein as SEQ ID NO:1.

```
  1 MAPTQNGRDR EKFLRVQLLC LALIGIKRHE TVSSRTIFHV
 41 CFISMVIMDL ATILFALEHA NDIALVCDCL GPTFTAYLGI
 81 VKQYCLSAHR VELWNIIETL RRLKDYAGIS EIESIERNNK
121 IDRFLATAYL MSASATGSLF IIAALAKGCY KLIFQNIIEW
161 GFPLSLSFPF KTSHPIVFGM FFVWSSAAIY IVVFCSVSSD
201 ASFGGLASNV VVHFKLLQKR LQDATFADND ENLKQLIEYH
241 SLLLNLSRKI MSSFRVIIIN NLLVASVLLC VLGFQLVMFL
281 GSTLMLIYLM YVTAIVIQIT FFAYYGSLLL HESEEVSISI
321 YCSNWYEASP KTRRILLQCL MRAQVPVNTK AGFMVASLPT
361 LRAILNSAGS YVALLLSFTD N
```

Another example of an *Aedes aegypti* Or31 (NCBI accession no. DAA80377.1) is provided herein as SEQ ID NO:2.

```
  1 MAPTQNGRDR EKFLRVQLLC LALIGIKRHE TVSSRTIFHV
 41 CFISMVIMDL ATILFALEHA NDIALVCDCL GPTFTAYLGI
 81 VKQYCLSAHR VELWNIIETL RRLKDYAGTS EIESIERNNK
121 IDRFLATAYL MSASATGSLF IIAALAKGCY KLIFQNIIEW
161 GFPLSLSFPF KTSHPIVFGV FFVWSSAAIY IVVFCSVSSD
201 ASFGGLASNV VVHFKLLQKR LQDATFADND ENLKQLIEYH
241 SLLLNLSRKI MSSFRVIIIN NLLVASVLLC VLGFQLVMFL
281 GSTLMLIYLM YVTAIVIQIT FFAYYGSLLS HESEEVSSSI
321 YCSNWYEASP KTRRILLQCL MRAQVPVNTK AGFMVASLPT
361 LRAILNSAGS YVALLLSFTD N
```

Another example of an odorant receptor that can be used to isolate new insect repellent compounds is the odorant receptor 20 (Or20) from *Anopheles gambiae*, which includes at least seven morphologically indistinguishable species of mosquitoes that are some of most important vectors of malaria in sub-Saharan Africa. The following sequence is an example of such an *Anopheles gambiae* Or20, provided herein as SEQ ID NO:3.

```
  1 MLRLSPEDPK AVMPFAKRLL RLSGFRQETE QLEKQIFFNL
 41 FVYVAALLIP KVCSPYPDSE AIIRGLSELI FFTNVYVGYY
 81 CFVVQHRHYR DLLDEIQSFV NVVYPTSQQP ESPSERTLIK
121 LNVKINKISV LYCWYLAAAG LIYWSTPCLM TYHSVLKAKA
161 EYGPNHPIRF YPNLEGSFYG LDNRTSVYGY AAFSIVALLV
201 FAFASYNNAT KLLTILSTIK YCSTLLQLVG VEVDNLNHTS
241 SEAIGRELKK VIQLHQLALR CVALLNQTLS FVMALQLALC
281 ILTWCFTLLY ILIVGFNAIA TNGLLIMINM TLEMFGYCFF
321 CTELDTTGKI VSRQMYEFRW EQHRPTVQKM VAMIIARSQT
361 PLQITACGFI PINLELFTKV VKHSYTVLAV LKDLI
```

Another example of an odorant receptor that can be used to isolate new insect repellent compounds is the odorant receptor 31 (Or31) from *Anopheles gambiae* is shown below as SEQ ID NO:4

```
  1 MLAAETVDFF RVQSICLRAI GIARTDSFRG RVLFAVSFFT
 41 VLVMMLGTVM FAFKHIDQIM LLCDCLGPTF TAYLGLVRQY
 81 NLLLHRSELW SIVDEFAALK HSLQSSEIRI VQKYNRIDRF
121 LAWAYLITAM STGVLFVGVA LVLVFLSEKS DWKLPLLMDF
161 PFDVKHPVTF TIFFVWCSVA IFWVVLDCVA CDSTFGTFSS
201 CLVAHFVIIQ ERFEGLRFDD GNRELKKLIE HHKYILRISD
241 RVINAYKNVI LNQLLISSVL LCMLGFQLVI SVGTNIMVVY
281 VAYGMAITIQ VTYYCYYGSQ LYYESTQVHD AVFKSKWYDA
321 SVATQKMLIN CMMRAKKPVN AKSGFTQASL PTLNAILNSA
361 GSYVALLMSL ME
```

Another example of an odorant receptor that can be used to isolate new insect repellent compounds is the odorant receptor 53 (Or53) from *Anopheles gambiae* is shown below as SEQ ID NO:5.

```
  1 MKLLELDNPR EAIAIGCRLL KLFGLGRDER FKLVYWLQCV
 41 AYLAFSIVPR LLVEIEDMVA LMRLIAELVF VVYLCLQIMA
 81 LYCRRRQLYR LVDMLQQCID IPYSEQIESF LIRSNVKINQ
121 SSAAYARFFM CVYVLYCTMS PLASGFVYIR NQRNATGVQE
161 DLYDLDIRYN PLHYSIYAGL IFVLSAISSL SLCTKDVIDI
201 AAIKTVTLVF GIVTMQIRDL HEQITQERLN RVIKSHSNAL
241 SCATQLEQAL NLSVLFQFAS CSAIWCLMLF YILLMGLDSR
281 VLSVVLLLVI VSIETYAYCM LGSQLTTQGE DLLMALQQLS
321 WYDQPVPIQR QILLMIRRSQ TPLILRAGKL FSANVVQFGD
361 IVQKSYSFFL VLKNVF
```

Another example of an odorant receptor that can be used to isolate new insect repellent compounds is the odorant receptor 76 (Or76) from *Anopheles gambiae* is shown below as SEQ ID NO:6.

```
  1 MTVVHRIVSF GYNLLQRHFN VGHPTEQFFL LRCLDVVSPA
 41 MLLQRPRSNL EVALKTLCLS VMVAHTIALA YDFSQQMDVR
 81 LALDMLCMLS LFVSIILRST CMRQYLSHID ALDRLERRPT
121 FRVGTPYADE SRRNVALQNS RYLGVALVMH SLTVTMYVIQ
161 NMVRENSFVK IITSFPIDLS ERAPVLERVA DLCYSLVGYV
201 WGWYHGATQL TIIVLLRYAI TEFRVFLHSL DSLDDQLRQR
241 REQAQGAPDE ERILRELLYE HARHHSQLIV VVTHLRTLLR
281 NYSLVHFFFY MIIVATFMTR VLIIPGRSSF GLAIPLLTTT
321 IYFFETFGMC MLVEMLVQLN RKVSTSLYGF SWPQYLRYGR
361 TIKRPMMLMI MQANMTKDFS AGGLTTVSAE LFAKTCRMIY
401 TMMMFMANMA T
```

For example, a selected odorant receptor can be expressed in in the "ab3 empty neuron" system of *Drosophila melanogaster* (Carey et al. *Nature* 464, 66-71 (2010); Dobritsa et al. Neuron 37:827-41 (2003); Hallem et al. Cell 117:965-79 (2004), which documents are specifically incorporated by reference herein in their entireties). In the "ab3 empty neuron" system of *Drosophila melanogaster* the endogenous odorant receptor gene, Or22a, in the ab3 sensillum was deleted. Activation of an odorant receptor that is expressed in this *Drosophila* strain can be detected by single sensillum recordings (SSR).

Activators of Odorant Receptors

A variety of test compounds can be evaluated by the methods described herein to ascertain if those compounds are effective activators of odorant receptors.

Activators of odorant receptors described herein can activate sst and/or sbt olfactory receptor neuron. In some cases, the odorant is an activator of odorant receptor 31 (Or31). The activator of odorant receptor 31 (Or31) is expressed in various olfactory receptor neurons, including in the sst-1A neuron.

Examples of activators of odorant receptors include one or more of (E)-β-farnesene, (±)-lavandulol, (−)-borneol, (−)-α-thujone, norcamphor, camphor, eucalyptol, (+)-fenchone, prenol, indole, guaiacol, 1-octen-3-ol, isoamyl acetate, geranyl acetate, (±)-citronellal, isoamyl alcohol, toluene, sulcatone, citral, bioallethrin, or a combination thereof. The compositions described herein for repelling insects can include one, two, three, four, five, six, seven, eight, nine, ten, or more activators of odorant receptors. In some cases, the compositions for repelling insects include just one activator of one or more odorant receptors.

Structures of some of these activators of odorant receptors are shown below.

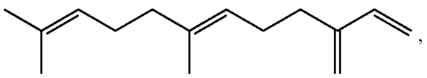, (E)-Beta-Farnesene

-continued

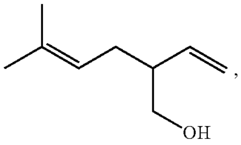,

Lavandulol

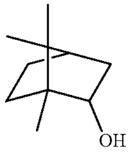,

Borneol

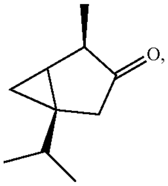

(-)-Alpha-Thujone

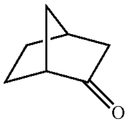,

Norcamphor

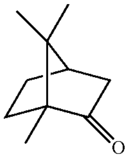,

Camphor

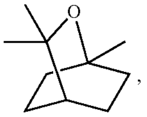,

Eucalyptol

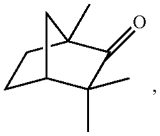,

Fenchone

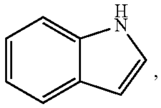,

Indole

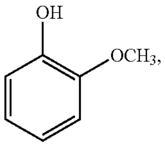

Guaiacol

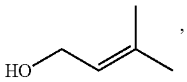,

Prenol

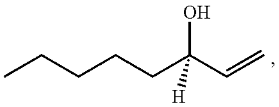,

1-Octen-3-ol

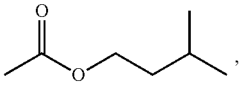,

Isoamyl acetate

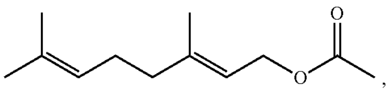,

Geranyl acetate

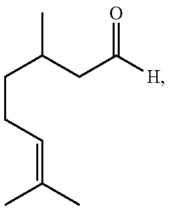

Citronellal

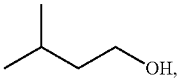

Isoamyl alcohol

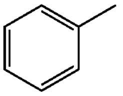,

Toluene

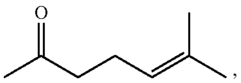,

Sulcatone

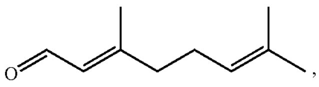,

Citral or a combination thereof.

In some cases, the activators of odorant receptors can be a compound of formula I:

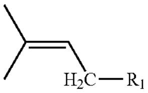

I where $R_1$ is a $C_4$-$C_8$ alkenylene or $C_4$-$C_8$ alkylene, where the alkenylene or alkylene can be substituted with 1-3 groups, each group separately being a methyl ($CH_3$ or $CH_2$), oxy, acetate (—O—CO—$CH_3$).

Activators of Voltage-Gated Sodium Channels

Various compounds described herein can activate voltage-gated sodium channels. voltage-gated sodium channels transmembrane proteins that are responsible for the rapid depolarization that underlies the upstroke of action potentials in neurons and are thus crucial to nerve impulse conduction.

Examples of compounds that can activate voltage-gated sodium channels include one or more pyrethrin, allethrin, bifenthrin, cyfluthrin, cypermethrin, cyphenothrin, deltamethrin, esfenvalerate, etofenprox, fenpropathrin, fenvalerate, flucythrinate, flumethrin, imiprothrin, lambda-cyhalothrin, metofluthrin, permethrin, resmethrin, silafluofen, sumithrin, tau-fluvalinate, tefluthrin, tetramethrin, tralomethrin, transfluthrin, or a combination thereof. The compositions described herein for repelling insects can include one, two, three, four, five, six, seven, eight, nine, ten, or more activators of voltage-gated sodium channels. In some cases, the compositions for repelling insects include just one activator of one or more voltage-gated sodium channels.

Pyrethrins are botanical insecticides derived from *chrysanthemum* flowers. In some cases, the pyrethrin can have the structure shown in formula II, where the R group can be methyl or $CO_2CH_3$.

II

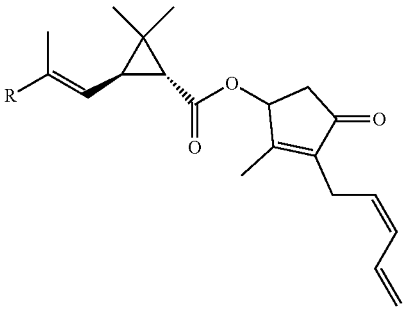

When R is methyl, the compound is pyrethrin I (P-I), but when R is $CO_2CH_3$, the compound is pyrethrin II (P-II).

In some cases, pyrethroids can be used in the compositions. Pyrethroids are synthetic chemical insecticides whose chemical structures are adapted from the chemical structures of the pyrethrins and act in a similar manner to pyrethrins. Examples of compounds that can be used in the compositions include any of the following. Many of these compounds are pyrethroids.

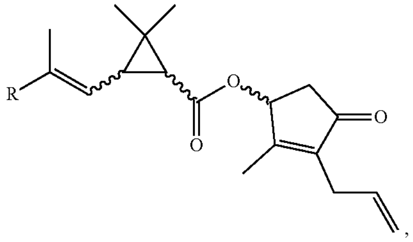

Allethin

-continued

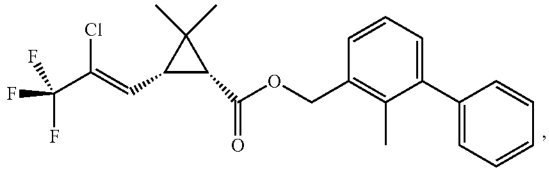

Bifenthrin

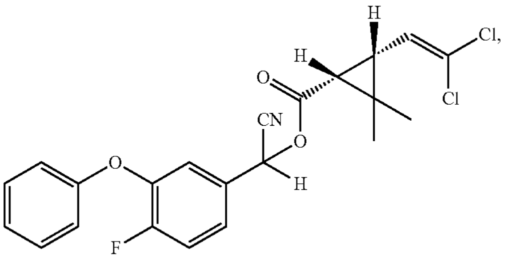

Cyfluthrin

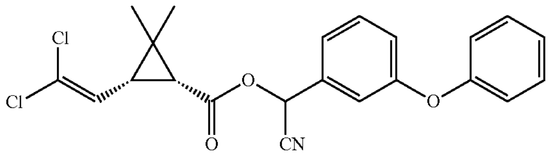

Cypermethrin

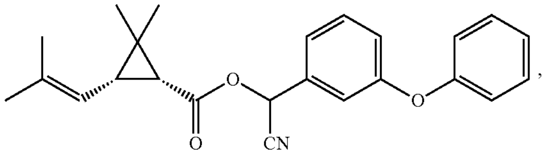

Cyphenothrin

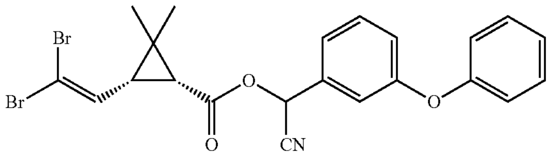

Deltamethrin

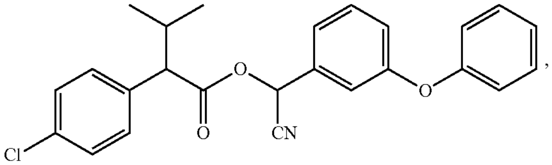

Esfenvalerate or Fenvalerate

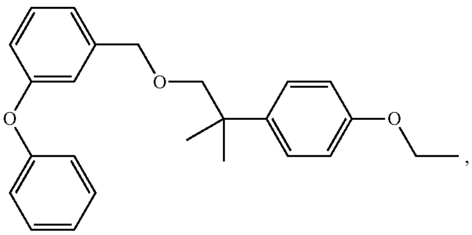

Etofenprox

-continued
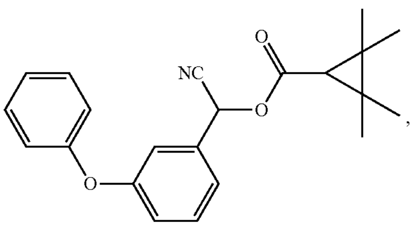
Fenpropathrin
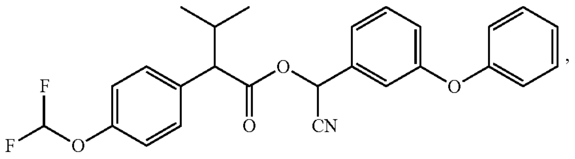
Flucythrinate
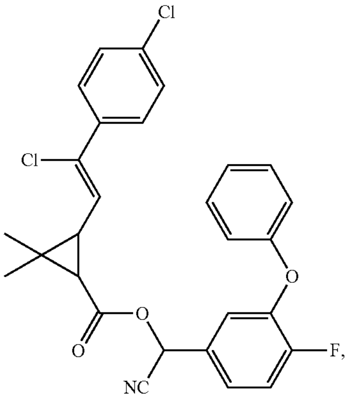
Flumethrin
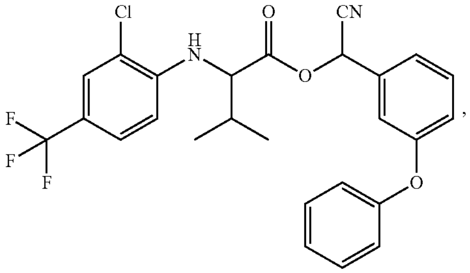
Fluvalinate
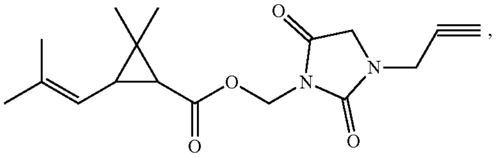
Imiprothrin
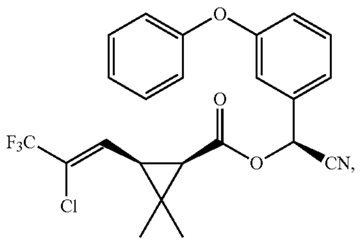
Lambda-cyhalothrin
-continued
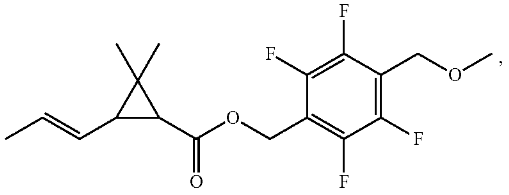
Metofluthrin
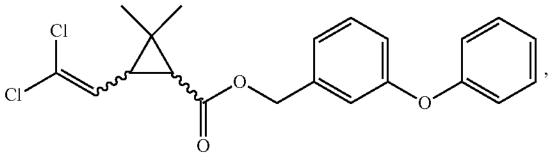
Permethrin
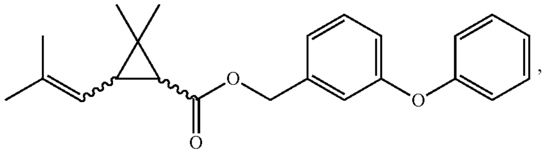
Phenothrin
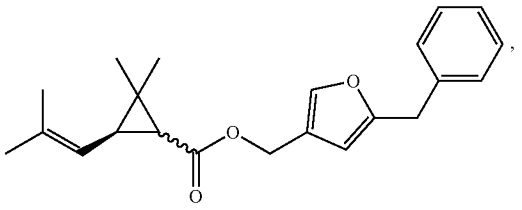
Resmethrin
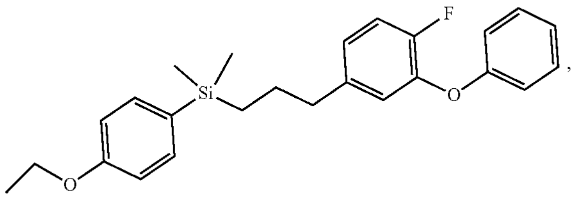
Silafluofen
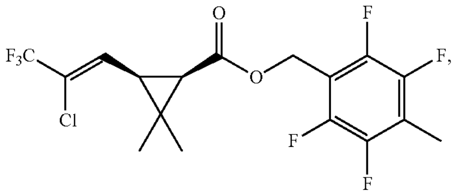
Tefluthrin
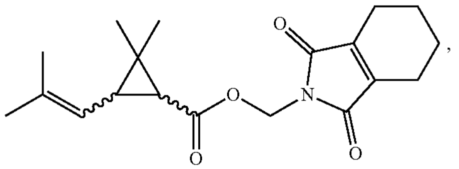
Tetramethrin
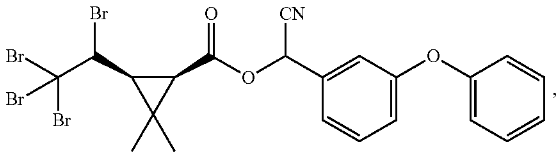
Tralomethrin -continued

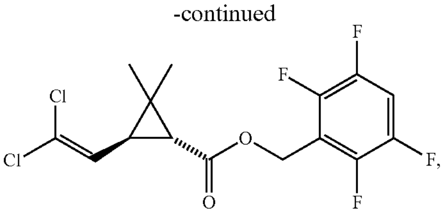

Transfluthrin or a combination thereof.

(E)-β-farnesene (EBF), a minor component of pyrethrum, elicited repellency by odorant receptor 31 (Or31) expressed in another olfactory receptor neuron, sst-1A. Pyrethrum repellency was compromised in Or31-knockout mutant as well as in a sodium channel mutant that confers pyrethrum resistance, demonstrating a dual mechanism of pyrethrum repellency involving Or31 and sodium channels. The methods described herein can be used to identify other types of compounds useful for repelling insects that exhibit reduced responses to currently available insect repellents.

Surprisingly however, pyrethrins and (E)-β-farnesene exhibit significant synergism in repellency. The results described herein indicate that simultaneous activation of sst-1A and sbt-1A olfactory pathways and voltage-gated sodium channels by pyrethrins and (E)-β-farnesene provide highly durable and broad-spectrum repellency against mosquitoes and other insects. Discovery of this multi-target mechanism provides improves compositions and methods for repelling major human-disease-transmitting insect vectors.

Treatment

The compounds and compositions described herein can be used as insect repellents for treatment of animals, including humans, domesticated animals, zoo animals, and wild animals. Compositions containing unique combinations of compounds can be designed using the methods described herein to target insects that are resistant to currently available insect repellents. A method can be employed that includes administering or applying any of the compounds or compositions described herein to one or more animals (e.g., one of more human).

The compounds and compositions described herein can be employed for repelling insects such as mosquitoes, ticks, or a combination thereof. The compounds and compositions can be used to repel wild type, mutant, and resistant strains of insects. The compounds or compositions described herein may be applied to animals, to solid surfaces, to wetlands, to brush, to woodlands, and the like.

Application of compounds or compositions can be carried out directly, or by action on their environment, habitat or storage area. Application (or treatment) methods include, for example, topical application to an animal. Application (or treatment) methods can also include, for example, spraying, atomizing, broadcasting, dusting, foaming, spreading-on, brushing on, and combinations thereof. Structures, lawns, surfaces, and/or animals can be treated by powdering, spraying, mixing, encrusting, or a combination thereof. The compositions can be applied in dry or liquid form.

The compounds described herein can also be applied to structures (e.g., houses, barns, sheds, warehouses, basements, attics, etc.) where insects can be present. For example, the compounds described herein can be applied to areas suspected of having insects such as mosquitoes or ticks. Examples of areas where the compounds and/or compositions can be applied include animals (e.g., humans), barns, lawns, gardens, animal pens, decks, boat surfaces, and the like.

An effective amount is an amount sufficient to repel insects by at least about 5%, 10%, 20%, 25%, 30%, 40%, 50%, 60%, 70%, 75%, 80%, 85%, 90%, 93%, 94%, 95%, 96%, 97%, 98%, 99%, 99.5%, or 99.9%.

For example, in some cases the compounds described herein can each be distributed or applied at a concentration of about 0.1 ppm to 500 ppm, or about 1 ppm to 400 ppm, or about 2 ppm to 300 ppm, or about 5 ppm to 250 ppm, or about 10 ppm to 150 ppm, or about 12 ppm to 100 ppm, or about 15 to 50 ppm, or about 20 ppm to 35 ppm, or about 25 ppm.

In some instances, the compounds and/or compositions are provided as concentrated formulation that are diluted ten-fold, 100-fold, or 1000-fold to provide a concentration that is applied or administered to animals, structures, walls, floors, ceilings, containers, plants, seeds, and/or plant products.

The period of time within which protection is effective generally extends from 1 to 90 days, from 1 to 80 days, from 1 to 70 days, from 1 to 60 days, from 1 to 45 days, from 1 to 30 days, from 1 to 14 days, or from 1 to 7 days, after application of the compounds and/or compositions described herein.

The compositions described herein can include at least one compound described herein and at least one carrier. The compositions described herein can be used to repel insects such as mosquitoes, ticks, or a combination thereof. The compositions can optionally include one or more antibacterial or other antifungal agents.

To prepare the composition, the compounds are synthesized or otherwise obtained, and purified as necessary or desired. These compounds can then be lyophilized or stabilized, for example, if storage is desirable. The compounds can be combined with a carrier such as a solvent or diluent. The concentrations of the compounds can be evaluated and adjusted to an appropriate amount, and the compounds can optionally be combined with other agents.

In general, the compositions contain an amount of at least one of compounds described herein that is effective for repelling insects. The absolute weight of a given compound that is included in a unit dose can vary widely. For example, about 0.01 to about 2 g, or about 0.1 to about 500 mg, of at least one compound can be included. Alternatively, the amount can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

The compositions can include a carrier such as a non-active ingredient that is not deleterious to shelf life of the compound(s) and that can solubilize or disperse the compound(s) to facilitate formulation into a convenient delivery form.

The compositions described herein can be prepared by various procedures using a variety of ingredients. Such procedures may include the step of mixing one or more compounds with one or more solvents, liquid solutions, solid matrices, semi-solid carriers, finely divided solid carriers or combinations thereof, and then, if necessary, formulating the product into the desired delivery system.

The compositions can contain acceptable carriers, excipients, diluents, and vehicles. For example, the compositions can be formulated into solutions, suspensions, powders, aerosols and the like. Examples of excipients, diluents, and carriers that are suitable for such formulations include buffers, suspension agents, solvents, extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Surface active agents such as cetyl alcohol and glycerol monostearate can be included. Carriers such as kaolin and bentonite can be added. Lubricants such as talc, calcium and magnesium stearate, and solid polyethylene glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

It is possible, for example, to prepare solutions using one or more aqueous or organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

The compounds may be formulated in unit dose form in ampoules, pre-filled syringes, small volume containers or in multi-dose containers. As noted above, preservatives can be added to help maintain the shelve life of the composition. The active agents and other ingredients may form suspensions, solutions, or emulsions in oily or aqueous vehicles, and may contain formulatory agents such as suspending, stabilizing and/or dispersing agents.

Alternatively, the compounds and other ingredients may be in powder form, obtained by aseptic isolation of sterile solid or by lyophilization from solution, for constitution with a suitable vehicle, e.g., sterile, pyrogen-free water, before use.

The compounds and composition can include antioxidants, surfactants, preservatives, film-forming, keratolytic or comedolytic agents, perfumes, flavorings and colorings. Antioxidants such as t-butylhydroquinone, butylated hydroxyanisole, butylated hydroxytoluene and $\alpha$-tocopherol and its derivatives can be added.

For topical administration, the compounds may be formulated by available methods for direct application. Compositions chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The percent by weight of a compound in a topical formulation will depend on various factors, but generally will be from 0.01% to 95% of the total weight of the formulation, and typically 0.1-85% by weight.

The compositions may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the pharmaceutical carriers and/or diluents that are useful in the pharmaceutical formulations of the present invention include water and physiologically acceptable buffered saline solutions such as phosphate buffered saline solutions pH 7.0-8.0.

The compounds can also be formulated in an aqueous solution when distributed or administered in an aerosol form. Thus, other aerosol pharmaceutical formulations may comprise, for example, a solution containing between about 0.1 mg/ml and about 100 mg/ml of one or more of one or more of the compounds described herein. Dry aerosol in the form of finely divided solid compound, or mixture of compounds, that are not dissolved or suspended in a liquid are also useful. The compounds and compositions may be formulated as dusting powders and comprise finely divided particles having an average particle size of between about 1 and 5 μm, alternatively between 2 and 3 μm. Finely divided particles may be prepared by pulverization and screen filtration using available techniques.

In some cases, spraying is a mode of administration. Hence, the compounds or compositions can be formulated for delivery by a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Aerosol delivery systems of the type disclosed herein are available from numerous commercial sources including Fisons Corporation (Bedford, Mass.), Schering Corp. (Kenilworth, NJ) and American Pharmoseal Co., (Valencia, CA).

Furthermore, the compounds may also be used in combination with other therapeutic agents, for example, pain relievers, anti-inflammatory agents, anti-bacterial agents, anti-fungal agents, and the like, whether for repelling insects or some a combination of conditions.

Kits

The present invention further pertains to a packaged composition such as a kit or other container for repelling insects.

In one embodiment, the kit or container holds a compound as well as instructions for preparing a composition that includes the compound. The kit can also include a carrier.

In another embodiment, the kit or container holds an effective amount of a composition for repelling insects, and instructions for using the composition for repelling insects. The composition includes at least one compound in an amount effective for control, prevention, or repelling insects. The compound(s) can be provided in combination with a carrier. Such a composition can be in liquid form, powder form or other form permitting ready application or administration.

The kits of the invention can also comprise containers with tools useful for applying the compositions or for administering the compositions of the invention. Such tools can include spreaders, brushes, mixing tools, spray devices, or a combination thereof.

The kits can also include a mosquito cage with: (a) a mounted digital camera; (b) a human hand glove with a screened window; (c) one or more magnetic frame (slightly larger than the dimension of the window); and one or more pieces of netting (slightly larger than the magnetic frame). One magnetic frame (the fixed magnetic frame) is affixed as a frame around the exterior of window on the human hand glove to serve as a base for stacking more magnetic window frames thereto. The fixed magnetic frame is above the surface of the glove fabric so that when a human hand is in the glove the One piece of netting can be treated with one or more test compounds. The treated netting can be placed on the fixed magnetic frame, and a second magnetic frame can be used to hold the treated netting in place several millimeters above the window in the glove. One or more untreated pieces of netting can be stacked above the treated netting, each one held in place by a magnetic frame. The stacked magnetic frames can be further secured with a binder clip.

The following non-limiting Examples illustrate some aspects of the compounds, compositions, and methods provided herein.

Example 1: Materials and Methods

This Example describes some of the materials and methods employed in the development of the invention.

Mosquito Strains

Five *Aedes aegypti* mosquito strains were used: ROCK and Orlando are two wild-type strains and $orco^{-/-}$ (i.e., orco) mosquito is a mutant mosquito strain with the Orco gene mutated as described by DeGennaro et al. and (*Nature* 498: 487-491 (2013)) obtained through BEI Resources, NIAID, NIH. KDR:ROCK is a pyrethroid-resistant strain (Smith et al. *Pest management science* 74, 737-745 (2018)). The OR31 mutant strain, $AaOr31^{-/-}$, was generated by the inventors in this study using the CRISPR-Cas9 technology and the mutation was backcrossed with parental ROCK mosquitoes for four generations to generate near isogenic line for functional analysis. One *Anopheles gambiae* strain was used: Kisumu (BEI Resources, NIAID, NIH).

The wild type *Aedes aegypti* odorant receptor 31 (AaOr31) sequence is provided herein as SEQ ID NO:1.

```
  1 MAPTQNGRDR EKFLRVQLLC LALIGIKRHE TVSSRTIFHV
 41 CFISMVIMDL ATILFALEHA NDIALVCDCL GPTFTAYLGI
 81 VKQYCLSAHR VELWNIIETL RRLKDYAGIS EIESIERNNK
121 IDRFLATAYL MSASATGSLF IIAALAKGCY KLIFQNIIEW
161 GFPLSLSFPF KTSHPIVFGM FFVWSSAAIY IVVFCSVSSD
201 ASFGGLASNV VVHFKLLQKR LQDATFADND ENLKQLIEYH
241 SLLLNLSRKI MSSFRVIIIN NLLVASVLLC VLGFQLVMFL
281 GSTLMLIYLM YVTAIVIQIT FFAYYGSLLL HESEEVSISI
321 YCSNWYEASP KTRRILLQCL MRAQVPVNTK AGFMVASLPT
361 LRAILNSAGS YVALLLSFTD N
```

A cDNA sequence encoding the SEQ ID NO:1 AaOr31 polypeptide is shown below as SEQ ID NO:7 (NCBI accession no. NM_001358160.1).

```
   1 GTAGAGTTAG GCCAATATTT CCGACAGCGA GCGCCGCCAA
  41 GTCACCAAAG ACGAAACGAA TGGCGCCCAC CCAAAATGGG
```

-continued

```
  81 AGGGACCGGG AAAAGTTTCT CCGGGTGCAG CTTTTGTGTC
 121 TTGCCCTGAT TGGAATAAAG CGTCACGAAA CTGTGTCAAG
 161 CCGGACGATT TTCCATGTCT GCTTTATCTC GATGGTGATC
 201 ATGGATTTGG CGACGATTCT TTTTGCCCTG GAGCATGCCA
 241 ACGACATTGC CCTCGTGTGT GACTGCTTGG GACCCACGTT
 281 TACCGCCTAT CTGGGCATCG TCAAGCAGTA CTGTCTCAGT
 321 GCCCATCGGG TGGAACTGTG GAACATTATC GAAACGCTGA
 361 GACGCCTCAA GGATTATGCT GGAATTAGCG AAATCGAATC
 401 AATTGAGCGG AACAACAAAA TCGATCGATT TCTGGCGACG
 441 GCTTATCTGA TGTCGGCATC TGCAACGGGA TCACTGTTCA
 481 TCATTGCGGC ACTGGCTAAA GGATGTTATA AGTTGATTTT
 521 TCAAAACATC ATCGAGTGGG GATTTCCGCT TTCGTTGAGC
 561 TTTCCATTCA AAACGAGTCA TCCGATTGTG TTCGGCATGT
 601 TTTTCGTCTG GTCCAGTGCC GCCATCTATA TAGTTGTATT
 641 TTGCTCTGTA TCCAGTGATG CCAGCTTCGG TGGATTGGCC
 681 TCCAATGTAG TTGTCCATTT CAAATTGCTC CAGAAACGTT
 721 TGCAGGATGC CACATTCGCT GACAATGACG AAAATTTAAA
 761 ACAACTCATT GAATACCACT CGCTGTTGCT TAATTTGTCG
 801 CGCAAAATTA TGTCATCATT TCGTGTTATT ATCATCAATA
 841 ATTTATTGGT AGCTTCGGTA TTATTATGCG TTCTGGGATT
 881 TCAACTGGTG ATGTTTCTGG GTTCTACACT GATGCTAATT
 921 TATCTCATGT ACGTGACGGC TATCGTGATT CAGATCACAT
 961 TTTTTGCATA TTATGGATCG CTTTTATTGC ATGAGAGTGA
1001 AGAAGTCAGC ATTTCGATCT ACTGTAGTAA TTGGTACGAA
1041 GCATCACCTA AAACCAGACG CATATTGCTC CAATGCTTGA
1081 TGCGGGCTCA AGTTCCGGTA AACACCAAAG CAGGATTCAT
1121 GGTAGCTTCC TTACCAACGT TGAGAGCCAT TCTTAATTCA
1161 GCTGGCTCGT ACGTTGCTTT GCTTTTATCA TTCACTGATA
1201 ATTAATATCC TG
```

Hand-in-Cage Assay

Figure 1A:
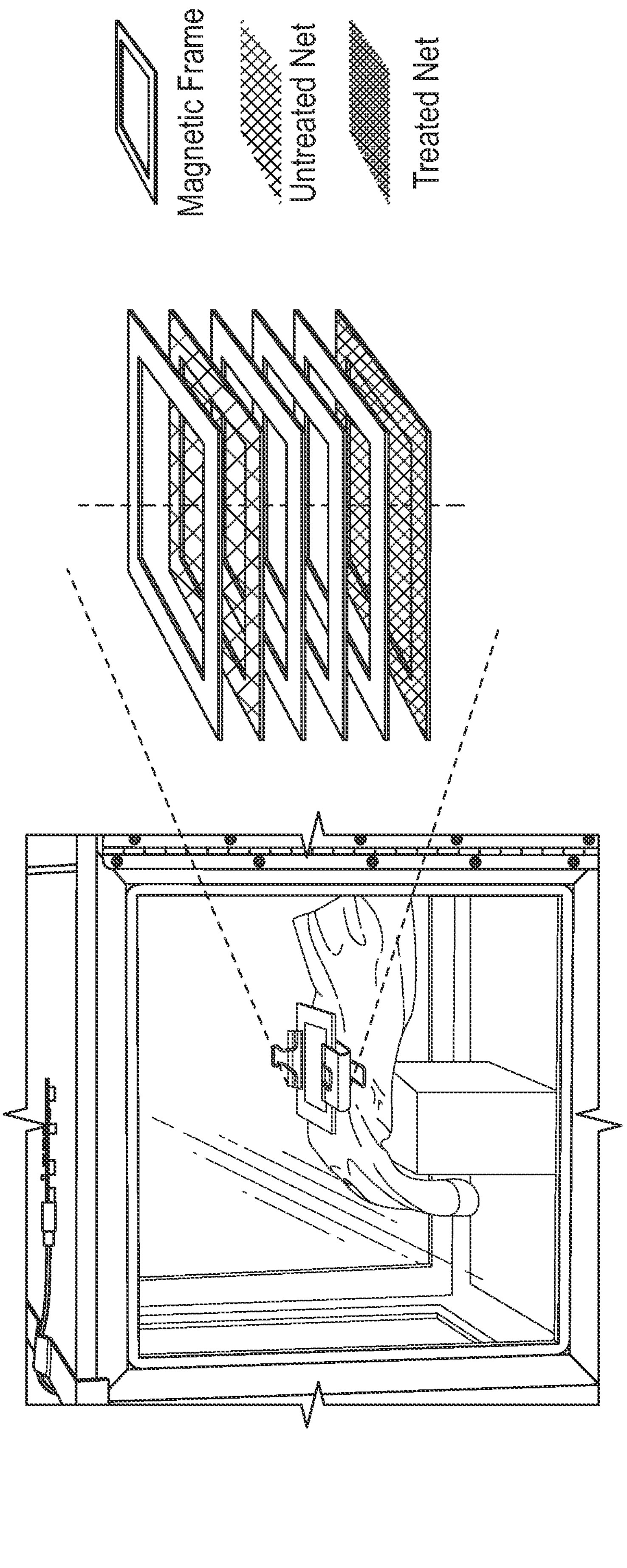
FIG. 1A-1D illustrate that compounds such as pyrethrum elicits spatial repellency in *Ae. aegypti* mosquitoes.

The hand-in-cage assay employed was similar to the hand-in-glove assay described by Boyle et al. (bioRxiv, 060178 (2016)). The setup for the hand-in-cage assay includes a 30 cm×30 cm×30 cm mosquito cage (BioQuip, Rancho Dominguea, CA), with a mounted digital camera and a human hand in a modified glove with a screened window. The digital camera (e-con Systems Inc, San Jose, CA, model: e-CAM51A) for video recording is mounted on the cage top and connected to a laptop computer. A nitrile rubber glove (Ansell Protective Products, Coshoton, OH, part number: 37-155) was cut on the back side of the glove to create a window (6 cm×5 cm) (FIG. 1A). A piece of magnetic frame (slightly larger than the dimension of the window) was glued onto the cut window which was used as a base for stacking more magnetic window frames (FIG. 1A; further explained below). One piece of test compound-treated polyester netting (Shason Textile Inc., part number: WS-B532-111, white; slightly larger than the dimension of the window) was placed on this fixed magnetic frame, which was ~3.0 mm above the glove. The second piece of the netting was untreated and placed ~6.0 mm above the treated net using a stack of four magnetic frames. The stacked magnetic frames were further secured with a binder clip. The stacking creates sufficient space between the treated net and the untreated net so that mosquitoes that land on the open window were not able to contact treated net, or to contact and pierce skin of a hand in the glove. The hand makes no contact with the treated net.

The assay was run in a room with humidity between around 50% and temperature between 27° C. to 30° C. Twenty-four hours before an assay, four to nine days-old females (about 40, mated, non-blood fed) were transferred into a mosquito cage. The cage was kept in an incubator where mosquitoes were provided only with water in a cotton ball placed on the top of the cage. Immediately before the assay, one researcher treated pieces of netting with 500 μl test compound dissolved in acetone in a glass Petri dish in an adjacent room. Acetone served a control. After letting acetone evaporate (~7 min), the researcher assembled and put on a modified glove. In the meantime, a second researcher or a lab assistant transferred the prepared cage from the incubator to a bench in the assay room. Both personnel avoided use of any hand lotions and cosmetic products before an assay and wore white lab coats and gloves during the assay. The hand with the modified glove was introduced into the cage to initiate the assay. Mosquitoes landing on the test window was recorded by the digital camera for five minutes. The number of mosquitoes landing during the second to fifth minutes was counted and recorded. For each cage, solvent (acetone) control was tested first and then followed with a treatment. Data from any cage that gave a low landing number in a control trial were discarded. The time interval of assays between control and treatment was at least 1.5 hours, allowing the mosquitoes to fully recover and residual vapors from experiments to be ventilated out of the room. Data from any cage that gave a low landing number in a control trial were discarded. Percentage repellency was determined for each cage using the following equation:

Percentage repellency=[1−(cumulative number of mosquitoes landed on the window of treatment/cumulative number of mosquitoes landed on the window of solvent treatment)]×100).

Each experiment was repeated at least by two different persons.

Once the assay was done, the cages were immediately sprayed with ethanol (99%) followed with a thorough rinse using distilled water to remove any residual chemicals on the cages and then a second ethanol spray before the cages were left to air dry. The modified glove and its magnetic frames were soaked in ethanol (99%) in a container, then rinsed with distilled water and a second ethanol rinse, before being left to air dry.

Single Sensillum Recording

Single sensilla recording was conducted as described in Liu et al. *J Insect Physiol* 59, 1169-1177 (2013). Female mosquitoes 4 days after eclosion were anaesthetized (2-3 min on ice) and mounted on a microscope slide (76×26 mm). An antenna was fixed using a double-sided tape to a cover slip resting on a small ball of dental wax to facilitate manipulation. The cover slip was placed at an appropriate angle to the mosquito head. Once mounted, the specimen was placed under a microscope (Nikon SMA645, Japan) and the antenna viewed at a high magnification (1000×). Two tungsten microelectrodes were sharpened in 10% $KNO_2$ at 2-10 V. The reference electrode, which was connected to ground, was inserted into the compound eye of the mosquito and the other was connected to the preamplifier (10×, Syntech, Kirchzarten, Germany) and inserted into the shaft of an olfactory sensillum to complete the electrical circuit to extracellularly record olfactory receptor neuron potentials (Den Otter et al., *Journal of Insect Physiology* 26, 465-472 (1980)). Controlled manipulation of the electrodes was performed using a micromanipulator (Burleigh PCS-6000, CA). The preamplifier was connected to an analog-to-digital signal converter (IDAC-4, Syntech, Germany), which in turn was connected to a computer for signal recording and visualization. The activity of co-located olfactory receptor neurons in each sensillum was assessed based on the differences in spike amplitude. The large spike amplitude was designated as cell A and the olfactory receptor neuron with the small spike amplitude was designated cell B (Ghaninia et al. *Eur J Neurosci* 26, 1611-1623 (2007)). Signals were recorded for 10 seconds starting 1 second before stimulation, and the action potentials were counted off-line over a 500-ms period before and after stimulation. The spontaneous firing rates observed in the preceding 500 milliseconds (ms) were subtracted from the total spike rates observed during the 500-ms stimulation, and counts were recorded in units of spikes/second.

Eighteen compounds besides pyrethrum from different chemical classes were selected for functional classification of olfactory sensilla with various morphological shapes (Extended Data FIG. 2). Each compound was diluted in dimethyl sulfoxide (DMSO) to a stock solution with a concentration of 100 μg/μl. Subsequently, a series of 10-fold dilutions were made from each of the stock solutions for each compound tested. For each dilution, a 10 μl portion was dispersed onto a filter paper strip (4×10 mm), which was then inserted into a Pasteur pipette to create the stimulus cartridge. A sample containing the solvent alone served as control. The airflow across the antennae was maintained constant at a 20 ml/second throughout the experiment. Purified and humidified air was delivered to the preparation through a glass tube (10-mm inner diameter) perforated by a small hole 10 cm away from the end of the tube, into which the tip of the Pasteur pipette could be inserted. The stimulus was delivered to the sensilla by inserting the tip of the stimulus cartridge into this hole and diverting a portion of the air stream (0.5 l/min) to flow through the stimulus cartridge for 500 ms using a stimulus controller (Syntech, Germany). The distance between the end of the glass tube and the antennae was ≤1 cm. The number of spikes/second was obtained by averaging the results for each sensillum/compound combination.

The Empty Neuron System

The method of Carey et al. (*Nature* 464, 66-71 (2010)) was used for heterologous expression of AgORs in the ab3 empty neurons. The Gal4 line (w; Cyo/Δhalo; Or22a-Gal4) was kindly provided by John Carlson (Yale Univ.), and 50 UAS-AgOr lines were obtained from the Bloomington *Drosophila* stock center.

Single Guide RNA (sgRNA) Design and Production

The procedure for sgRNA synthesis followed the description of Li et al. (*Proc. Natl Acad Sci USA* 114, E10540-E10549 (2017)) with minor modifications. Two guide RNAs were designed by searching the sense and antisense strands of the AaOr31 gene (AAEL013217) for the presence of protospacer-adjacent motifs (PAMs) with the sequence of NGG using the Chopchop online tool (see website at chopchop.cbu.uib.no). An Or31 cDNA sequence (AAEL013217; NCBI accession no. NM_001358160.1) from *Aedes aegypti* is shown below as SEQ ID NO:7.

```
   1 GTAGAGTTAG GCCAATATTT CCGACAGCGA GCGCCGCCAA
  41 GTCACCAAAG ACGAAACGAA TGGCGCCCAC CCAAAATGGG
  81 AGGGACCGGG AAAAGTTTCT CCGGGTGCAG CTTTTGTGTC
 121 TTGCCCTGAT TGGAATAAAG CGTCACGAAA CTGTGTCAAG
 161 CCGGACGATT TTCCATGTCT GCTTTATCTC GATGGTGATC
 201 ATGGATTTGG CGACGATTCT TTTTGCCCTG GAGCATGCCA
 241 ACGACATTGC CCTCGTGTGT GACTGCTTGG GACCCACGTT
 281 TACCGCCTAT CTGGGCATCG TCAAGCAGTA CTGTCTCAGT
 321 GCCCATCGGG TGGAACTGTG GAACATTATC GAAACGCTGA
 361 GACGCCTCAA GGATTATGCT GGAATTAGCG AAATCGAATC
 401 AATTGAGCGG AACAACAAAA TCGATCGATT TCTGGCGACG
 441 GCTTATCTGA TGTCGGCATC TGCAACGGGA TCACTGTTCA
 481 TCATTGCGGC ACTGGCTAAA GGATGTTATA AGTTGATTTT
 521 TCAAAACATC ATCGAGTGGG GATTTCCGCT TTCGTTGAGC
 561 TTTCCATTCA AAACGAGTCA TCCGATTGTG TTCGGCATGT
 601 TTTTCGTCTG GTCCAGTGCC GCCATCTATA TAGTTGTATT
 641 TTGCTCTGTA TCCAGTGATG CCAGCTTCGG TGGATTGGCC
 681 TCCAATGTAG TTGTCCATTT CAAATTGCTC CAGAAACGTT
 721 TGCAGGATGC CACATTCGCT GACAATGACG AAAATTTAAA
 761 ACAACTCATT GAATACCACT CGCTGTTGCT TAATTTGTCG
 801 CGCAAAATTA TGTCATCATT TCGTGTTATT ATCATCAATA
 841 ATTTATTGGT AGCTTCGGTA TTATTATGCG TTCTGGGATT
 881 TCAACTGGTG ATGTTTCTGG GTTCTACACT GATGCTAATT
 921 TATCTCATGT ACGTGACGGC TATCGTGATT CAGATCACAT
 961 TTTTTGCATA TTATGGATCG CTTTTATTGC ATGAGAGTGA
1001 AGAAGTCAGC ATTTCGATCT ACTGTAGTAA TTGGTACGAA
1041 GCATCACCTA AAACCAGACG CATATTGCTC CAATGCTTGA
1081 TGCGGGCTCA AGTTCCGGTA AACACCAAAG CAGGATTCAT
1121 GGTAGCTTCC TTACCAACGT TGAGAGCCAT TCTTAATTCA
1161 GCTGGCTCGT ACGTTGCTTT GCTTTTATCA TTCACTGATA
1201 ATTAATATCC TG
```

Linear double-stranded DNA templates for all Or31 sgRNAs were generated by template-free polymerase chain reaction (PCR) using NEB Q5 high-fidelity DNA polymerase (catalog #M0491S). PCR reactions were heated to 98° C. for 30 seconds, followed by 35 cycles of 98° C. for 10 seconds, 58° C. for 10 seconds, and 72° C. for 10 seconds, then 72° C. for 2 minutes. PCR products were purified using Promega Wizard@SV Gel and PCR Clean-up System (catalog #A9281). Following PCR, sgRNAs were synthesized using the Ambion Megascript T7 in vitro transcription kit (catalog #AM1334, Life Technologies) according to the manufacturer's protocol using 300 ng of purified DNA template. Following in vitro transcription, the sgRNAs were purified using the MegaClear Kit (catalog #AM1908, Life Technologies) and diluted to 1000 ng/μl in nuclease-free water and stored in aliquots at −80° C. Recombinant Cas9 protein from *Streptococcus pyogenes* was obtained commercially (CP01, PNA Bio Inc) and diluted to 1000 ng/μl in nuclease-free water and stored in aliquots at −80° C.

CRISPR Mediated Microinjections

Embryonic collection and CRISPR microinjections were performed following the procedure described by Li et al. (*Proc. Natl Acad Sci USA* 114, E10540-E10549 (2017)). Briefly, ROCK mosquitoes were blood-fed 5 days before egg collection. An ovicup filled with ddH2O and lined with filter paper was placed into a cage and female mosquitoes were allowed to lay eggs in the ovicup in the dark. After 15-30 minutes, the ovicup was taken out and unmelanized eggs were transferred onto a glass slide. The eggs were quickly aligned on a wet piece of filter paper. Aluminosilicate needles were pulled on a Sutter P-1000 needle puller and beveled using a Sutter BV-10 beveler. An Eppendorf Femotojet was used for power injections under a compound microscope at 100× magnification. About 50 eggs were injected each time immediately after fresh eggs were collected. The concentration of components used in the study was as follows; Cas9 protein at 300 ng/μl, each sgRNA at 40 ng/μl. After injection, eggs were placed in a cup filled with water, allowed to hatch and then allowed to develop into adults. To identify mutants, genotyping was performed at each generation of mosquitoes after injection by cutting one hind leg off for genomic DNA isolation. Genomic DNA was extracted using the DNeasy blood & tissue kit (QIAGEN) following the manufacturer's protocol. Target loci were amplified by PCR using AeOR31F (5'-ATTGGCATGCGCTACTTTTATT-3', SEQ ID NO:8) as one primer and AaOR31R (5'-ATAACATCCTTTAGCCAGTGCC-3', SEQ ID NO:9) as another primer. PCR products were gel purified and sent directly for Sanger sequencing using the forward primer used in PCR reactions.

The wild type sequence of the genomic sequence in an intron-exon junction of the AaOR31 gene is shown below (SEQ ID NO:10; see also FIG. 3G).

1 CCTAATTTGT TTAACCTTTC AGCTGGAACT AGCGAAATCG

41 AATCAATTGA GCGGAACAAC AAAATCGATC GATTTCTAGC

81 GACGGCTTAT CTGATGTCGG CATCTGCAAC GGGATCACTG

121 TTCATCATTG CGGCACTGGC TAAAGGATGT TATAAGTTGA

161 TTTTTCAAAA CATCATCGAG

This region of the AaOR31 gene was targeted by such CRISPR methods described above, and the underlined sequences in bold of the SEQ ID NO:10 shown above are missing in the mutant $AaOR3^{-/-}$ genomic sequence. Hence, the genomic sequence in $AaOR3^{-/-}$ mosquitoes has the following mutant sequence (SEQ ID NO:11) in the region of the defective $OR31^{-/-}$ gene (see FIG. 3G).

```
  1 CCTAATTGCG GAACAACAAA ATCGATCGAT TTCGGCTTAT
 41 CTGATGTCGG CATCTGCAAC GGGATCACTG TTCATCATTG
 81 CGGCACTGGC TAAAGGATGT TATAAGTTGA TTTTTCAAAA
121 CATCATCGAG
```

Statistical Analysis

All statistical analysis was done using Prism 5 (GraphPad Software). Data are presented as mean±s.e.m. Unpaired Student's t-tests was used to compare two sets of data. If the data did not meet the normality or equality of the variance assumptions needed for Student's t-tests, the equivalent Mann-Whitney Rank Sum test was used instead. The significance for all the tests was set to a P value<0.05. Each hand-in-cage experiment and SSR recording were repeated by two or more researchers.

Example 2: Molecular Basis of Pyrethrum Repellency

This Example describes experiments designed to elucidate the molecular basis of pyrethrum repellency.

The spatial repellency of pyrethrum was examined using a hand-in-cage assay (Ogoma et al. PLoS neglected tropical diseases 11, e0005455 (2017)). In this behavioral assay, mosquitoes were attracted to a human hand in a modified glove (FIG. 1A) with a screened window on the back of the glove. The mosquitoes landed on a piece of control mesh secured on the top of the window. Between the control mesh and the hand is another mesh treated with a test compound, with which mosquitoes cannot make direct contact (FIG. 1A).

Figure 1B:
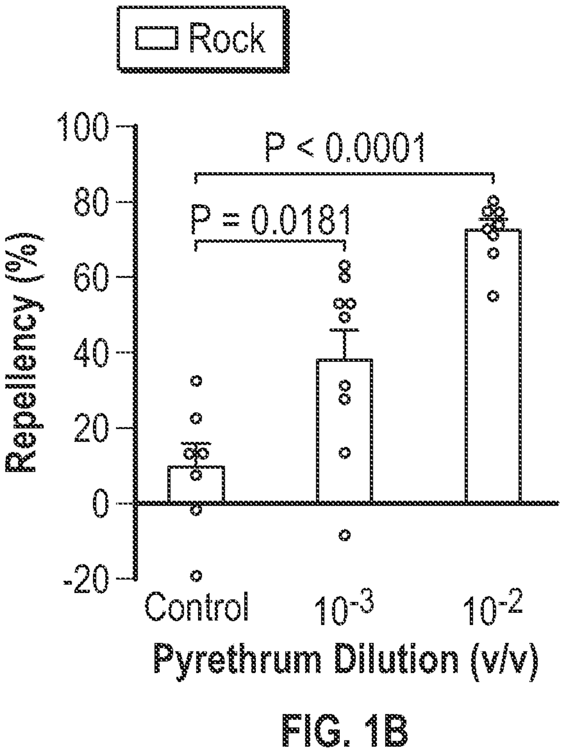
Figure 1C:
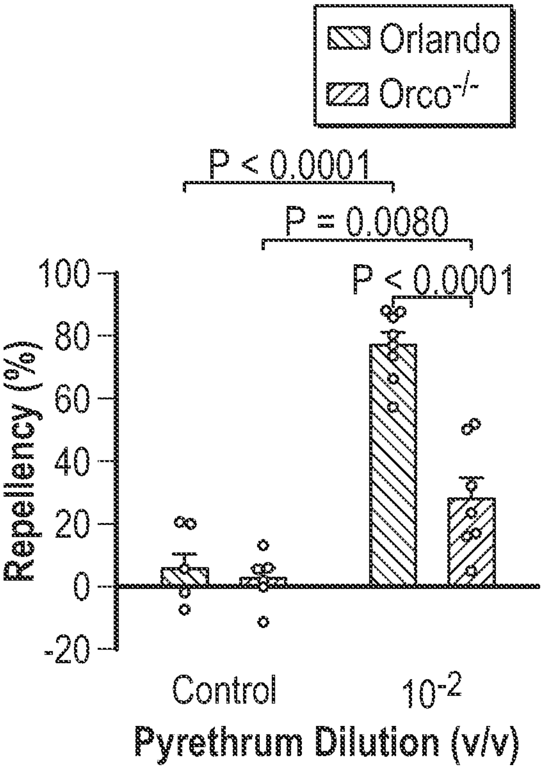
Figure 1D:
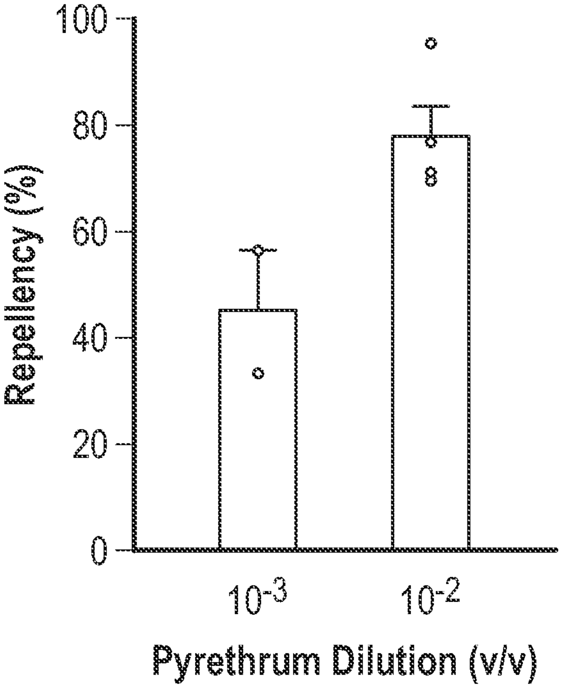

As shown in FIG. 1B, when the second mesh was treated with pyrethrum (Sigma-Aldrich), the landing frequency of female *Ae. aegypti* mosquitoes onto the top mesh was significantly reduced in a dose-dependent manner. Similar spatial pyrethrum repellency was observed in *Anopheles gambiae* mosquitoes (FIG. 1D).

Spatial pyrethrum repellency was then examined to determine whether it depends on the mosquito olfaction system. In insects, in addition to individual odorant receptors (Ors) that are responsible for recognizing specific odorants, an obligate Or co-receptor (Orco) is required for detection of diverse odorants (Sato et al. Nature 452, 1002-1006 (2008); Larsson et al. Neuron 43, 703-714 (2004)). Orco mutants were used to infer whether insect attraction or avoidance response is Or-mediated. As shown in FIG. 1C, pyrethrum repellency was significantly reduced in anosmic orco$^{-/-}$ *Ae. aegypti* mosquitoes, compared to the wild-type *Ae. aegypti* strain Orlando, from which the orco$^{-/-}$ mutant was generated (DeGennaro et al. Nature 498, 487-491 (2013)). These results show that spatial repellency by pyrethrum is largely Or-mediated.

Figure 2A:
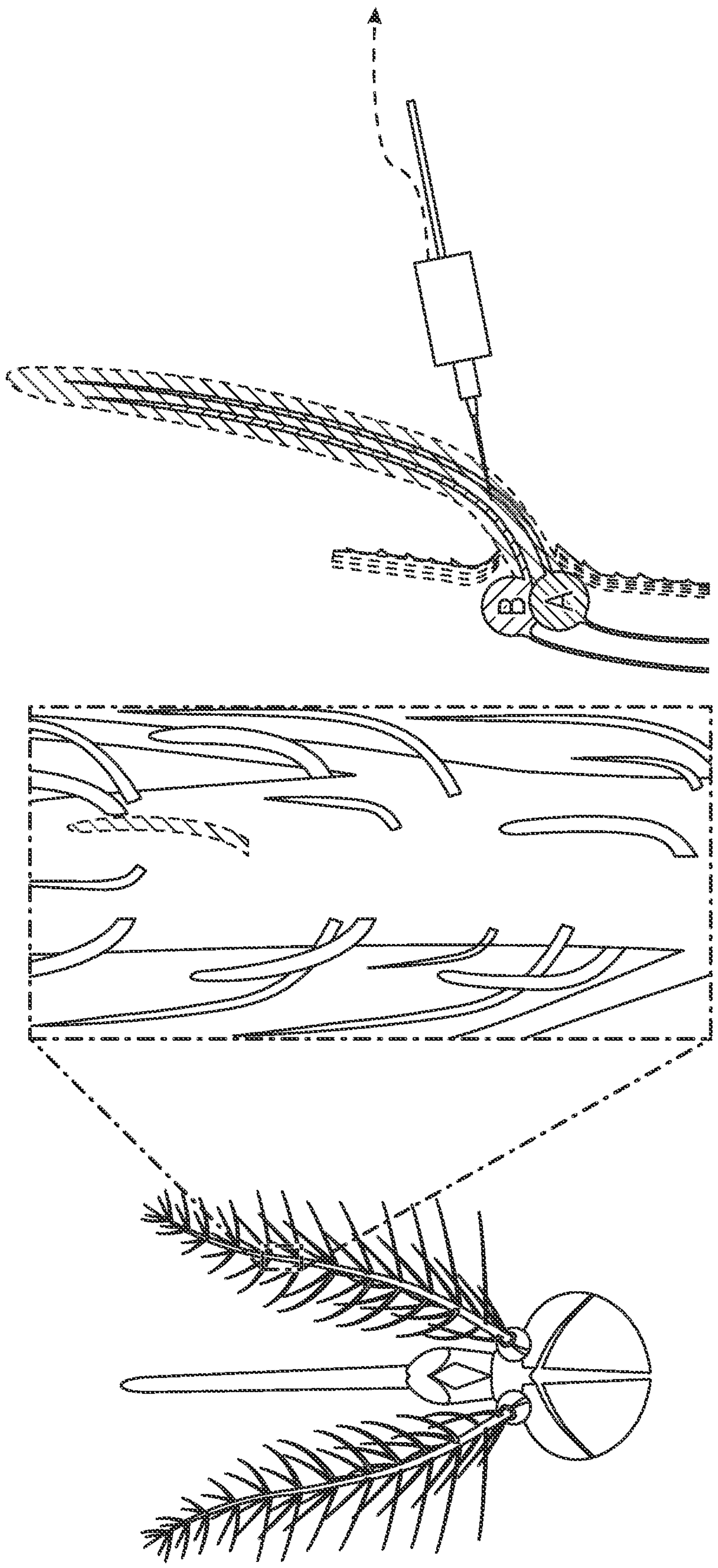
FIG. 2A-2O illustrate identification and compound-specific responses by pyrethrum-responsive sensilla in *Ae. aegypti* antennae.

Insect odorant receptors (Ors) are mainly expressed in olfactory receptor neurons (ORNs) in antenna. Three major morphologically distinct types of antennal trichodae sensilla are recognized in *Ae. aegypti* antennae: short sharp-tipped (sst), long sharp-tipped (lst), and short blunt-tipped (sbt) (Ghaninia et al. *Eur J Neurosci* 26, 1611-1623 (2007)). Each *Ae. aegypti* sensillum houses two neurons: The neuron that generates larger spikes (i.e., action potentials) is called the A neuron and the neuron that produces smaller spikes is called the B neuron (FIG. 2A).

To identify which mosquito olfactory receptor neuron(s) responds to pyrethrum, single sensillum recordings (SSR) were performed of *Ae. aegypti* antennal olfactory sensilla in response to a panel of odorants (FIG. 2C-2L), most of which are plant-derived mosquito repellents, such as pyrethrum, (±)-citronellal, geranyl acetate and (−)-borneol. Three responsive sst sensilla were identified, sst1-3, and six responsive sbt sensilla, sbt1-6, based on their response profiles to the odorants in the panel (FIG. 2B, 2D-2L). The long sharp-tipped (lst) sensilla did not respond to any odorants in the panel tested.

Figure 2B:
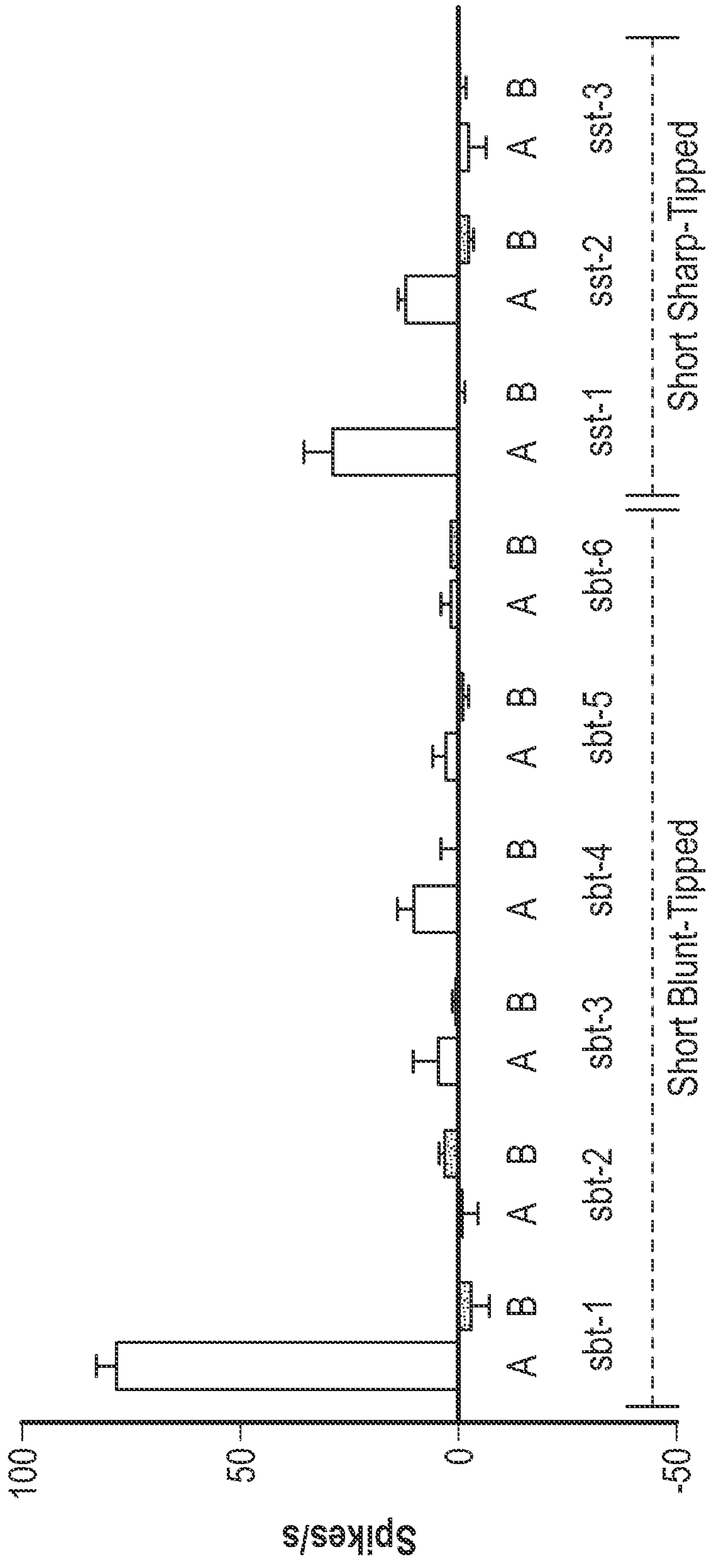
FIG. 2B graphically illustrates single sensillum recording responses of sst and sbt sensilla to pyrethrum ($10^{-2}$ concentration)(n=8 sensilla for sbt-1; n=7 for sbt-2; n=3 for sbt-3 and sbt-4; n=2 for sbt-5 and sbt-6; n=5 for sst-1 and sst-2; n=8 for sst-3).
Figure 2C:
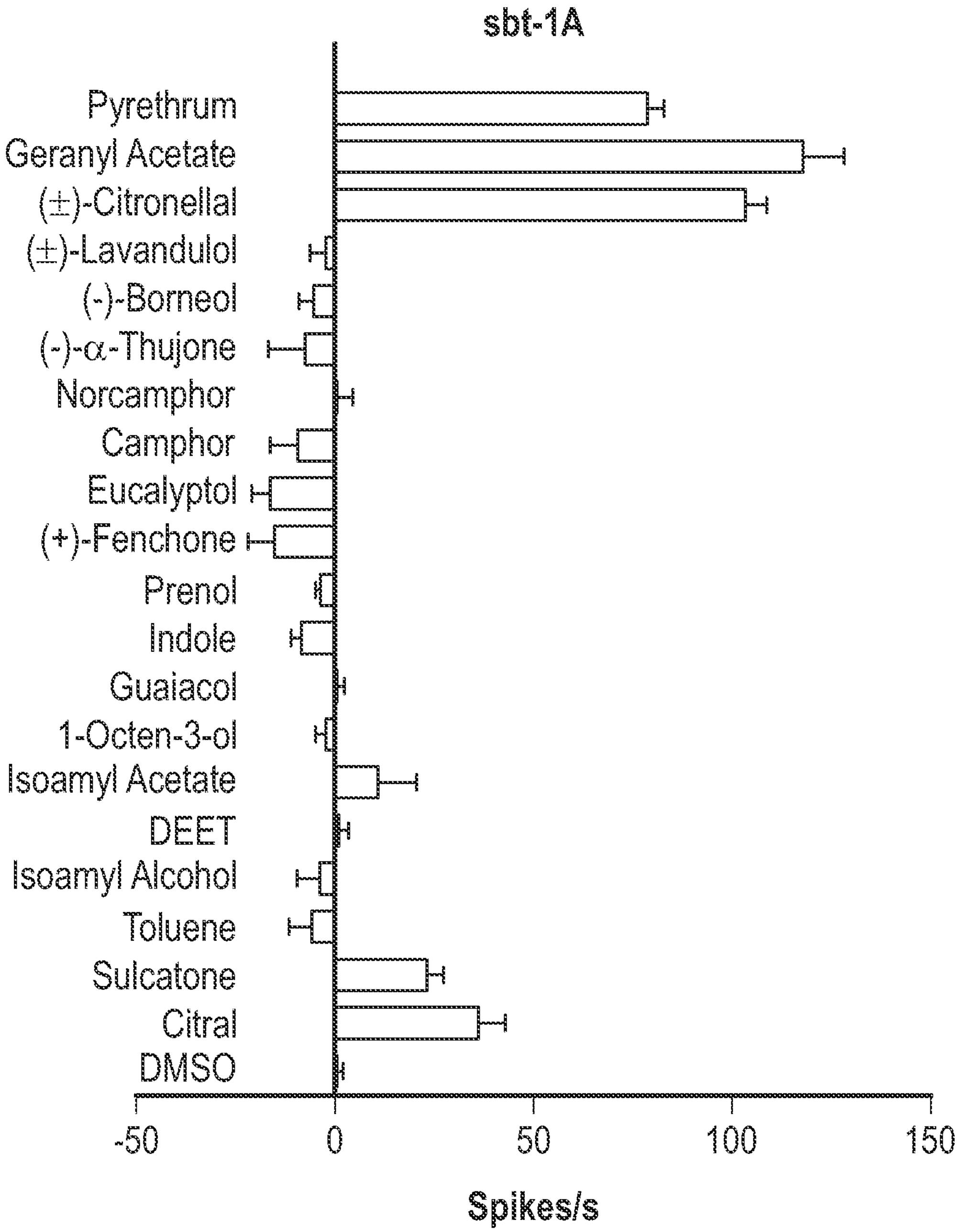
FIG. 2C graphically illustrates odorant responses to different compounds by sbt-1A (n=8 sensilla).
Figure 2D:
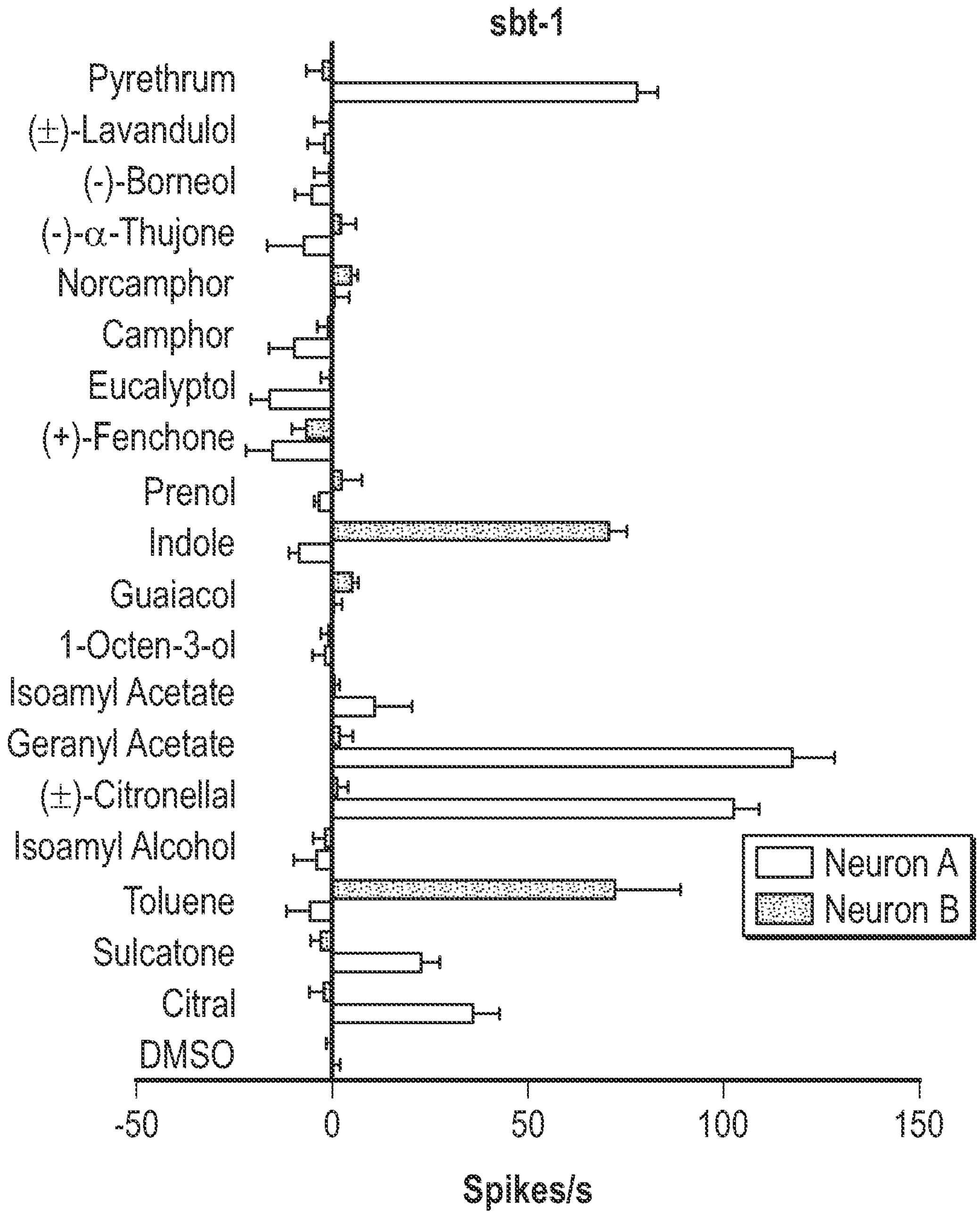
FIG. 2D graphically illustrates odorant responses to different compounds by sbt-1 (n=8 sensilla).
Figure 2E:
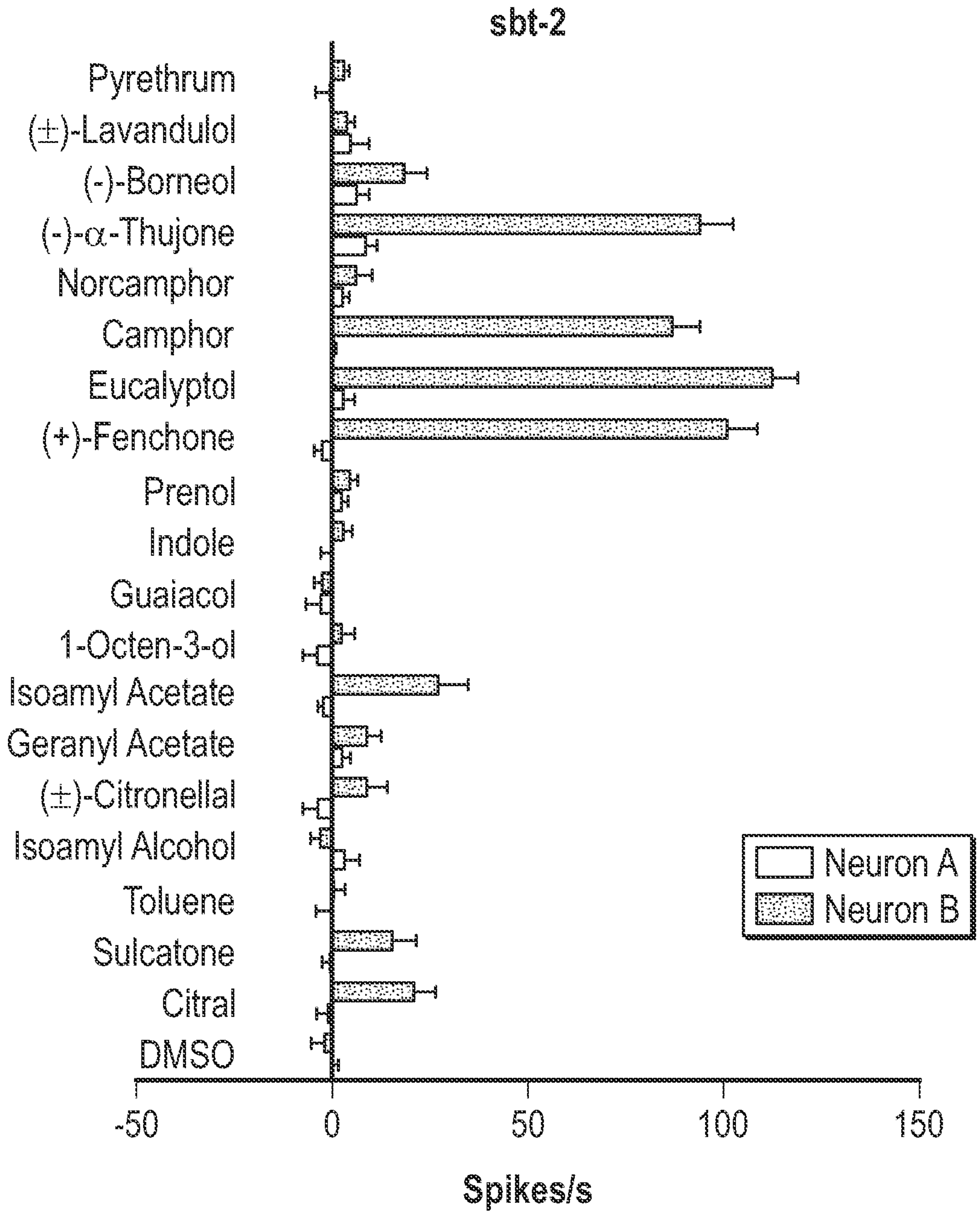
FIG. 2E graphically illustrates odorant responses to different compounds by sbt-2 (n=7 sensilla).
Figure 2F:
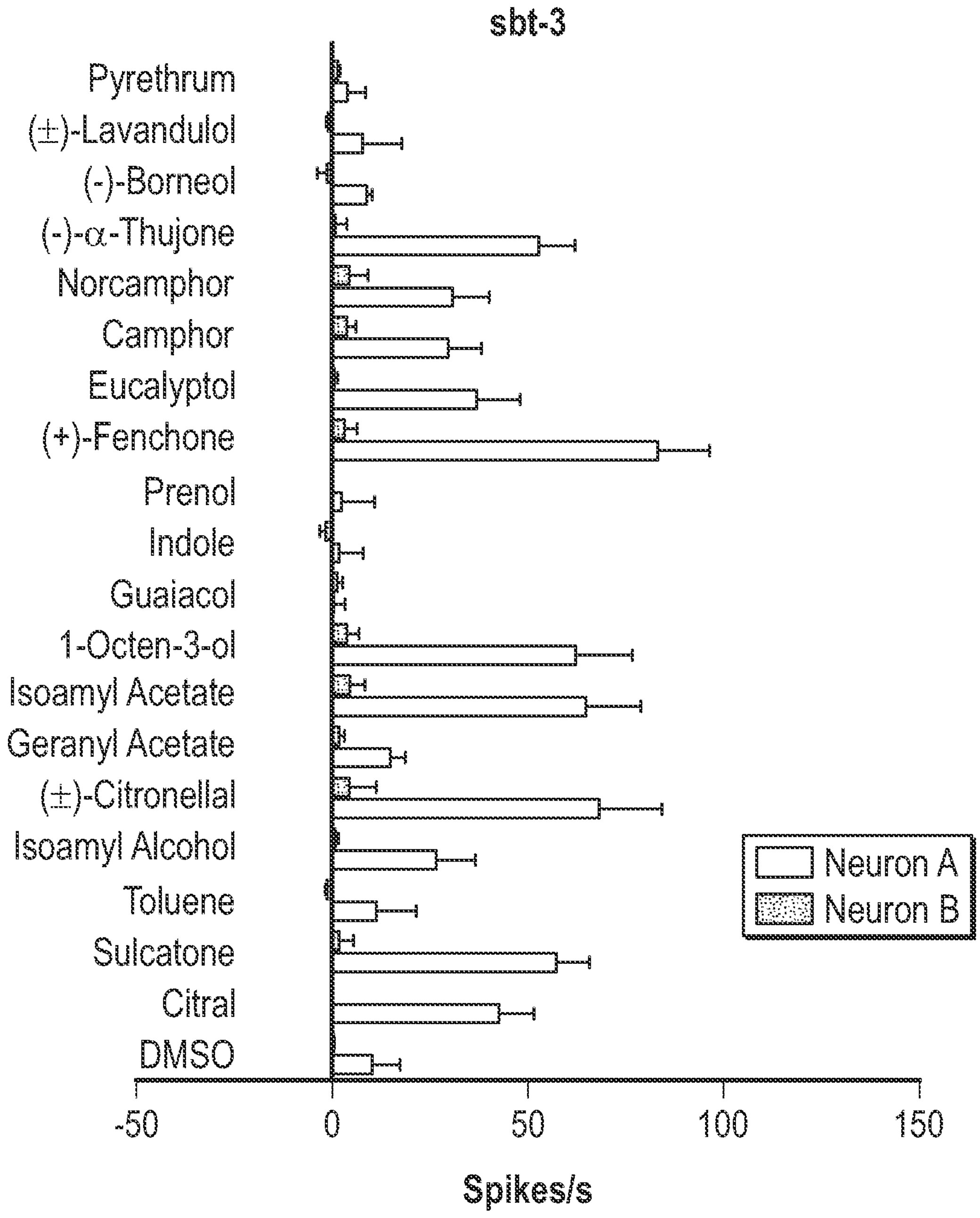
FIG. 2F graphically illustrates odorant responses to different compounds by sbt-3 (n=3 sensilla).
Figure 2G:
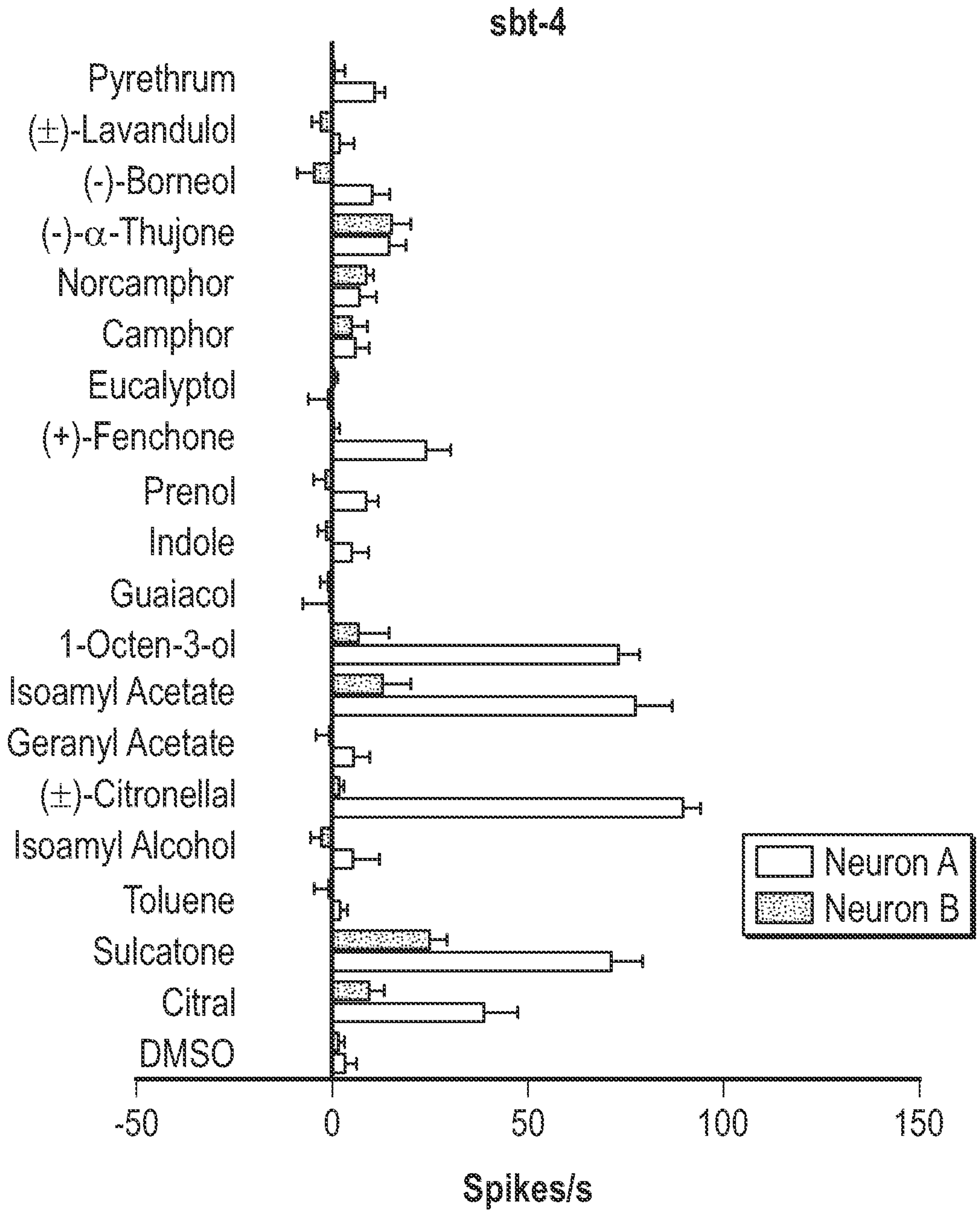
FIG. 2G graphically illustrates odorant responses to different compounds by sbt-4A and sbt4B (n=4 sensilla).
Figure 2H:
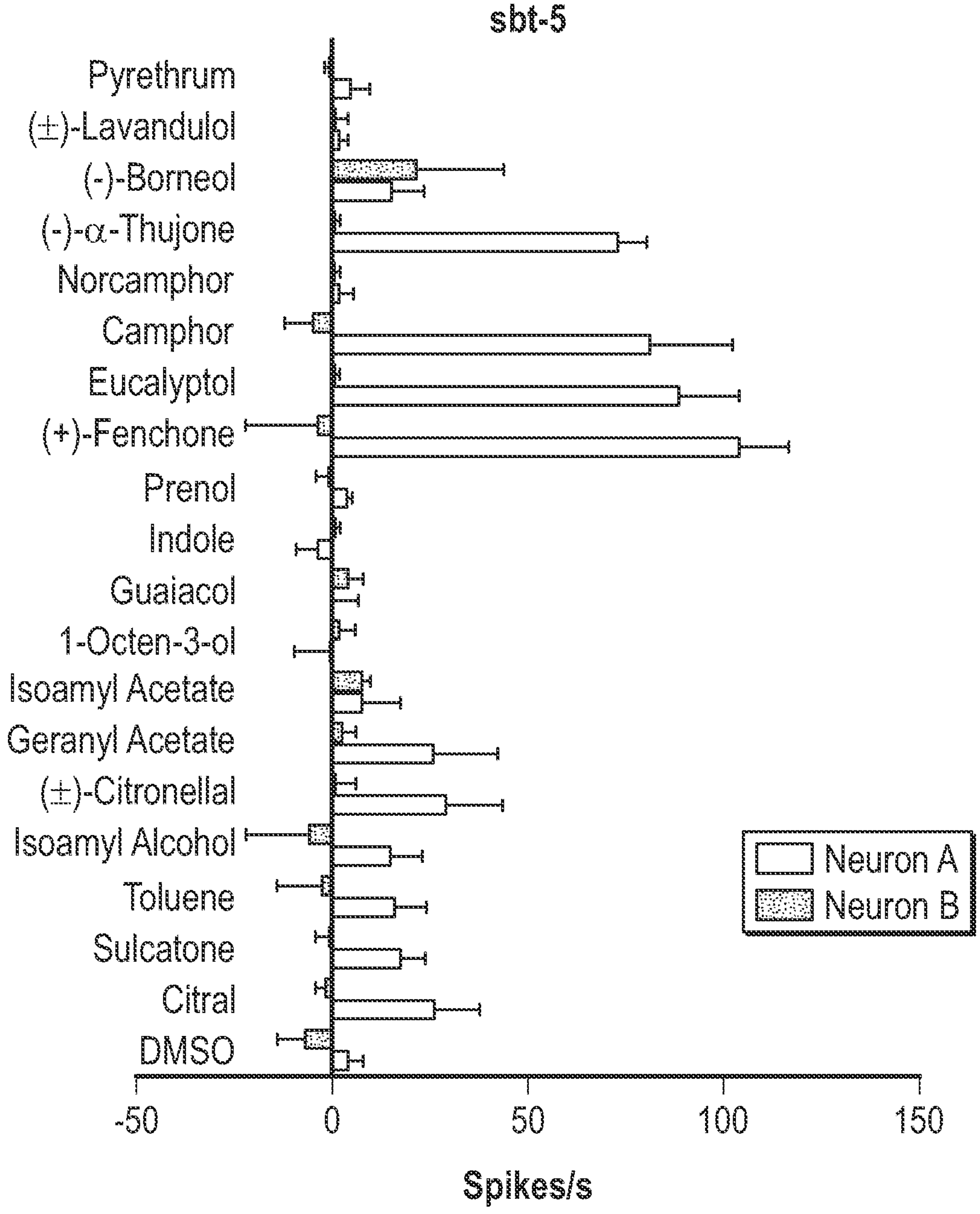
FIG. 2H graphically illustrates odorant responses to different compounds by sbt-5A and sbt-5B (n=2 sensilla).
Figure 2I:
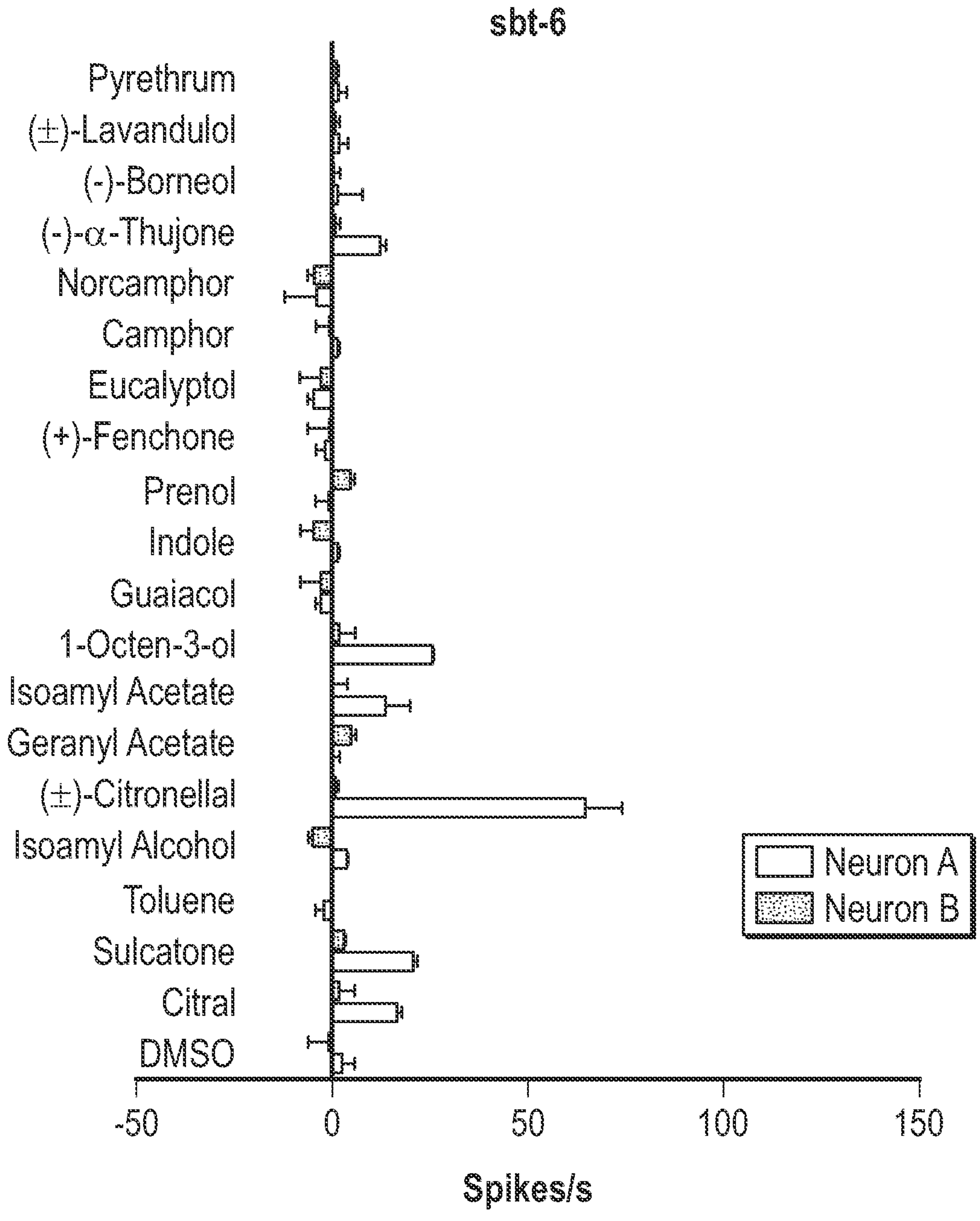
FIG. 2I graphically illustrates odorant responses to different compounds by sbt-6A and sbt-6B (n=2 sensilla).
Figure 2J:
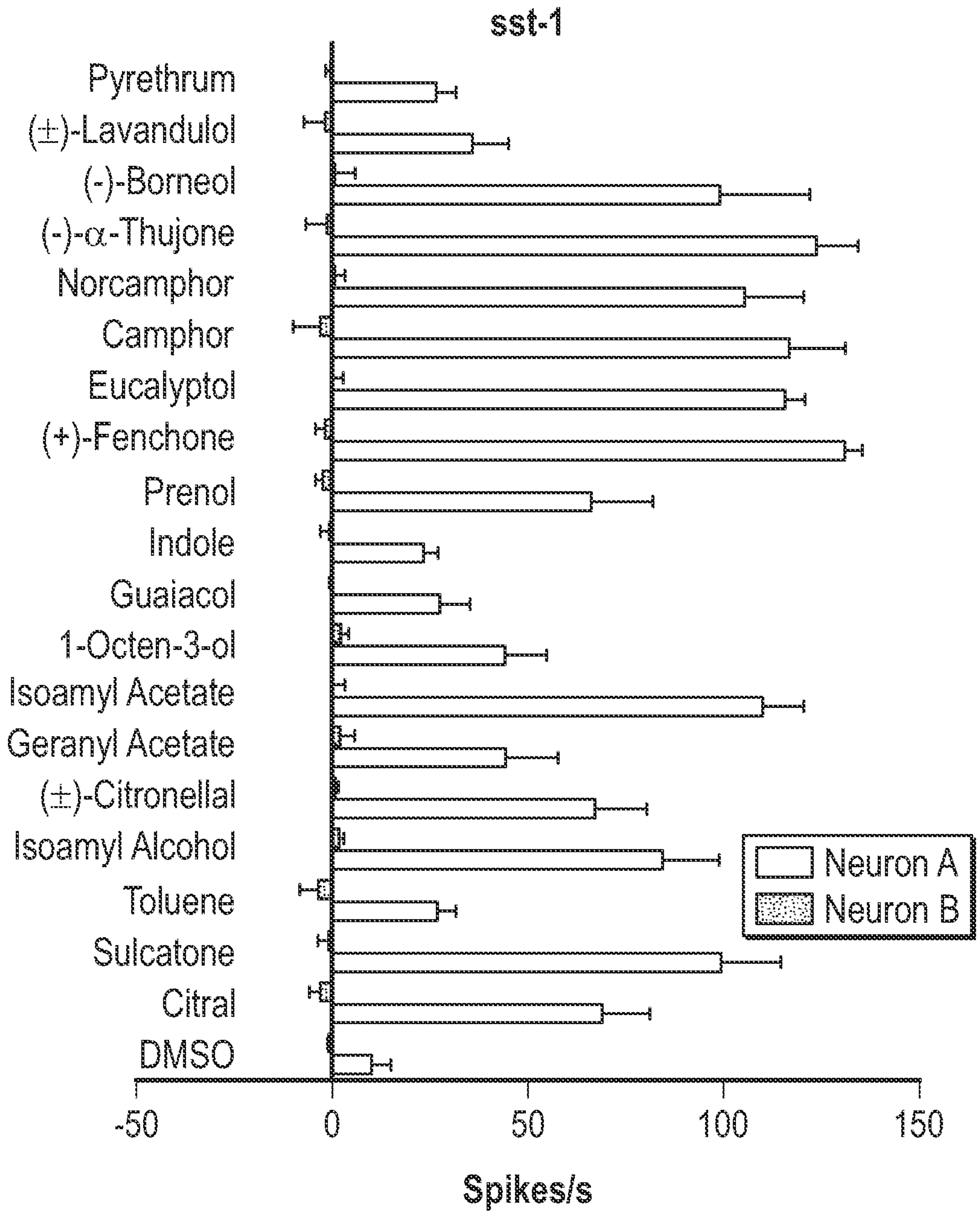
FIG. 2J graphically illustrates odorant responses to different compounds by sst-1A and sst-1B (n=5 sensilla).
Figure 2K:
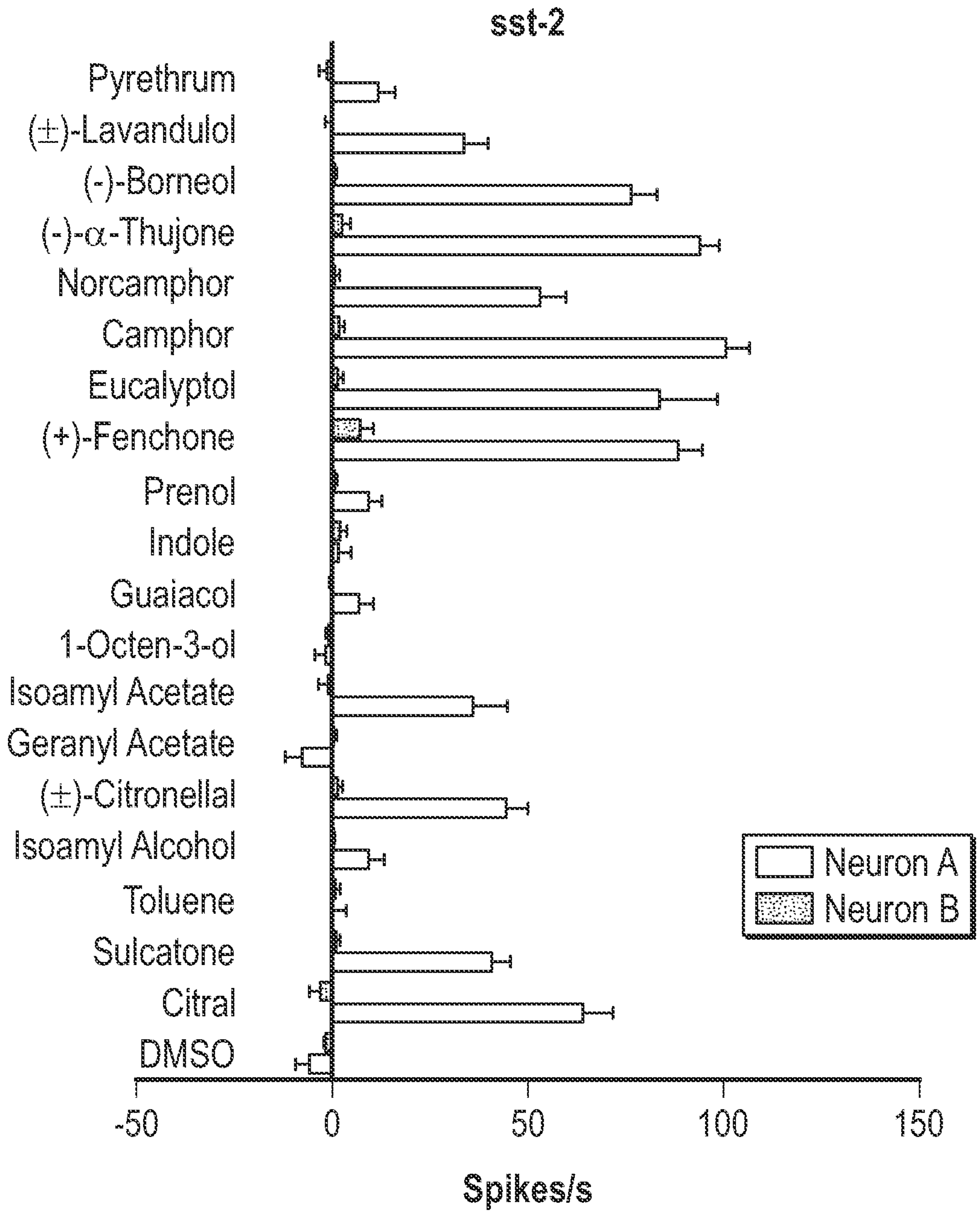
FIG. 2K graphically illustrates odorant responses to different compounds by sst-2A and sst-2B (n=5 sensilla).
Figure 2L:
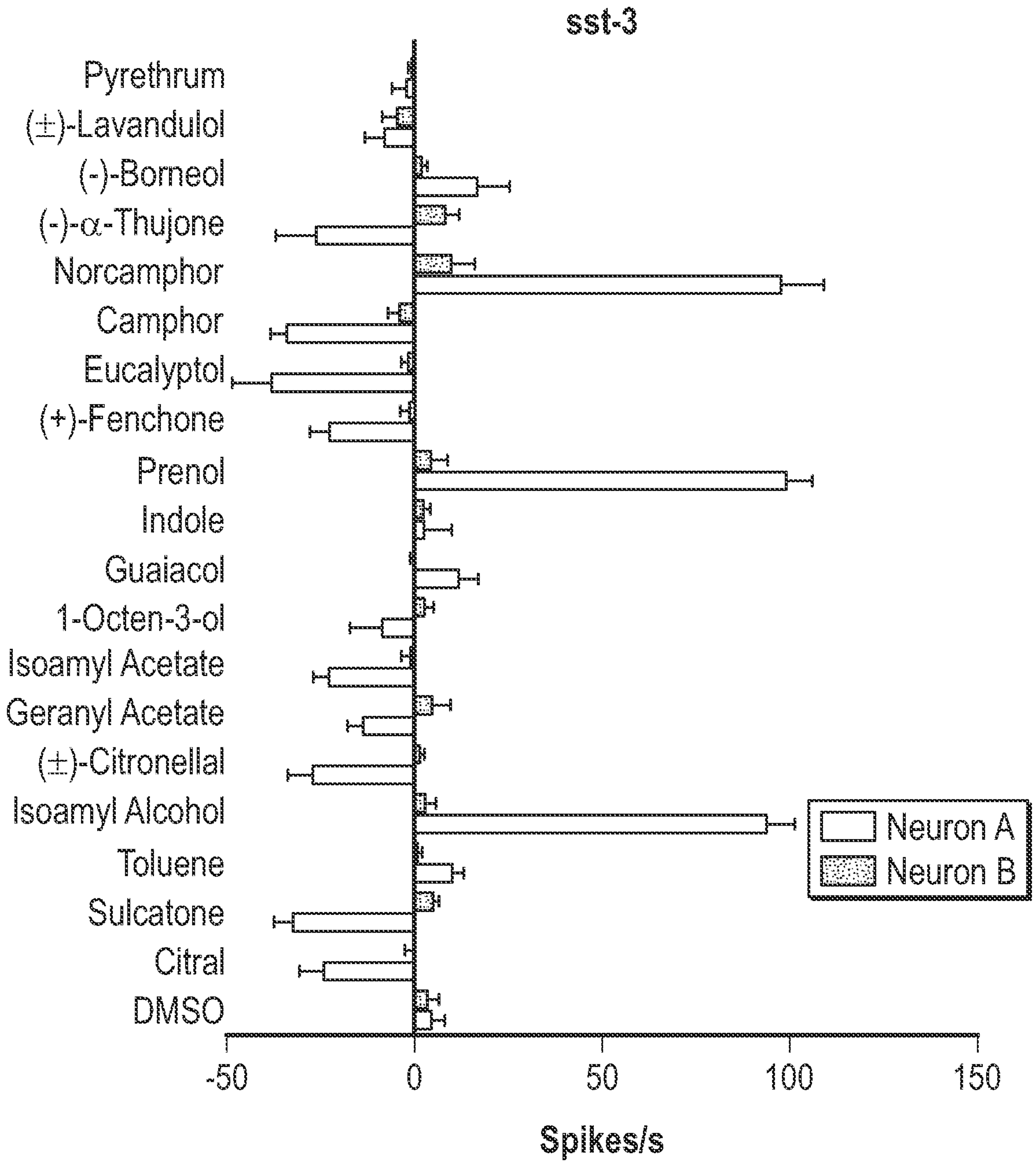
FIG. 2L graphically illustrates odorant responses to different compounds by sst-3A and sst-B (n=8 sensilla).
Figure 2M:
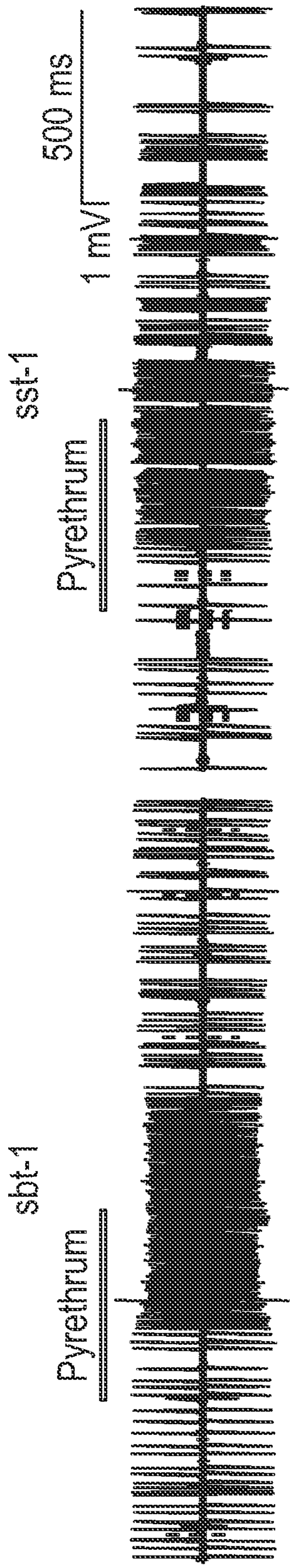
FIG. 2M shows representative single sensillum recording traces indicating increased firing of A neurons of stb-1 sensilla (from n=8 sensilla) or sst-1 sensilla (from n=5 sensilla) in response to pyrethrum ($10^{-2}$ dilutions) in ROCK mosquitoes.

Importantly, sbt-1 and sst-1 sensilla were most responsive to pyrethrum (FIG. 2B). In particular, the A neuron in the sbt-1 sensilla was excited by pyrethrum, while the B neuron was not (FIG. 2B). The sbt-1A neuron also exhibited strong excitatory responses to (±)-citronellal and geranyl acetate (FIG. 2C-2D). In contrast, the sbt-1B neurons were highly sensitive to indole and toluene (FIG. 2D). For sst-1 sensilla, pyrethrum specifically activated sst-1A neurons, but not sst-1B (FIG. 2B). In addition, sst-1A was also activated by other volatiles including (±)-citronellal, camphor, and also eucalyptol (FIG. 2J).

Figure 2N:
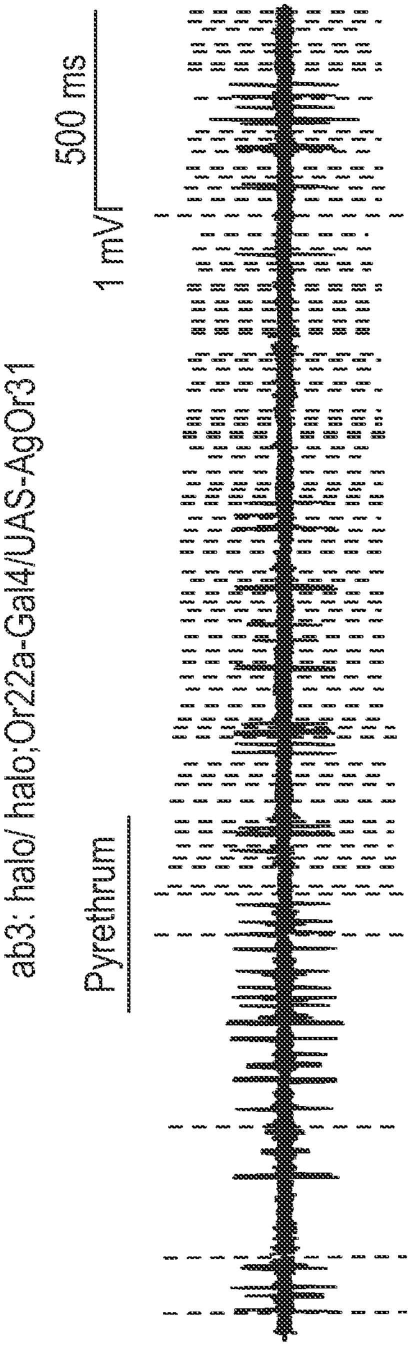
FIG. 2N shows representative single sensillum recording trace (n=8 sensilla) from *Drosophila* ab3A empty neurons expressing AgOr31 when exposed to pyrethrum ($10^{-2}$ dilution). *An. gambiae* AgOrs were expressed heterologously in the empty neuron (i.e., the ab3A neuron of the ab3 sensilla) in *D. melanogaster*.
Figure 2O:
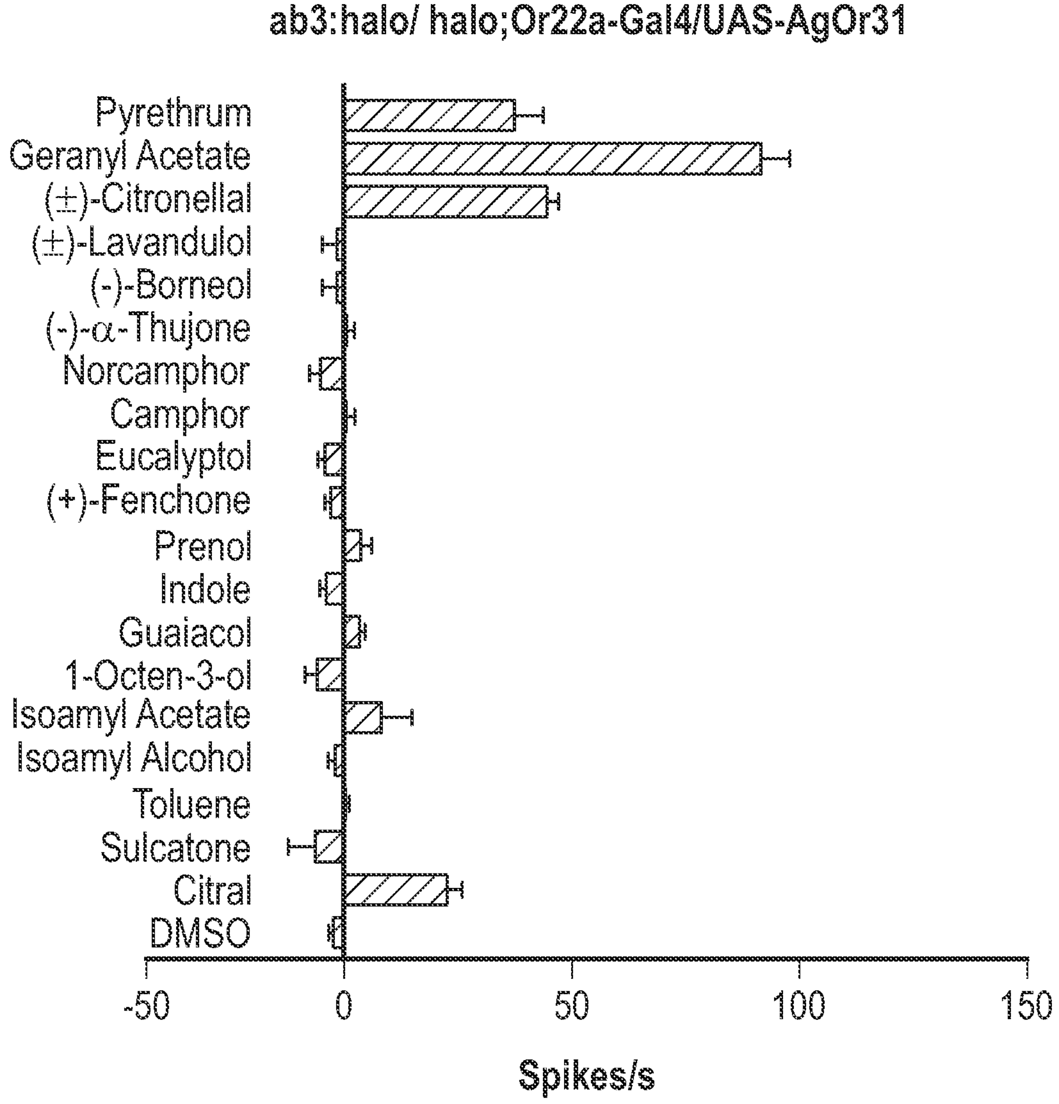

Having identified sbt-1 and sst-1 as primary olfactory receptor neurons that are responsive to pyrethrum, experiments were designed to identify the specific odorant receptors (Ors) that are involved in these responses. An indexed library of *An. gambiae* Ors (AgOrs) (Carey et al., *Nature* 464, 66-71 (2010)) was used. Each of the 50 AgOrs was expressed in the "ab3 empty neuron" system of *Drosophila melanogaster*, in which the endogenous odorant receptor gene, Or22a, in the ab3 sensillum was deleted (FIG. 2N-2O, FIG. 3A).

Single sensillum recordings (SSR) were then examined from the resulting chimera ab3 sensillum that expressed the individual AgOrs in the *D. melanogaster* antenna when these flies were exposed to the same panel of odorants used in the analysis of *Ae. aegypti* sensilla. As shown in FIG. 3C, pyrethrum activated AgOr20, AgOr31, AgOr53 and AgOr76 at the $10^{-2}$ dilution. The odorant response profile of the sbt-1A neuron matches remarkably well with that of AgOr31 (FIGS. 2C, 2O). The response profile of the sst-1A or sbt-1A neurons did not match with the odorant response profiles of any of the four pyrethrum-activated AgOrs, AgOr20, AgOr31, AgOr53 and AgOr76.

Figure 3B:
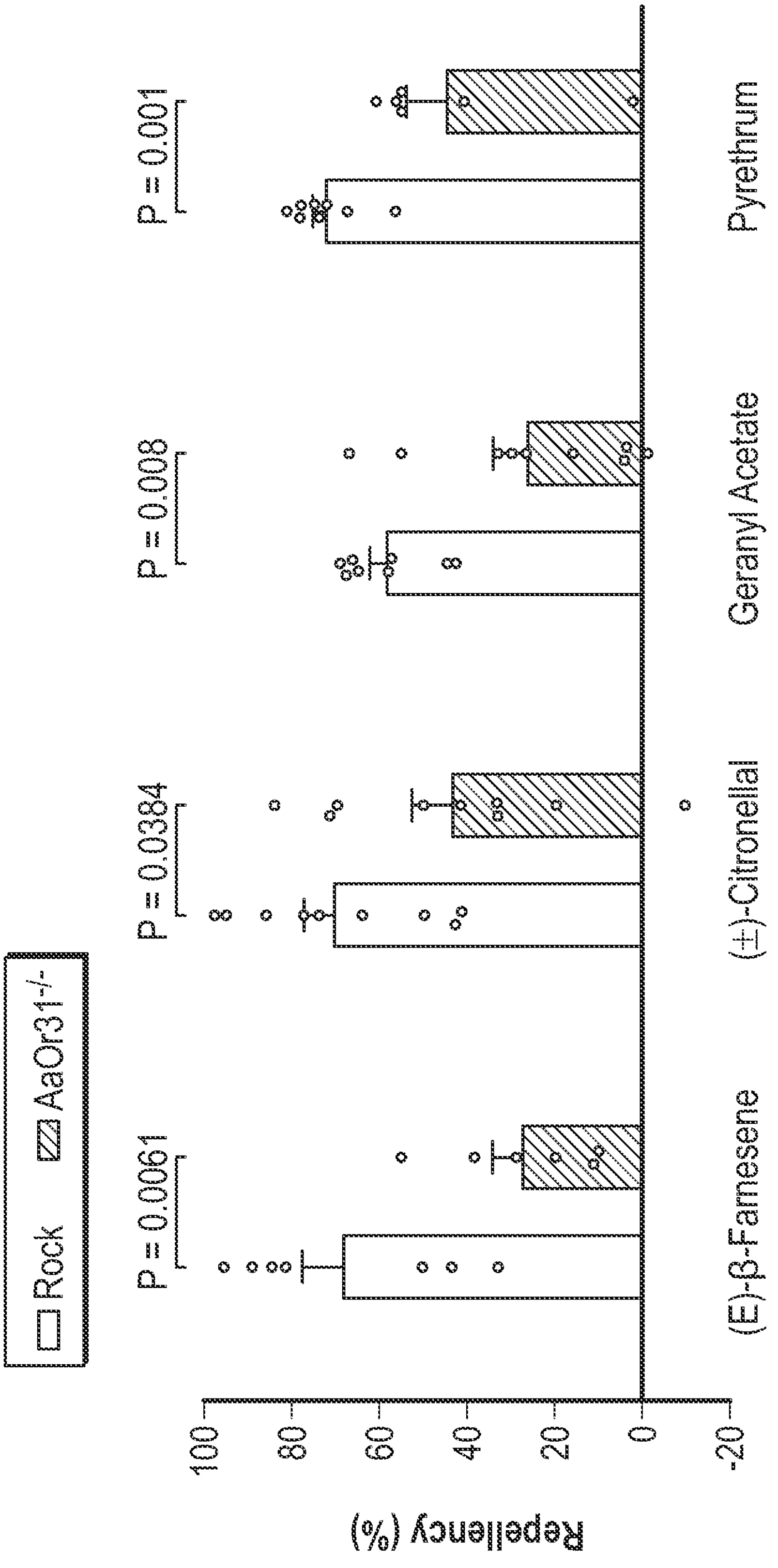
Figure 3C:
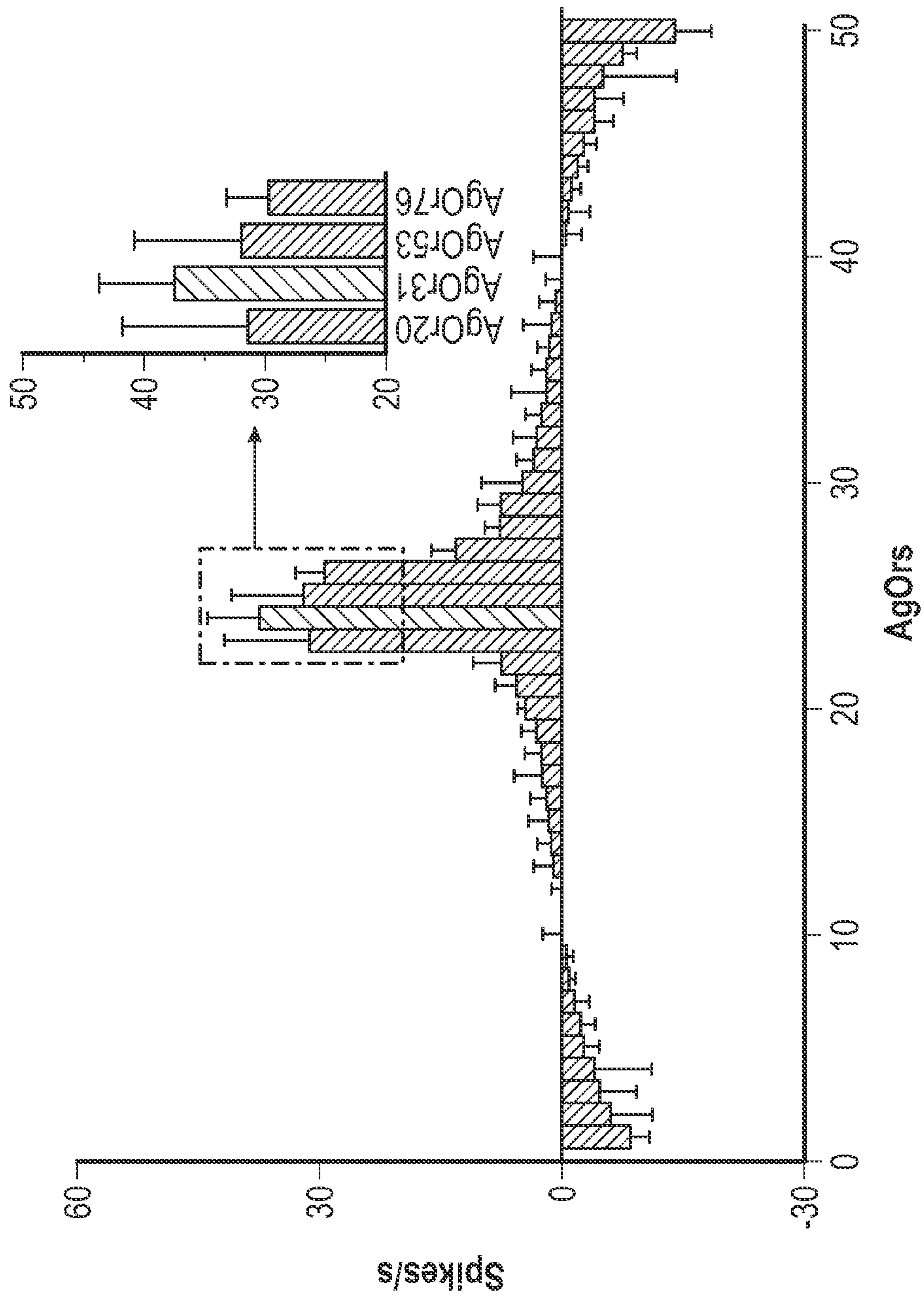
Figure 3D:
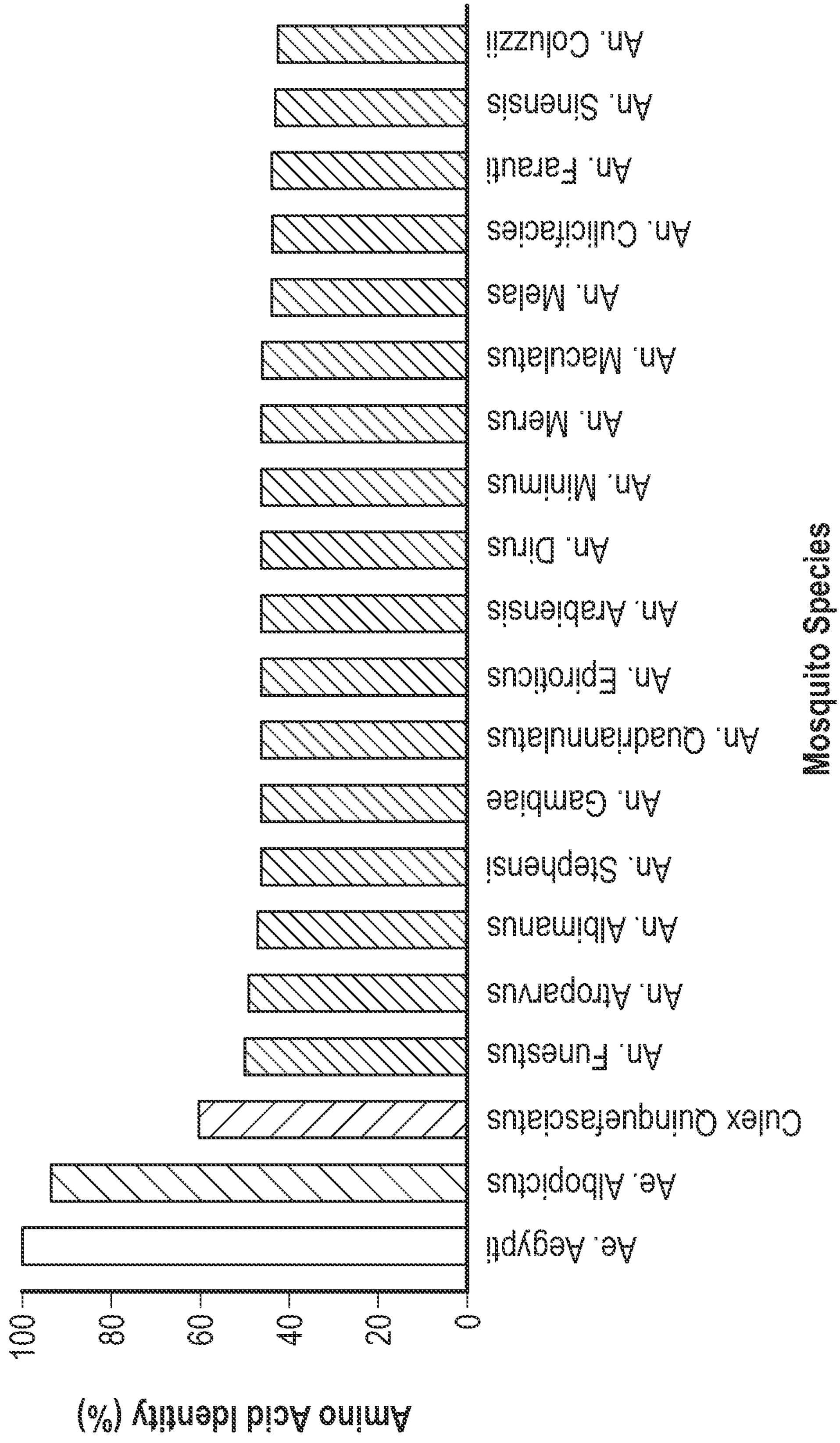

Bioinformatic analysis of pyrethrum-responsive AgOrs/AaOr31 revealed that orthologs of the Or31 gene are present in all three major disease-transmitting mosquito genera, *Aedes, Anopheles* and *Culex* (FIG. 3D). In contrast, no orthologues of AgOr20, AgOr53 or AgOr76 are found in *Ae. aegypti* or other mosquito species, suggesting that Or31 represents a widely conserved mosquito Or gene and that AgOr32, AgOr53 and AgOr76 likely belong to a family of *Anopheles*-specific Or genes.

Pyrethrum is an extract containing six insecticidal esters (i.e., pyrethrins) as major components and several phytoterpenes as minor components, including (E)-β-farnesene (EBF), β-cubebene, ethyl palmitate, and ethyl linoleate. Experiments were designed to evaluate which component(s) in pyrethrum activates Or31 by conducting single sensillum recordings of Or31-expressing chimera ab3 sensilla to various components of pyrethrum.

Figure 3E:
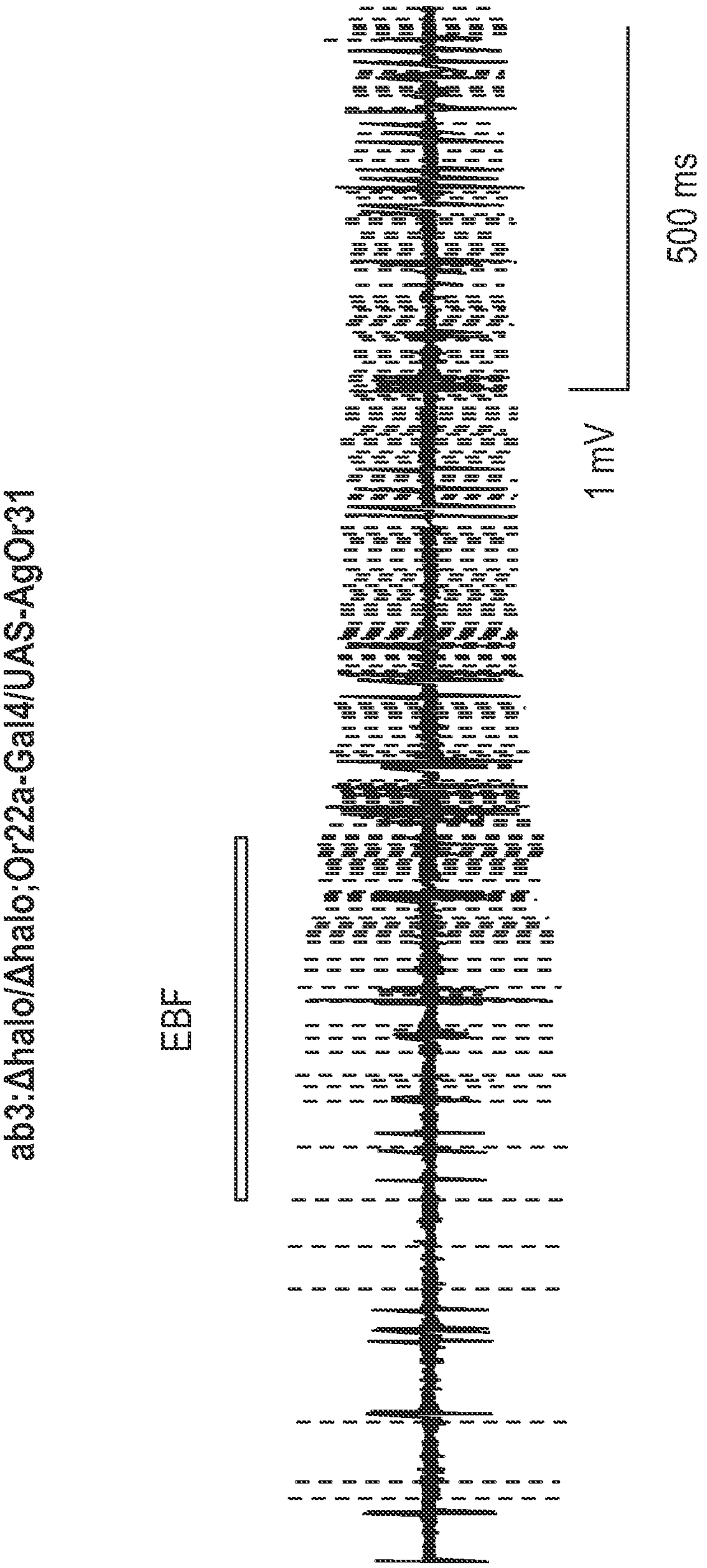
Figure 3F:
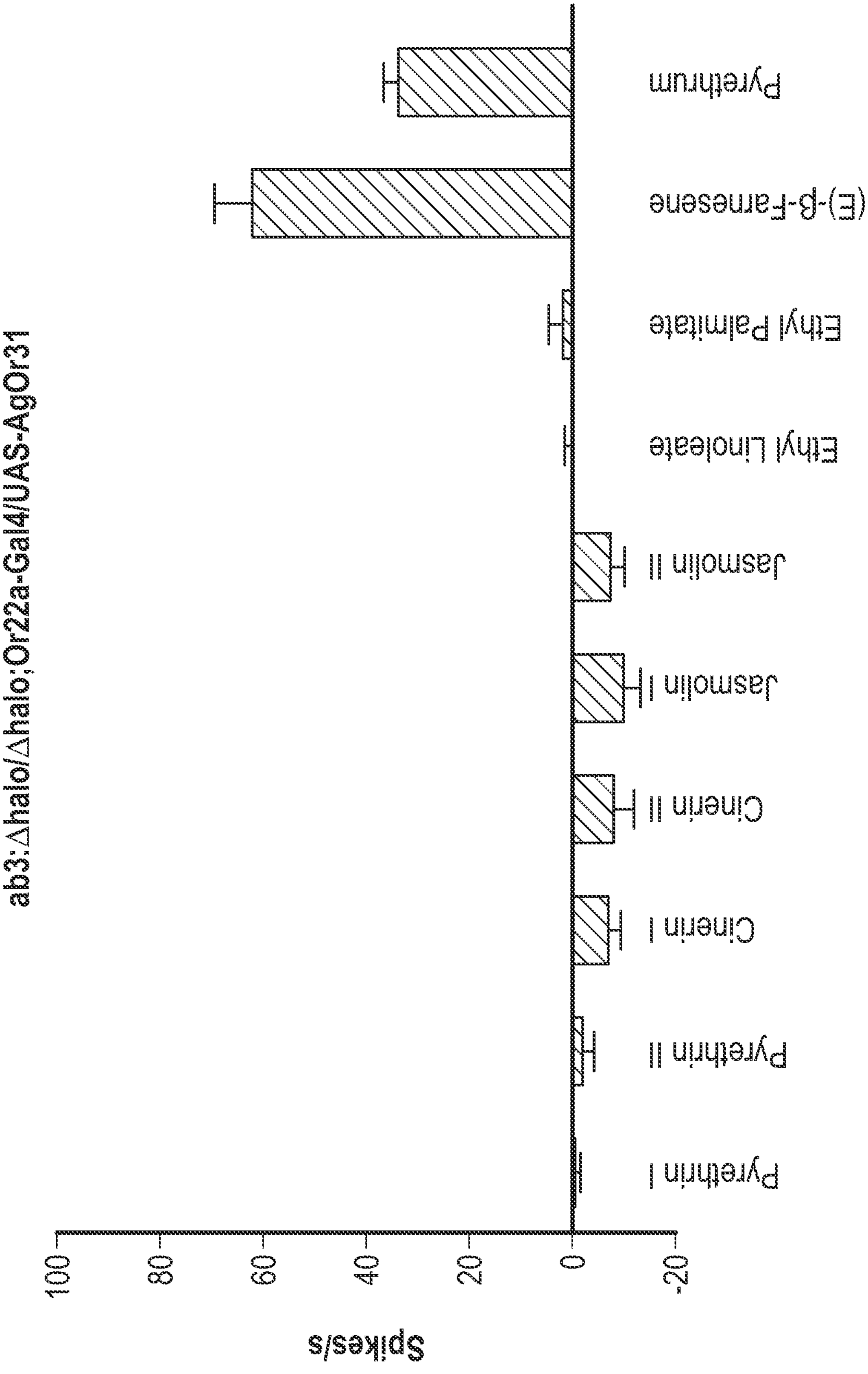

(E)-β-farnesene (at $10^{-2}$ dilution; from Sigma-Aldrich) not only activated AgOr31 expressed in *Drosophila* antennae having ab3 empty neurons (FIG. 3E-3F), but also Ae. *aegypti* sbt-1A neurons (FIG. 3C) and elicited spatial repellency in mosquitoes (FIG. 3B). None of the insecticidal esters, ethyl palmitate or ethyl linoleate activated AgOr31 or Ae. *aegypti* sbt-1A neurons. Samples of β-cubebene were not commercially available to be examined.

Next, experiments were performed to ascertain whether *Ae. aegypti* Or31 (AaOr31) contributes to mosquito avoidance behavior to pyrethrum, (E)-β-farnesene and other volatiles that activate AaOr31. For this purpose, AaOr31 knockout (AaOr31$^{-/-}$) mosquitoes were generated in *Ae. aegypti* strain ROCK using the CRISPR-Cas9 technology. Genotyping revealed that the AaOr31 gene of $AaOr31^{-/-}$ mosquitoes carried two deletions in exon 2 of AaOr31, which resulted in a premature stop codon (FIG. 3G). Strikingly, the response of sbt-1A neurons to (E)-β-farnesene, geranyl acetate or (±)-citronellal was completely abolished in $AaOr31^{-/-}$ mosquitoes (FIG. 3A). As a control, the response of sbt-1B neurons in $AaOr31^{-/-}$ mosquitoes to indole and toluene remained intact, showing specificity. Furthermore, the repellency by (E)-β-farnesene, (±)-citronellal, and geranyl acetate were all significantly reduced in $AaOr31^{-/-}$ mosquitoes compared to wild-type mosquitoes (FIG. 3B). Similarly, knockout of AaOr31 abolished the response of sbt-1A neurons to pyrethrum (FIG. 3A) and reduced pyrethrum repellency (FIG. 3B). Collectively, these data showed that AaOr31-mediated repellency pathway is an important component of pyrethrum repellency. In fact, Or31 is the first conserved mosquito odorant receptor that has been demonstrated to mediate repellency.

As shown in FIG. 3B, more than 40% of pyrethrum repellency at $10^{-2}$ dilution remained in $AaOr31^{-/-}$ mosquitoes. Furthermore, the percentage of (E)-β-farnesene in pyrethrum extracts is generally very low (from 1.25% to 1.97% based on the analysis of the pyrethrum extracts), which alone would not be sufficient to evoke repellency. These results indicate that additional mechanism(s) are involved in pyrethrum repellency. As shown in FIG. 2B, sst-1 was the only other type of sensillum, other than sbt-1, that strongly responded to pyrethrum.

Figure 4A:
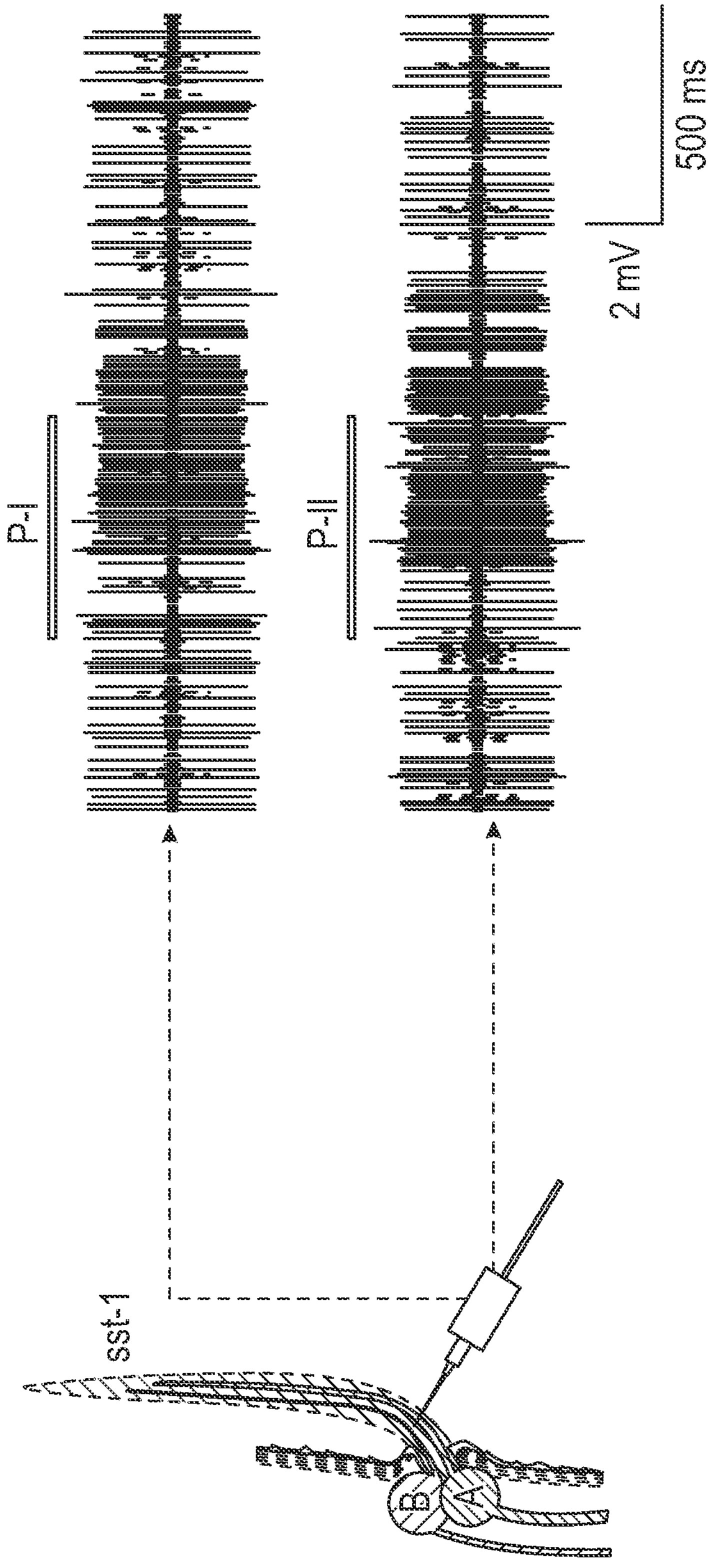
FIG. 4A-4J illustrate that pyrethrin-induced repellency is synergized by (E)-β-farnesene via activation of both AaOr31 and sodium channels.

The inventors tested whether additional component(s) in pyrethrum would elicit repellency by activating the sst1-associated olfactory pathway. Pyrethrin I (P-I) and pyrethrin II (P-II) were two major components purified by the inventors from pyrethrum extracts that activated sst-1A neurons (FIG. 4A). The pyrethrins can have the structure shown in formula I, where the R group can be methyl or $CO_2CH_3$.

I

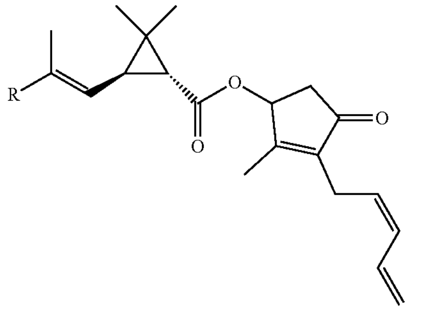

When R is methyl, the compound is pyrethrin I (P-I), but when R is $CO_2CH_3$, the compound is pyrethrin II (P-II).

Figure 4B:
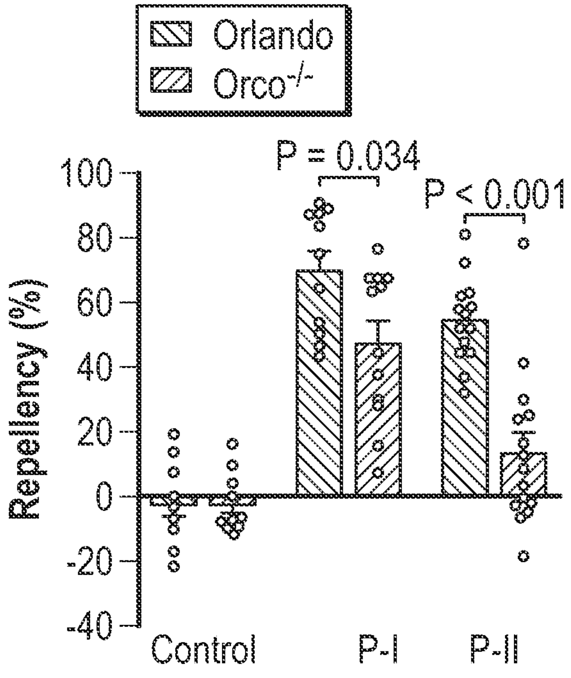

Both pyrethrin I and pyrethrin II elicited spatial repellency at $10^{-3}$ dilution (FIG. 4B). In addition, pyrethrin repellency was significantly reduced in $orco^{-/-}$ mosquitoes (FIG. 4B). Hence, sst-1A neurons have a role in pyrethrin-induced repellency.

Figure 4C:
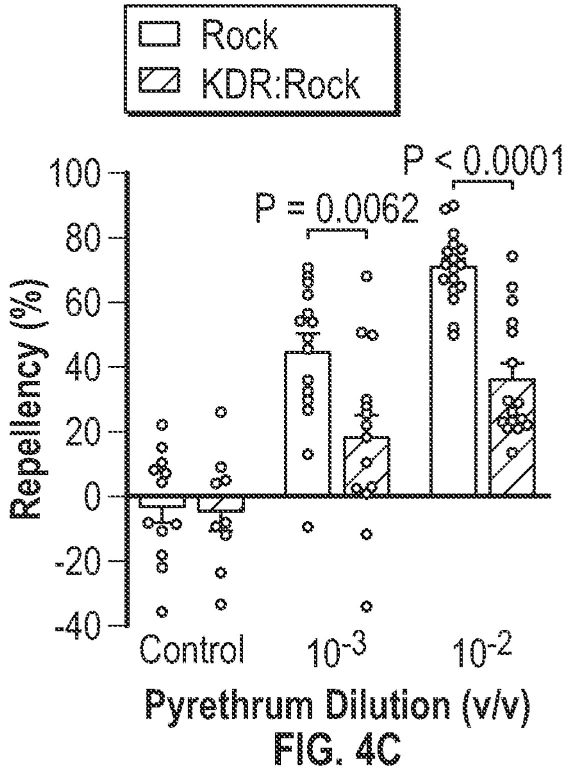
Figure 4D:
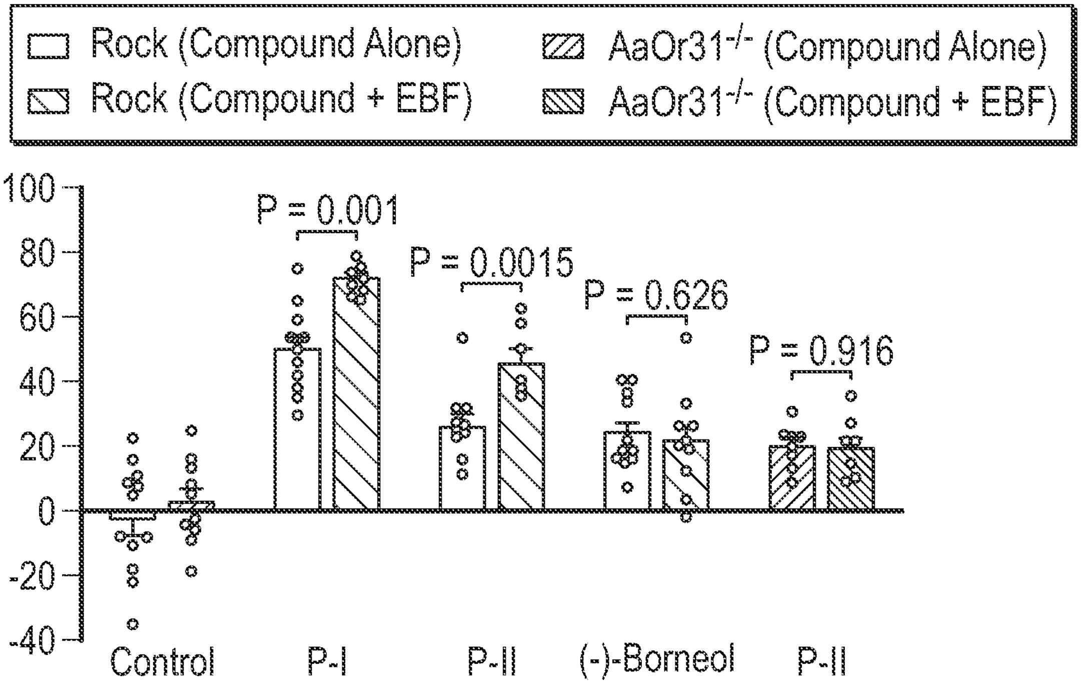
Figure 4E:
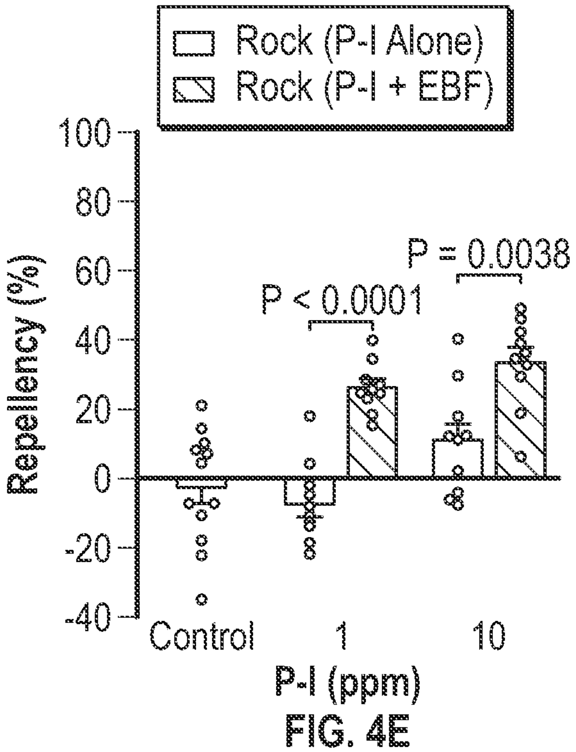
Figure 4F:
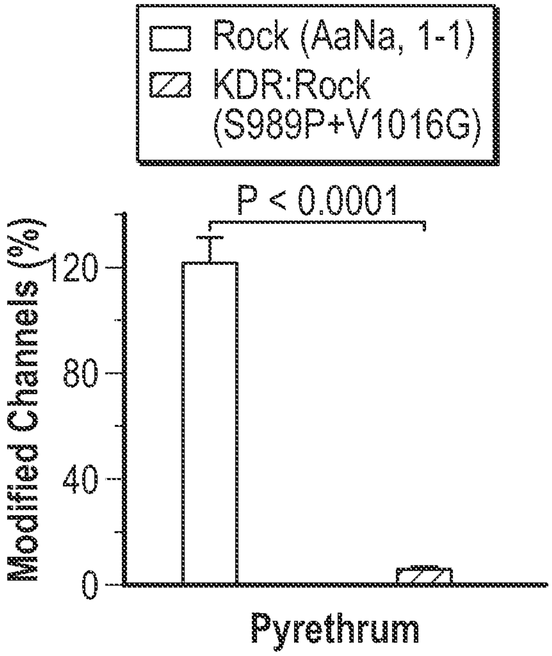
Figure 4G:
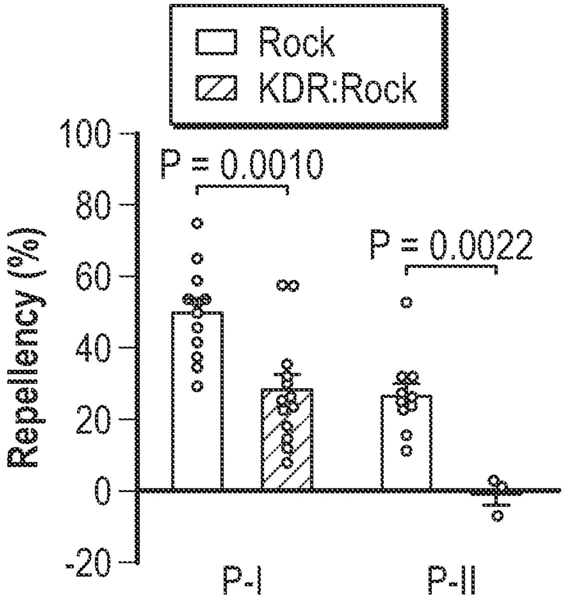
Figure 4H:
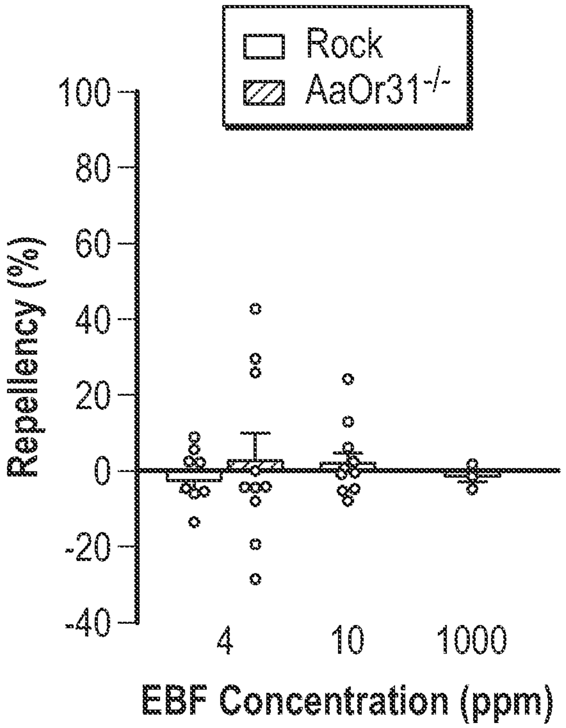
Figure 4I:
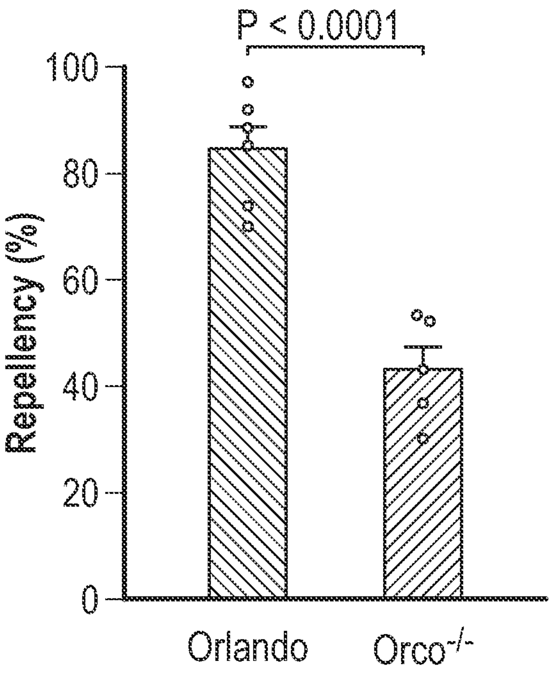

Possible involvement of sodium channels in pyrethrin repellency was also evaluated in the KDR:ROCK mutant line, which is nearly isogenic to the wild-type ROCK strain and is resistant to pyrethrum due to two mutations in the sodium channel (Smith et al. *Pest management science* 74: 737-745 (2018)(FIG. 4F-4G). As shown in FIG. 4C, pyrethrin repellency was reduced compared with ROCK mosquitoes (FIG. 4F-4G). Thus, pyrethrins contribute to pyrethrum repellency via two mechanisms: (i) activation of sst-1A-associated olfactory pathway and (ii) hyper-activation of voltage-gated sodium channels.

Figure 4J:
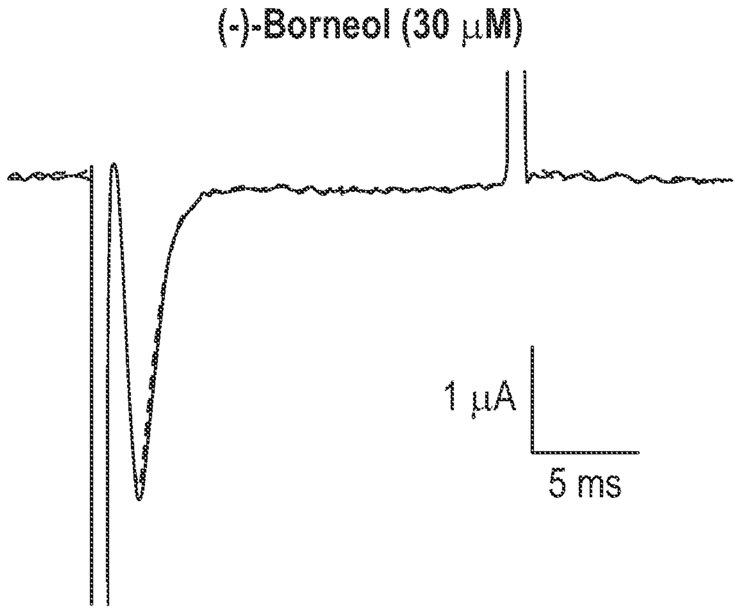

Identification of sst-1A and sbt-1A olfactory receptor neurons and voltage-gated sodium channels as targets of pyrethrum repellency prompted the inventors to consider synergistic interactions between activation of sodium channels and olfactory pathways to maximize insect repellency. To test this possibility, mosquito repellency in response to pyrethrins I/II or (E)-β-farnesene, alone or in combination, was examined. Remarkably, (E)-β-farnesene synergized pyrethrin I or pyrethrin II repellency at a concentration of as low as 4 ppm (FIG. 4D). At concentrations at 4 ppm or below (E)-β-farnesene alone did not exhibit repellency. Interestingly, this synergism between (E)-β-farnesene and pyrethrins was specific. No enhancement in repellency was observed between (E)-β-farnesene and another plant-derived repellent, (−)-borneol (FIG. 4D-4I). Like pyrethrins, (−)-borneol activates sst-1A neurons and elicits Orco-dependent repellency but (−)-borneol cannot activate sodium channels (FIG. 4J). These data indicate that (E)-β-farnesene-pyrethrin synergism requires pyrethrin-mediated activation of sodium channel-activating chemicals.

The repellency enhancement by (E)-β-farnesene was abolished in $AaOr31^{-/-}$ mosquitoes (FIG. 4D), indicating that the enhancement is AaOr31-dependent. Remarkably, the synergism between pyrethrins and (E)-β-farnesene was still evident even when the concentration of pyrethrin I was reduced to 1 ppm at which concentration pyrethrin I alone did not elicit repellency (FIG. 4E). Collectively, these results show that hyper-activation of sodium channels by pyrethrins, together with AaOr31-mediated repellency pathway evoked by (E)-β-farnesene, produce a synergism that is effective against mosquitoes and likely other insects.

Other compounds may also exhibit synergistic repellency through activation of sodium channels by pyrethrins and activation of AgOr31.

Example 3: Screen for Insect Repellent Compounds

As described herein, the inventors have identified the odorant receptor, Or31, that mediates repellency. Or31 is conserved in all major human disease-transmitting mosquito species including *Anopheles gambiae*, a primary vector of human malaria; *Aedes aegypti*, the primary mosquito vector of dengue, yellow fever, Zika and chikungunya; *Culex quinquefasciatus*, a primary vector of West Nile virus; *Aedes albopictus*, another major vector of dengue and West Nile virus, and other *Anopheles* species. The inventors believe that Or31 is the first cross-species mosquito odorant receptor that has been identified for mediating repellency in mosquitoes. The Example illustrates that Or31 can be used as a target for isolating a new generation of durable and wide-spectrum insect repellent.

The *Drosophila* empty neuron system can be used and coupled with single sensillum recording (SSR). Alternatively, the *Xenopus* oocyte expression system coupled with two-electrode voltage clamp to screen chemical libraries for compounds that can activate Or31.

Briefly, in this empty neuron system, the endogenous Or gene, Or22a, in the A neurons of ab3 sensilla is deleted and replaced with a mosquito Or31.

Single sensillum recording (SSR) from the chimera ab3 sensilla that is expressing the mosquito Or31 in *D. melanogaster* antennae can be used to examine the activity of the ab3 sensilla. If a compound activates Or31, an increase in firing frequency of ab3 sensilla is detected in response to the compound.

For expression of Or31 in *Xenopus* oocytes, in vitro synthesized cRNA of Or31 will be injected into oocytes. Activation of Or31 by a given compound can be detected using two electrode voltage clamp technique.

Both assays are robust and established to work by the inventors. Over 100 compounds can be screened daily using either method.

REFERENCES

1. J. R. Bloomquist, Ion channels as targets for insecticides. *Annu. Rev. Entomol.* 41, 163-190 (1996).
2. T. Narahashi, Neuroreceptors and ion channels as the basis for drug action: past, present, and future. *J. Pharmacol. Exp. Ther.* 294, 1-26 (2000).
3. D. M. Soderlund, in *Comprehensive Molecular Insect Science*, L. I. Gilbert, K. Iatrou, S. S. Gill, Eds. (Elsevier, Amsterdam, 2005), vol. 5, pp. 1-24.
4. J. E. Casida, G. B. Quistad, *Pyrethrum Flower: Production, Chemistry, Toxicity and Uses*. (Oxford University Press, New York, New York, USA, 1995).
5. S. J. Moore, M. Debboun, "Histroy of insect repellents" *In Insect Repellents: Principles, Methods, and Uses*, M. Debboun, P. S. Frances, D. Strickman, Eds. (CRC Press, Boca Raton, USA, 2007).
6. N. Achee, P. Masuoka, P. Smith, N. Martin, T. Chareonviryiphap, S. Polsomboon, J. Hendarto, J. Grieco, Identifying the effective concentration for spatial repellency of the dengue vector *Aedes aegypti. Parasites & Vectors* 5, 300 (2012).
7. C. S. Bibbs, P. E. Kaufman, Volatile pyrethroids as a potential mosquito abatement tool: A review of pyrethroid-containing spatial repellents. *J. Integr. Pest Manag.* 8, 21 (2017).
8. N. Hill, H. N. Zhou, P. Wang, X. Guo, I. Carneiro, S. J. Moore, A household randomized, controlled trial of the efficacy of 0.03% transfluthrin coils alone and in combination with long-lasting insecticidal nets on the incidence of *Plasmodium falciparum* and *Plasmodium vivax* malaria in Western Yunnan Province, China. *Malar. J.* 13, 208 (2014).
9. A. S. Mmbando, E. P. A. Batista, M. Kilalangongono, M. F. Finda, Marceline, E. P. Mwanga, E. W. Kaindoa, K. Kifungo, R. M. Njalambaha, H. S. Ngowo, A. E. Eiras, F. O. Okumu, Evaluation of a push-pull system consisting of transfluthrin-treated eave ribbons and odour-baited traps for control of indoor- and outdoor-biting malaria vectors. *Malar. J.* 18, 87 (2019).
10. A. S. Mmbando, H. Ngowo, A. Limwagu, M. Kilalangongono, K. Kifungo, F. O. Okumu, Eave ribbons treated with the spatial repellent, transfluthrin, can effectively protect against indoor-biting and outdoor-biting malaria mosquitoes. *Malar. J.* 17, 368 (2018).
11. S. B. Ogoma, A. S. Mmando, J. K. Swai, S. Horstmann, D. Malone, G. F. Killeen, A low technology emanator treated with the volatile pyrethroid transfluthrin confers long term protection against outdoor biting vectors of lymphatic filariasis, arboviruses and malaria. *PLoS Negl. Trop. Dis.* 11, e0005455 (2017).
12. S. B. Ogoma, H. Ngonyani, E. T. Simfukwe, A. Mseka, J. Moore, M. F. Maia, S. J. Moore, L. M. Lorenz, The mode of action of spatial repellents and their impact on vectorial capacity of *Anopheles gambiae* sensu stricto. *PLoS One* 9, e110433 (2014).
13. S. M. Boyle et al., see website at biorxiv.org/content/10.1101/060178v1.full (2016).
14. Materials and methods are available as supplementary materials at the Science website.
15. K. Sato, M. Pellegrino, T. Nakagawa, T. Nakagawa, L. B. Vosshall, K. Touhara, Insect olfactory receptors are heteromeric ligand-gated ion channels. *Nature* 452, 1002-1006 (2008).
16. M. C. Larsson, A. I. Domingos, W. D. Jones, M. E. Chiappe, H. Amrein, L. B. Vosshall, Or83b encodes a broadly expressed odorant receptor essential for *Drosophila* olfaction. *Neuron* 43, 703-714 (2004).
17. M. DeGennaro, C. S. McBride, L. Seeholzer, T. Nakagawa, E. J. Dennis, C. Goldman, N. Jasinskiene, A. A. James, L. B. Vosshall, orco mutant mosquitoes lose strong preference for humans and are not repelled by volatile DEET. *Nature* 498, 487-491 (2013).
18. A. F. Carey, J. R. Carlson, Insect olfaction from model systems to disease control. *Proc. Natl. Acad. Sci. USA* 108, 12987-12995 (2011).
19. W. S. Leal, Odorant reception in insects: roles of receptors, binding proteins, and degrading enzymes. *Annu. Rev. Entomol.* 58, 373-391 (2013).
20. L. B. Vosshall, R. F. Stocker, Molecular architecture of smell and taste in *Drosophila. Annu. Rev. Neurosci.* 30, 505-533 (2007).
21. M. Ghaninia, R. Ignell, B. S. Hansson, Functional classification and central nervous projections of olfactory receptor neurons housed in antennal trichoid sensilla of female yellow fever mosquitoes, *Aedes aegypti. Eur. J. Neurosci.* 26, 1611-1623 (2007).
22. A. F. Carey, G. Wang, C. Y. Su, L. J. Zwiebel, J. R. Carlson, Odorant reception in the malaria mosquito *Anopheles gambiae. Nature* 464, 66-71 (2010).
23. T. T. Cai, M. Ye, Z. Y. Li, L. M. Fan, Y. G. Zha, J. Wang, "Investigation of the main chemical compounds in pyrethrum extract obtained by supercritical fluid extraction" In *Advanced Materials Research*, L. Yu, J. Guo, G. Yi, Q. Yu, Eds. (Trans Tech Publications, Switzerland, 2013), vols. 781-784, pp. 737-740.
24. C. A. Henrick, "Pyrethroids" In *Agrochemicals from Natural Products*, C. R. A. Godfrey, Ed., (Marcel Dekker, New York, 1995), pp. 63-145.
25. D. R. Maciver, "Constituents of Pyrethrum Extract" In *Pyrethrum Flowers: Production, Chemistry, Toxicology, and Uses*, J. E. Casida, G. B. Quistad, Eds., (Oxford University Press, New York, 1995), pp. 108-122.
26. M. Chen, Y. Du, G. Zhu, G. Takamatsu, M. Ihara, K. Matsuda, B. S. Zhorov, K. Dong, Action of six pyrethrins purified from the botanical insecticide pyrethrum on cockroach sodium channels expressed in *Xenopus* oocytes. *Pestic. Biochem. Physiol.* 151, 82-89 (2018).
27. T. Narahashi, Mode of action of pyrethroids. *Bull. World Health Organ.* 44, 337-345 (1971).
28. L. B. Smith, S. Kasai, J. G. Scott, Voltage-sensitive sodium channel mutations S989P+V1016G in *Aedes aegypti* confer variable resistance to pyrethroids, DDT and oxadiazines. *Pest Manag. Sci.* 74, 737-745 (2018).
29. F. Liu, L. Chen, A. G. Appel, N. Liu, Olfactory responses of the antennal trichoid sensilla to chemical repellents in the mosquito, *Culex quinquefasciatus. J. Insect Physiol.* 59, 1169-1177 (2013).
30. C. J. Den-Otter, M. Behan, F. W. Maes, Single cell responses in female *Pieris brassicae* (Lepidoptera: Pieridae) to plant volatiles and conspecific egg odours. *J. Insect Physiol.* 26, 465-472 (1980).
31. M. Li, M. Bui, T. Yang, C. S. Bowman, B. J. White, O. S. Akbari, Germline Cas9 expression yields highly efficient genome engineering in a major worldwide disease vector, *Aedes aegypti*. *Proc. Natl. Acad. Sci. USA* 114, E10540-E10549 (2017).

32. Y. Du, Y. Nomura, G. Satar, Z. Hu, R. Nauen, S. Y. He, B. S. Zhorov, K. Dong, Molecular evidence for dual pyrethroid-receptor sites on a mosquito sodium channel. *Proc. Natl. Acad. Sci. USA* 110, 11785-11790 (2013).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements describe some of the elements or features of the invention. The statements provide features that can be claimed in the application and the dependencies of the statements illustrate combinations of features that can be present when included in the claims.

Statements

1. A composition comprising one or more activator of an odorant receptor and one or more activator of voltage-gated sodium channels.
2. The composition of statement 1, consisting essentially of one activator of an odorant receptor and one activator of a voltage-gated sodium channel.
3. The composition of statement 1 or 2, wherein the one or more activator of an odorant receptor is (E)-β-farnesene, (±)-lavandulol, (−)-borneol, (−)-α-thujone, norcamphor, camphor, eucalyptol, (+)-fenchone, prenol, indole, guaiacol, 1-octen-3-ol, isoamyl acetate, geranyl acetate, (±)-citronellal, isoamyl alcohol, toluene, sulcatone, citral, bioallethrin, or a combination thereof.
4. The composition of statement 1 or 2, wherein the one or more activator of an odorant receptor is not one or more of (E)-β-farnesene, (±)-lavandulol, (−)-borneol, (−)-α-thujone, norcamphor, camphor, eucalyptol, (+)-fenchone, prenol, indole, guaiacol, 1-octen-3-ol, isoamyl acetate, geranyl acetate, (±)-citronellal, isoamyl alcohol, toluene, sulcatone, citral, bioallethrin, or a combination thereof
5. The composition of statement 1-3 or 4, wherein the one or more activator of an odorant receptor activates an sst-1 olfactory receptor neuron.
6. The composition of statement 5, wherein the one or more activator is one or more of (E)-β-farnesene, (±)-lavandulol, (−)-borneol, (−)-α-thujone, norcamphor, camphor, eucalyptol, (+)-fenchone, prenol, indole, guaiacol, 1-octen-3-ol, isoamyl acetate, geranyl acetate, (±)-citronellal, isoamyl alcohol, toluene, sulcatone, citral, bioallethrin, or a combination thereof.
7. The composition of statement 5 or 6, wherein the one or more activator is one or more of (E)-β-farnesene, isoamyl acetate, geranyl acetate, (±)-citronellal, sulcatone, citral, or a combination thereof.
8. The composition of statement 1-6 or 7, wherein the one or more activator of an odorant receptor activates an sst-2 olfactory receptor neuron.
9. The composition of statement 8, wherein the activator is one or more of (E)-β-farnesene, (±)-lavandulol, (−)-borneol, (−)-α-thujone, norcamphor, camphor, eucalyptol, (+)-fenchone, prenol, guaiacol, isoamyl acetate, (±)-citronellal, isoamyl alcohol, sulcatone, citral, bioallethrin, or a combination thereof.
10. The composition of statement 1-8 or 9, wherein the one or more activator of an odorant receptor activates an sst-3 olfactory receptor neuron.
11. The composition of statement 10, wherein the one or more activator is (E)-β-farnesene, (−)-borneol, norcamphor, prenol, guaiacol, isoamyl alcohol, toluene, or a combination thereof
12. The composition of statement 1-10 or 11, wherein the one or more activator of an odorant receptor activates an sbt-1 olfactory receptor neuron.
13. The composition of statement 12, wherein the activator is (E)-β-farnesene, indole, isoamyl acetate, geranyl acetate, (±)-citronellal, toluene, sulcatone, citral, bioallethrin, or a combination thereof
14. The composition of statement 1-12 or 13, wherein the composition activates sst-1A and sbt-1A olfactory pathways.
15. The composition of statement 1-13 or 14, wherein the one or more activator of an odorant receptor activates an sbt-2 olfactory receptor neuron.
16. The composition of statement 15, wherein the activator is (E)-β-farnesene, (−)-borneol, (−)-α-thujone, camphor, eucalyptol, (+)-fenchone, isoamyl acetate, geranyl acetate, (±)-citronellal, sulcatone, citral, bioallethrin, or a combination thereof.
17. The composition of statement 1-15 or 16, wherein the one or more activator of an odorant receptor activates an sbt-3 olfactory receptor neuron.
18. The composition of statement 17, wherein the activator is (E)-β-farnesene, (±)-lavandulol, (−)-borneol, (−)-α-thujone, norcamphor, camphor, eucalyptol, (+)-fenchone, guaiacol, 1-octen-3-ol, isoamyl acetate, geranyl acetate, (±)-citronellal, isoamyl alcohol, toluene, sulcatone, citral, bioallethrin, or a combination thereof
19. The composition of statement 1-17 or 18, wherein the one or more activator of an odorant receptor activates an sbt-4 olfactory receptor neuron
20. The composition of statement 19, wherein the activator is (E)-β-farnesene, (−)-borneol, (−)-α-thujone, norcamphor, camphor, eucalyptol, (+)-fenchone, prenol, indole, 1-octen-3-ol, isoamyl acetate, geranyl acetate, (±)-citronellal, isoamyl alcohol, sulcatone, citral, bioallethrin, or a combination thereof.
21. The composition of statement 1-19 or 20, wherein the one or more activator of an odorant receptor activates an sbt-5 olfactory receptor neuron.
22. The composition of statement 21, wherein the activator is (E)-β-farnesene, (−)-borneol, (−)-α-thujone, camphor, eucalyptol, (+)-fenchone, prenol, guaiacol, isoamyl acetate, geranyl acetate, (±)-citronellal, isoamyl alcohol, toluene, sulcatone, citral, bioallethrin, or a combination thereof.
23. The composition of statement 1-21 or 22, wherein the one or more activator of an odorant receptor activates an sbt-6 olfactory receptor neuron is (E)-β-farnesene, (−)-α-thujone, 1-octen-3-ol, isoamyl acetate, geranyl acetate, (±)-citronellal, isoamyl alcohol, sulcatone, citral, bioallethrin, or a combination thereof.
24. The composition of statement 1-22 or 23, wherein the odorant receptor comprises odorant receptor 31 (Or31).
25. The composition of statement 1-23 or 24, wherein the one or more activator of voltage-gated sodium channels is a pyrethrin.
26. The composition of statement 1-24 or 25, wherein the one or more activator of voltage-gated sodium channels is Allethrin, Bifenthrin, Cyfluthrin, Cypermethrin, Cyphenothrin, Deltamethrin, Esfenvalerate, Etofenprox, Fenpropathrin, Fenvalerate, Flucythrinate, Flumethrin, Imiprothrin, lambda-Cyhalothrin, Metofluthrin, Permethrin, Resmethrin, Silafluofen, Sumithrin, tau-Fluvalinate, Tefluthrin, Tetramethrin, Tralomethrin, Transfluthrin, pyrethrin I, pyrethrin II, or a combination thereof.

27. The composition of statement 1-24 or 25, wherein the activator of voltage-gated sodium channel is one of Allethrin, Bifenthrin, Cyfluthrin, Cypermethrin, Cyphenothrin, Deltamethrin, Esfenvalerate, Etofenprox, Fenpropathrin, Fenvalerate, Flucythrinate, Flumethrin, Imiprothrin, lambda-Cyhalothrin, Metofluthrin, Permethrin, Resmethrin, Silafluofen, Sumithrin, tau-Fluvalinate, Tefluthrin, Tetramethrin, Tralomethrin, Transfluthrin, pyrethrin I, or pyrethrin II.

28. The composition of statement 1-26 or 27, wherein the one or more activator of voltage-gated sodium channels is a compound of formula I:

I

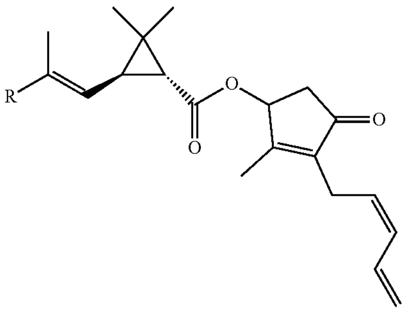

where R is methyl or $CO_2CH_3$.

29. The composition of statement 1-27 or 29, wherein the one or more activator of voltage-gated sodium channels is pyrethrin I (R is methyl), pyrethrin II (R is $CO_2CH_3$), or a combination thereof 30. The composition of any of 1-28 or 29, wherein the one or more activator of voltage-gated sodium channels is one of pyrethrin I (R is methyl), or pyrethrin II (R is $CO_2CH_3$).

31. The composition of any of 1-29 or 30, comprising farnesene, geranyl acetate, and citronellal.

32. The composition of statement 1-30 or 31, formulated for topical application, aerosol application, or spray application.

33. A method comprising distributing into the environment, onto an animal, or onto a surface a composition comprising one or more activator of an odorant receptor and one or more activator of voltage-gated sodium channels.

34. The method of statement 33, wherein the composition consists essentially of one or more activator of an odorant receptor and one or more activator of a voltage-gated sodium channel.

35. The method of statement 33 or 34, wherein the one or more activator of an odorant receptor is (E)-β-farnesene, (±)-lavandulol, (−)-borneol, (−)-α-thujone, norcamphor, camphor, eucalyptol, (+)-fenchone, prenol, indole, guaiacol, 1-octen-3-ol, isoamyl acetate, geranyl acetate, (±)-citronellal, isoamyl alcohol, toluene, sulcatone, citral, bioallethrin, or a combination thereof.

36. The method of statement 33 or 34, wherein the one or more activator of an odorant receptor is not one or more of (E)-β-farnesene, (±)-lavandulol, (−)-borneol, (−)-α-thujone, norcamphor, camphor, eucalyptol, (+)-fenchone, prenol, indole, guaiacol, 1-octen-3-ol, isoamyl acetate, geranyl acetate, (±)-citronellal, isoamyl alcohol, toluene, sulcatone, citral, bioallethrin, or a combination thereof 37. The method of statement 33-35 or 36, wherein the one or more activator of an odorant receptor activates an sst-1 olfactory receptor neuron.

38. The method of statement 37, wherein the one or more activator is one or more of (E)-β-farnesene, (±)-lavandulol, (−)-borneol, (−)-α-thujone, norcamphor, camphor, eucalyptol, (+)-fenchone, prenol, indole, guaiacol, 1-octen-3-ol, isoamyl acetate, geranyl acetate, (±)-citronellal, isoamyl alcohol, toluene, sulcatone, citral, bioallethrin, or a combination thereof.

39. The method of statement 37 or 38, wherein the one or more activator is one or more of (E)-β-farnesene, isoamyl acetate, geranyl acetate, (±)-citronellal, sulcatone, citral, or a combination thereof.

40. The method of statement 33-38 or 39, wherein the one or more activator of an odorant receptor activates an sst-2 olfactory receptor neuron.

41. The method of statement 40, wherein the activator is one or more of (E)-β-farnesene, (±)-lavandulol, (−)-borneol, (−)-α-thujone, norcamphor, camphor, eucalyptol, (+)-fenchone, prenol, guaiacol, isoamyl acetate, (±)-citronellal, isoamyl alcohol, sulcatone, citral, bioallethrin, or a combination thereof.

42. The method of statement 33-40 or 41, wherein the one or more activator of an odorant receptor activates an sst-3 olfactory receptor neuron.

43. The method of statement 42, wherein the one or more activator is (E)-β-farnesene, (−)-borneol, norcamphor, prenol, guaiacol, isoamyl alcohol, toluene, or a combination thereof 44. The method of statement 33-42 or 43, wherein the one or more activator of an odorant receptor activates an sbt-1 olfactory receptor neuron.

45. The method of statement 44, wherein the activator is (E)-β-farnesene, bioallethrin, indole, isoamyl acetate, geranyl acetate, (±)-citronellal, toluene, sulcatone, citral, or a combination thereof.

46. The method of statement 33-44 or 45, wherein the composition activates sst-1A and sbt-1A olfactory pathways.

47. The method of statement 33-45 or 46, wherein the one or more activator of an odorant receptor activates an sbt-2 olfactory receptor neuron.

48. The method of statement 47, wherein the activator is (E)-β-farnesene, (−)-borneol, (−)-α-thujone, camphor, eucalyptol, (+)-fenchone, isoamyl acetate, geranyl acetate, (±)-citronellal, sulcatone, citral, bioallethrin, or a combination thereof.

49. The method of statement 33-47 or 48, wherein the one or more activator of an odorant receptor activates an sbt-3 olfactory receptor neuron.

50. The method of statement 49, wherein the activator is (E)-β-farnesene, (±)-lavandulol, (−)-borneol, (−)-α-thujone, norcamphor, camphor, eucalyptol, (+)-fenchone, guaiacol, 1-octen-3-ol, isoamyl acetate, geranyl acetate, (±)-citronellal, isoamyl alcohol, toluene, sulcatone, citral, bioallethrin, or a combination thereof 51. The method of statement 33-49 or 50, wherein the one or more activator of an odorant receptor activates an sbt-4 olfactory receptor neuron
52. The method of statement 51, wherein the activator is (E)-β-farnesene, (−)-borneol, (−)-α-thujone, norcamphor, camphor, eucalyptol, (+)-fenchone, prenol, indole, 1-octen-3-ol, isoamyl acetate, geranyl acetate, (±)-citronellal, isoamyl alcohol, sulcatone, citral, bioallethrin, or a combination thereof.
53. The method of statement 33-51 or 52, wherein the one or more activator of an odorant receptor activates an sbt-5 olfactory receptor neuron.
54. The method of statement 53, wherein the activator is (E)-β-farnesene, (−)-borneol, (−)-α-thujone, camphor, eucalyptol, (+)-fenchone, prenol, guaiacol, isoamyl acetate, geranyl acetate, (±)-citronellal, isoamyl alcohol, toluene, sulcatone, citral, bioallethrin, or a combination thereof.
55. The method of statement 33-53 or 54, wherein the one or more activator of an odorant receptor activates an sbt-6 olfactory receptor neuron.
56. The method of statement 55, wherein the activator is (E)-β-farnesene, (−)-α-thujone, 1-octen-3-ol, isoamyl acetate, geranyl acetate, (±)-citronellal, isoamyl alcohol, sulcatone, citral, bioallethrin, or a combination thereof.
57. The method of statement 33-55 or 56, wherein the odorant receptor comprises odorant receptor 31 (Or31).
58. The method of statement 33-56 or 57, wherein the one or more activator of voltage-gated sodium channels is a pyrethrin.
59. The method of statement 33-57 or 58, wherein the one or more activator of voltage-gated sodium channels is Allethrin, Bifenthrin, Cyfluthrin, Cypermethrin, Cyphenothrin, Deltamethrin, Esfenvalerate, Etofenprox, Fenpropathrin, Fenvalerate, Flucythrinate, Flumethrin, Imiprothrin, lambda-Cyhalothrin, Metofluthrin, Permethrin, Resmethrin, Silafluofen, Sumithrin, tau-Fluvalinate, Tefluthrin, Tetramethrin, Tralomethrin, Transfluthrin, pyrethrin I, pyrethrin II, or a combination thereof.
60. The method of statement 33-58 or 59, wherein the activator of voltage-gated sodium channel is one of Allethrin, Bifenthrin, Cyfluthrin, Cypermethrin, Cyphenothrin, Deltamethrin, Esfenvalerate, Etofenprox, Fenpropathrin, Fenvalerate, Flucythrinate, Flumethrin, Imiprothrin, lambda-Cyhalothrin, Metofluthrin, Permethrin, Resmethrin, Silafluofen, Sumithrin, tau-Fluvalinate, Tefluthrin, Tetramethrin, Tralomethrin, Transfluthrin, pyrethrin I, or pyrethrin II.
61. The method of statement 33-59 or 60, wherein the one or more activator of voltage-gated sodium channels is a compound of formula I:

I

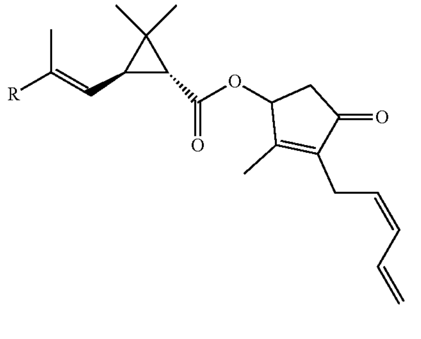

where R is methyl or $CO_2CH_3$.

62. The method of statement 33-60 or 61, wherein the one or more activator of voltage-gated sodium channels is pyrethrin I (R is methyl), pyrethrin II (R is $CO_2CH_3$), or a combination thereof
63. The method of statement 33-61 or 62, wherein the one or more activator of voltage-gated sodium channels is one of pyrethrin I (R is methyl), or pyrethrin II (R is $CO_2CH_3$).
64. The method of statement 33-62 or 63, wherein the composition comprises farnesene, geranyl acetate, and citronellal.
65. The method of statement 33-63 or 64, wherein the composition is formulated for topical application, aerosol application, or spray application.
66. The method of statement 33-64 or 65, wherein distributing comprises spraying or topically applying the composition to the environment, to an animal, or to a surface.
67. A method comprising:
    a. contacting a chimera ab3 sensilla that expresses a mosquito odorant receptor in an empty neuron *Drosophila melanogaster* antenna with at least one test compound;
    b. recording firing frequencies of the chimera ab3 sensilla to thereby identify at least one test insect repellent compound.
68. The method of statement 67, wherein an empty neuron *Drosophila melanogaster* has deleted endogenous odorant receptor 22a (Or22a) gene and does not express Or22a in A neurons of the chimera ab3 sensilla and instead expresses the mosquito odorant receptor in the A neurons of the chimera ab3 sensilla.
69. The method of statement 67 or 68, wherein the test insect repellent compound increases in firing frequency of the chimera ab3 sensilla.
70. The method of statement 67, 68 or 69, wherein the mosquito odorant receptor is an odorant receptor 31.
71. The method of statement 67-69 or 70, wherein the mosquito odorant receptor is an *Aedes aegypti* odorant receptor 31 (Or31), an *Anopheles gambiae* odorant receptor 20 (Or20), an *Anopheles gambiae* odorant receptor 31 (Or31), an *Anopheles gambiae* odorant receptor 53 (Or53), or an *Anopheles gambiae* odorant receptor 76 (Or76).
72. The method of statement 67-70 or 71, further comprising applying the test insect repellent compound to a test window of a hand-in-cage apparatus and scoring the number of insects that land on the test window compared to the number of insects that land on a control window of a hand-in-cage apparatus.
73. The method of statement 72, wherein the control window is a negative control window that has no test compound and no insect repellent compounds thereon.
74. The method of statement 72, wherein the control window is a positive control window that has at least one insect repellent compounds thereon.
75. A composition comprising at least one test insect repellent compound that exhibits increased firing frequency of a chimera ab3 sensilla in a method comprising:
    a. contacting the chimera ab3 sensilla that expresses a mosquito odorant receptor in an empty neuron *Drosophila melanogaster* antenna with at least one test compound;

b. recording firing frequencies of the chimera ab3 sensilla to thereby identify the at least one test insect repellent compound.

The specific plants, plant cells, seeds, methods, and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A method of identifying an insect repellent compound, the method comprising:

a. contacting at least one test compound with an insect sensilla that expresses an odorant receptor 31 (Or31) gene product, wherein the odorant receptor 31 (Or31) gene product comprises a polypeptide with at least 95% sequence identity to SEQ ID NO: 1 or 2; and b. recording firing frequencies of the sensilla to thereby detect at least one insect repellant compound in the test compound, wherein the test compound is determined to comprise the at least one insect repellant compound based on increased firing frequencies of the sensilla contacted with the test compound compared to sensilla not contacted with the test compound.

2. The method of claim 1, wherein the odorant receptor 31 (Or31) is a wild type odorant receptor 31 (Or31).

3. The method of claim 1, wherein the odorant receptor 31 (Or31) is a mutant odorant receptor 31 (Or31).

4. The method of claim 1, wherein the odorant receptor 31 (Or31) is a mosquito odorant receptor coding region.

5. The method of claim 1, wherein the odorant receptor 31 (Or31) is an *Aedes aegypti* odorant receptor 31 (Or31).

6. The method of claim 1, wherein test insect repellent compound(s) that cause increased firing frequency of the sensilla are selected for further testing.

7. The method of claim 1, further comprising applying one or more of the test insect repellent compounds to a test window of a hand-in-cage apparatus and scoring the number of insects that land on the test window compared to the number of insects that land on a control window of a hand-in-cage apparatus.

8. The method of claim 7, wherein the control window is a negative control window that has no test compound and no insect repellent compounds thereon.

9. The method of claim 7, wherein the control window is a positive control window that has at least one insect repellent compound thereon.

10. The method of claim 1, wherein the test compound comprises a volatile compound.

11. The method of claim 10, wherein the volatile compound comprises pyrethrum.

* * * * *